US008722629B2

(12) United States Patent
Lerchen et al.

(10) Patent No.: US 8,722,629 B2
(45) Date of Patent: May 13, 2014

(54) AURISTATIN DERIVATIVES AND USE THEREOF

(75) Inventors: Hans-Georg Lerchen, Leverkusen (DE); Beatrix Stelte-Ludwig, Wulfrath (DE); Sven Golfier, Berlin (DE); Joachim Schuhmacher, Wuppertal (DE); Ursula Krenz, Leichlingen (DE)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 13/702,881

(22) PCT Filed: Jun. 6, 2011

(86) PCT No.: PCT/EP2011/059300
§ 371 (c)(1),
(2), (4) Date: Feb. 20, 2013

(87) PCT Pub. No.: WO2011/154359
PCT Pub. Date: Dec. 15, 2011

(65) Prior Publication Data
US 2013/0157960 A1 Jun. 20, 2013

(30) Foreign Application Priority Data

Jun. 10, 2010 (EP) .................................. 10165550
Mar. 16, 2011 (EP) .................................. 11158464

(51) Int. Cl.
*A61K 38/00* (2006.01)
*A61K 35/00* (2006.01)
*A61K 38/08* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl.
USPC ......... 514/19.3; 530/330; 514/21.8; 514/19.2

(58) Field of Classification Search
None
See application file for complete search history.

(56) References Cited

U.S. PATENT DOCUMENTS

| 6,884,869 | B2 | 4/2005 | Senter et al. | |
|---|---|---|---|---|
| 8,288,352 | B2 | 10/2012 | Doronina et al. | |
| 2002/0147138 | A1 | 10/2002 | Firestone et al. | |
| 2013/0066055 | A1* | 3/2013 | Lerchen et al. | 530/391.9 |
| 2013/0095123 | A1* | 4/2013 | Lerchen et al. | 424/179.1 |
| 2013/0122024 | A1* | 5/2013 | Lerchen et al. | 424/179.1 |

FOREIGN PATENT DOCUMENTS

| WO | 96/18408 | A1 | 6/1996 |
|---|---|---|---|
| WO | 99/35164 | A1 | 7/1999 |
| WO | 01/18032 | A2 | 3/2001 |
| WO | 2002/088172 | A2 | 11/2002 |
| WO | 03/008378 | A1 | 1/2003 |
| WO | 03/026577 | A2 | 4/2003 |
| WO | 2004/010957 | A2 | 2/2004 |
| WO | 2005/081711 | A2 | 9/2005 |
| WO | 2007/008603 | A1 | 1/2007 |
| WO | 2007/008848 | A2 | 1/2007 |
| WO | WO 2007008603 | A1 * | 1/2007 |
| WO | 2008/052187 | A2 | 5/2008 |
| WO | 2009/117531 | A1 | 9/2009 |

OTHER PUBLICATIONS

International Search Report dated Aug. 18, 2011, issued in corresponding International Application No. PCT/EP2011/059300. (4 pages).
International Preliminary Report on Patentability (Form PCT/IB/373) and the Written Opinion of the International Searching Authority (Form PCT/ISA/237) dated Dec. 20, 2012, issued in corresponding International Application No. PCT/EP2011/059300. (7 pages).
Lambert, "Drug-conjugated monoclonal antibodies for the treatment of cancer" Curr. Opin. Parmacol., (2005) pp. 543-549, vol. 5.
Wu et al., "Arming antibodies: prospects and challenges for immunoconjugates" Nat. Biotechno. (2005) pp. 1137-1146, vol. 23.
Senter, "Potent antibody drug conjugates for cancer therapy" Curr. Opin. Chem. Biol. (2009) pp. 235-244, vol. 13.
Ducry et al., "Antibody-Drug Conjugates: Linking Cytotoxic Payloads to Monoclonal Antibodies" Bioconjugate Chem. (2010), pp. 5-13, vol. 21.
Arap et al., "Cancer Treatment by Targeted Drug Delivery to Tumor Vasculature in a Mouse Model" Science (1998) pp. 377-380, vol. 279.
Karkan et al., "A Unique Carrier for Delivery of Therapeutic Compounds beyond the Blood-Brain Barrier" PloS ONE (2008) pp. 1-14, vol. 3 No. 6, e 2469.
Pettit, "The Dolastatins" Prog. Chem. Org. Nat. Prod. (1997) pp. 1-79, vol. 70.
Pettit et al., "Antineoplastic agents 337. Synthesis of dolastatin 10 structural modifications" Anti-Cancer Drug Design (1995) pp. 529-544, vol. 10.

(Continued)

*Primary Examiner* — Cecilia J Tsang
*Assistant Examiner* — Zachary J Miknis
(74) *Attorney, Agent, or Firm* — Buchanan Ingersoll & Rooney PC

(57) ABSTRACT

The present application relates to novel derivatives of monomethylauristatin F, to processes for preparing these derivatives, to the use of these derivatives for treating and/or preventing diseases, and also to the use of these derivatives for preparing medicaments for treating and/or preventing diseases, more particularly hyperproliferative and/or angiogenic disorders such as, for example, cancerous disorders. Such treatments may be practised as a monotherapy or else in combination with other medicaments or further therapeutic measures.

21 Claims, No Drawings

(56) References Cited

OTHER PUBLICATIONS

Pettit et al., "Antineoplastic agents 365. Dolastatin 10 SAR probes" Anti-Cancer Drug Design (1998) pp. 243-277, vol. 13.

Doronina et al., "Enhanced Activity of Monomethylauristatin F through Monoclonal Antibody Delivery: Effects of Linker Technology on Efficacy and Toxicity" Bioconjugate Chem. (2006) pp. 114-124, vol. 17, (XP55009264).

Doronina et al., "Novel Peptide Linkers for Highly Potent Antibody-Auristatin Conjugate" Bioconjugate Chem. (2008) pp. 1960-1963, vol. 19.

Bajjuri et al., "The Legumain Protease-Activated Auristatin Prodrugs Suppress Tumor Growth and Metastasis without Toxicity", ChemMedChem (2011) pp. 54-59, vol. 6, No. 1, (XP55009266).

* cited by examiner

AURISTATIN DERIVATIVES AND USE THEREOF

CROSS-REFERENCE TO RELATED APPLICATIONS

This application is the national stage filing under 35 U.S.C. §371 of International Application No. PCT/EP2011/059300 filed Jun. 6, 2011, which claims the benefit of European Patent. Application No. 10165550.4, filed Jun. 10, 2010 and European Patent Application No. 11158464.5, filed Mar. 16, 2011; each of which is incorporated by reference in its entirety.

The present application relates to novel derivatives of monomethylauristatin F, to processes for preparing these derivatives, to the use of these derivatives for treating and/or preventing diseases, and also to the use of these derivatives for preparing medicaments for treating and/or preventing diseases, more particularly hyperproliferative and/or angiogenic disorders such as, for example, cancerous disorders. Such treatments may be practised as a monotherapy or else in combination with other medicaments or further therapeutic measures.

Cancerous disorders are the consequence of uncontrolled cell growth in a wide variety of tissues. In many cases the new cells penetrate existing tissue (invasive growth), or they metastase into remote organs. Cancerous disorders occur in a wide variety of organs, and the diseases often progress in a tissue-specific manner. The designation "cancerous disorder" as a generic term therefore describes a large group of defined diseases of different organs, tissues and cell types.

Early-stage tumours may be able to be removed by surgical and radiotherapeutic measures. Metastasized tumours can generally only be given palliative therapy by means of chemotherapeutic agents. The objective in that case is to achieve the optimum combination of improving quality of life and prolonging remaining lifetime.

The majority of the chemotherapeutic agents which are presently administered parenterally are often not target-directed at the tumour tissue or the tumour cells, but instead, as a result of their systemic administration, are distributed non-specifically within the body, hence including at locations at which exposure to the drug is undesirable, such as in healthy cells, tissues and organs, for example. This may lead to unwanted side-effects and even to serious effects of general toxicity, which then often greatly limit the therapeutically useful dose range of the drug, or necessitate complete cessation of medication.

The improved and selective availability of these chemotherapeutic agents in the tumour cell or the immediately surrounding tissue, and the associated boost in effect, on the one hand, and minimization of toxic side-effects, on the other hand, have therefore been a focal point for a number of years in the development of new chemotherapeutic agents. Many attempts have been made to date to develop efficient methods of introducing the drug into the target cell. Optimizing the association between drug and intracellular target and minimizing the intercellular distribution of drug, to adjacent cells, for example, nevertheless continue to constitute a difficult problem.

Monoclonal antibodies, for example, are suitable for the target-directed addressing of tumour tissue and tumour cells. The significance of such antibodies for the clinical treatment of cancerous disorders has seen a considerable general increase in recent years, based on the activity of such agents as trastuzumab (Herceptin), rituximab (Rituxan), cetuximab (Erbitux) and bevacizumab (Avastin), which have since been approved for the therapy of individual, specific tumour disorders [see, for example, G. P. Adams and L. M. Weiner, *Nat. Biotechnol.* 23, 1147-1157 (2005)]. Consequently there has also been a marked increase in interest in so-called immunoconjugates such as, for example, the aforementioned ADCs, in which an internalizing antibody directed against a tumour-associated antigen is joined covalently via a linking unit ("linker") to a cytotoxic agent. Following introduction of the ADC into the tumour cell and subsequent cleavage of the conjugate, either the cytotoxic agent itself or another metabolite with cytotoxic activity, formed from the cytotoxic agent, is released within the tumour cell, where it is able to develop its effect directly and selectively. In this way it would be possible to keep the damage to normal tissue within significantly closer limits in comparison to a conventional chemotherapy of the cancerous disorder [see, for example, J. M. Lambert, *Curr. Opin. Pharmacol.* 5, 543-549 (2005); A. M. Wu and P. D. Senter, *Nat. Biotechnol.* 23, 1137-1146 (2005); P. D. Senter, *Curr. Opin. Chem. Biol.* 13, 235-244 (2009); L. Ducry and B. Stump, *Bioconjugate Chem.* 21, 5-13 (2010)].

Instead of antibodies, it is also possible for ligands from the small-molecule drug sphere to be used as binders which bind selectively to a specific target location ("target"), such as to a receptor, for example [see, for example, E. Ruoslahti et al., *Science* 279, 377-380 (1998); D. Karkan et al., PLoS ONE 3 (6), e2469 (Jun. 25, 2008)]. Also known are conjugates of cytotoxic drug and addressing ligand that exhibit a defined cleavage point between ligand and drug for the release of the drug. A "predetermined break point" of this kind may exist, for example, within a peptide chain which can be cleaved selectively at a particular site by a specific enzyme at the location of action [see, for example, R. A. Firestone and L. A. Telan, US Patent Application US 2002/0147138].

Auristatin E (AE) and monomethylauristatin E (MMAE) are synthetic analogues of the dolastatins, a specific group of linear pseudopeptides which were originally isolated from marine sources and which have in some cases very potent cytotoxic activity with respect to tumour cells [for a review see, for example, G. R. Pettit, *Prog. Chem. Org. Nat. Prod.* 70, 1-79 (1997); G. R. Pettit et al., *Anti-Cancer Drug Design* 10, 529-544 (1995); G. R. Pettit et al., *Anti-Cancer Drug Design* 13, 243-277 (1998)].

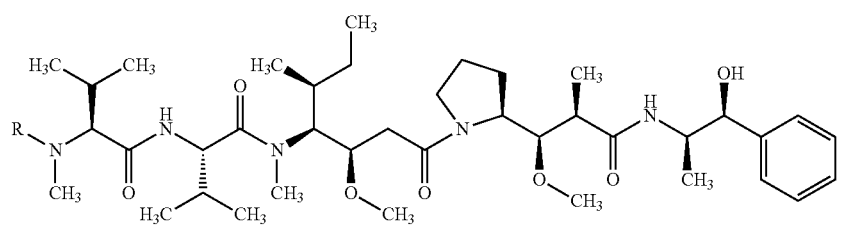

Auristatin E (AE): R=CH₃
Monomethylauristatin E (MMAE): R=H

MMAE, however, possesses the disadvantage of a comparatively high systemic toxicity. In addition, this compound, when applied in the form of antibody/active compound conjugates (immunoconjugates), is incompatible with linkers between antibody and active compound not having an enzymatically cleavable predetermined break point [S. O. Doronina et al., *Bioconjugate Chem.* 17, 114-124 (2006)].

Monomethylauristatin F (MMAF) is an auristatin derivative having a C-terminal phenylalanine unit which exhibits only moderate antiproliferative activity in comparison to MMAE. This fact is very probably attributable to the free carboxyl group, whose polarity and charge adversely affect the capacity of this compound to access cells. In this connection, the methyl ester of MMAF (MMAF-OMe) has been described, as a neutral-charged prodrug derivative with cell access capability, which, in comparison to MMAF, has an in vitro cytotoxicity for various carcinoma cell lines that is increased by a number of orders of magnitude [S. O. Doronina et al., *Bioconjugate Chem.* 17, 114-124 (2006)]. It can be assumed that this effect is brought about by MMAF itself, which, following uptake of the prodrug into the cells, is rapidly released by intracellular ester hydrolysis.

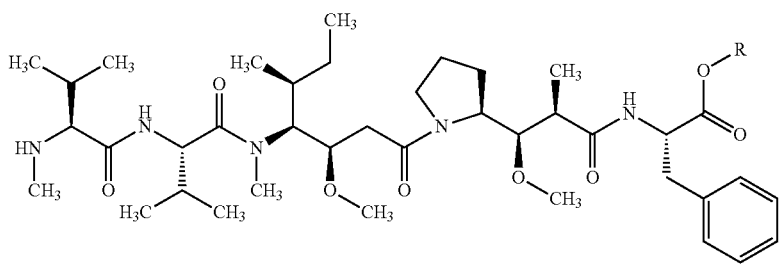

Monomethylauristatin F (MMAF): R=H
Monomethylauristatin F methyl ester (MMAF-OMe): R=CH₃

However, drug compounds based on simple ester derivatives are generally subject to the risk of chemical instability on account of non-specific ester hydrolysis, independent of the intended site of action, by means, for example, of esterases that are present in the blood plasma; this non-specific hydrolysis may significantly restrict the usefulness of such compounds in therapy.

Accordingly, it was an object of the present invention to identify, starting with only moderately effective monomethylauristatin F (MMAF), novel compounds and to provide these compounds which, firstly, have markedly stronger cytotoxic activity in whole-cell assays and, secondly, have increased plasma stability compared to simple ester derivatives such as MMAF-OMe, in particular for the treatment of cancerous disorders. Such substances may be particularly suitable as toxophores for attachment to proteins such as, for example, antibodies, or else to low-molecular-weight ligands to give (immune) conjugates having antiproliferative action.

Monomethylauristatin F (MMAF) and also various ester derivatives and amide derivatives thereof have been disclosed in WO 2005/081711-A2. Further auristatin analogues with a C-terminal, amidically substituted phenylalanine unit are described in WO 01/18032-A2. WO 02/088172-A2 and WO 2007/008603-A1 claim MMAF analogues which relate to side-chain modifications of the phenylalanine, while WO 2007/008848-A2 claims those in which the carboxyl group of the phenylalanine has been modified. Auristatin conjugates linked via the C-terminus have been recently described in WO 2009/117531-A1 [see also S. O. Doronina et al., *Bioconjugate Chem.* 19, 1960-1963 (2008)].

The present invention now provides compounds of the general formula (I)

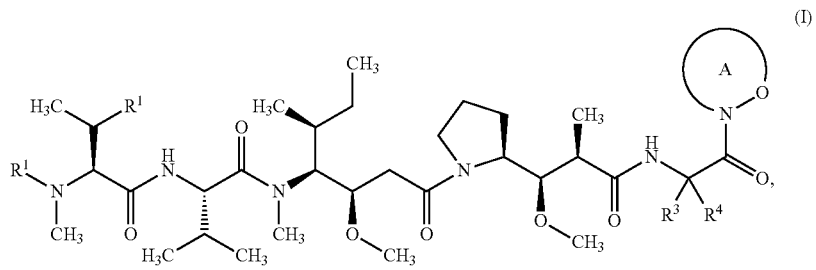

in which
R¹ represents hydrogen, (C₁-C₆)-alkyl or a group of the formula Q¹L¹* or Q²-L²-* in which
  * denotes the point of attachment to the nitrogen atom,
  Q¹ represents hydroxycarbonyl, (C₁-C₄)-alkoxycarbonyl or benzyloxycarbonyl,
  L¹ represents straight-chain (C₁-C₁₂)-alkanediyl which may be substituted up to four times by methyl and in which (a) two carbon atoms may be bridged in 1,2-, 1,3- or 1,4-relation to one another including any carbon atoms located between them to form a $(C_3-C_6)$-cycloalkyl ring or a phenyl ring or (b) up to three $CH_2$ groups not adjacent to one another may be replaced by —O—, $Q^2$ represents hydroxyl, amino or mono-$(C_1-C_4)$-alkylamino and $L^2$ represents straight-chain $(C_2-C_{12})$-alkanediyl which may be substituted up to four times by methyl and in which (a) two carbon atoms may be bridged in 1,2-, 1,3- or 1,4-relation to one another including any carbon atoms located between them to form a $(C_3-C_6)$-cycloalkyl ring or a phenyl ring or (b) up to three $CH_2$ groups not adjacent to one another may be replaced by —O—, $R^2$ represents methyl or hydroxyl, $R^3$ represents hydrogen or methyl, $R^4$ represents isopropyl, isobutyl, sec-butyl, tert-butyl, phenyl, benzyl, 4-hydroxybenzyl, 4-hydroxy-3-nitrobenzyl, 1-phenylethyl, diphenylmethyl, 1H-imidazol-4-ylmethyl or 1H-indol-3-ylmethyl or $R^3$ and $R^4$ together with the carbon atom to which both are attached form a 2-phenylcyclopropane-1,1-diyl group of the formula

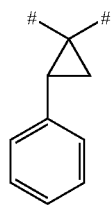

in which # denotes the points of attachment to the other parts of the molecule and ring A with the N—O grouping contained therein represents a mono- or bicyclic, optionally substituted heterocycle of the formula

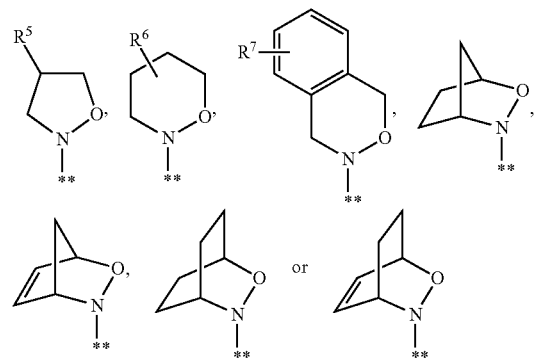

in which

** denotes the point of attachment to the carbonyl group, $R^5$ and $R^6$ each represent hydrogen, hydroxyl, $(C_1-C_4)$-alkoxy or benzyloxy and $R^7$ represents hydrogen, fluorine, chlorine, cyano, methyl or trifluoromethyl, and also their salts, solvates and solvates of the salts.

Compounds of the invention are the compounds of the formula (I) and their salts, solvates and solvates of the salts, the compounds of the formulae identified below and encompassed by formula (I), and their salts, solvates and solvates of the salts, and also the compounds identified below as working examples and encompassed by formula (I), and their salts, solvates and solvates of the salts, to the extent that the compounds identified below and encompassed by formula (I) are not already salts, solvates and solvates of the salts.

Depending on their structure, the compounds of the invention may exist in different stereoisomeric forms, i.e. in the form of configurational isomers or else where appropriate as conformational isomers (enantiomers and/or diastereoisomers, including those in the case of atropisomers). The present invention therefore encompasses the enantiomers and diastereomers and their respective mixtures. The stereoisomerically homogeneous constituents can be isolated from such mixtures of enantiomers and/or diastereomers in a known way; for this purpose it is preferred to use chromatographic processes, more particularly HPLC chromatography on an achiral or chiral phase.

Where the compounds of the invention can occur in tautomeric forms, the present invention encompasses all of the tautomeric forms.

Preferred salts in the context of the present invention are physiologically acceptable salts of the compounds of the invention. Also encompassed are salts which although themselves not suitable for pharmaceutical applications may nevertheless be used, for example, for isolating or purifying the compounds of the invention.

Physiologically acceptable salts of the compounds of the invention encompass acid addition salts of mineral acids, carboxylic acids and sulphonic acids, examples being salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also encompass salts of customary bases, such as, by way of example and preferably, alkali metal salts (e.g. sodium and potassium salts), alkaline earth metal salts (e.g. calcium and magnesium salts) and ammonium salts, derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine.

Solvates in the context of the invention are those forms of the compounds of the invention that form a complex in the solid or liquid state through coordination with solvent molecules. Hydrates are one specific form of solvates, in which the coordination takes place with water. Preferred solvates in the context of the present invention are hydrates.

Furthermore, the present invention also encompasses prodrugs of the compounds of the invention. The term "prodrugs" here identifies compounds which may themselves be biologically active or inactive but are converted during their residence in the body into compounds of the invention (by metabolism or hydrolysis, for example).

In the context of the present invention the definitions of the substituents, unless otherwise specified, are as follows:

In the context of the present invention, $(C_1-C_6)$-alkyl and $(C_1-C_4)$-alkyl represent a straight-chain alkyl or branched alkyl radical having 1 to 6 and 1 to 4 carbon atoms, respectively. Preference is given to a straight-chain or branched alkyl radical having 1 to 4 carbon atoms. By way of example and of preference, the following may be mentioned: methyl, ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

In the context of the present invention, $(C_1-C_{12})$-alkanediyl, $(C_1-C_6)$-alkanediyl, $(C_2-C_{12})$-alkanediyl and $(C_2-C_6)$-alkanediyl represent a straight-chain α,ω-divalent alkyl radical having 1 to 12, 1 to 6, 2 to 12 and 2 to 6 carbon atoms, respectively. By way of example and of preference, the following may be mentioned: methylene, ethane-1,2-diyl (1,2-ethylene), propane-1,3-diyl (1,3-propylene), butane-1,4-diyl (1,4-butylene), pentane-1,5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene), undecane-1,11-diyl (1,11-undecylene) and dodecane-1,12-diyl (1,12-dodecylene).

In the context of the present invention, $(C_3-C_6)$-cycloalkyl represents a monocyclic saturated cycloalkyl group having 3 to 6 carbon atoms. By way of example and of preference, the following may be mentioned: cyclopropyl, cyclobutyl, cyclopentyl and cyclohexyl.

In the context of the present invention, $(C_1-C_4)$-alkoxy represents a straight-chain or branched alkoxy radical having 1 to 4 carbon atoms. By way of example and of preference, the following may be mentioned: methoxy, ethoxy, n-propoxy, isopropoxy, n-butoxy, isobutoxy, sec-butoxy and tert-butoxy.

In the context of the present invention, $(C_1-C_4)$-alkoxycarbonyl represents a straight-chain or branched alkoxy radical having 1 to 4 carbon atoms which is attached via a carbonyl group [—C(=O)—]. By way of example and of preference, the following may be mentioned: methoxy-carbonyl, ethoxy-carbonyl, n-propoxycarbonyl, isopropoxycarbonyl, n-butoxycarbonyl and tert-butoxycarbonyl.

In the context of the present invention, mono-$(C_1-C_4)$-alkylamino represents an amino group having a straight-chain or branched alkyl substituent which has 1 to 4 carbon atoms. By way of example and of preference, the following may be mentioned: methylamino, ethylamino, n-propylamino, isopropylamino, n-butylamino and tert-butylamino.

In the context of the present invention, all radicals which occur multiply have their definition independently of one another. If radicals in the compounds of the invention are substituted, the radicals, unless otherwise specified, may be substituted one or more times. Substitution by one or by two identical or different substituent(s) is preferred. Particularly preferred is substitution by one substituent.

In the context of the present invention, preference is given to compounds of the formula (I) in which
$R^1$ represents hydrogen, $(C_1-C_4)$-alkyl or a group of the formula $Q^1L^1$-* or $Q^2$-$L^2$-* in which
  * denotes the point of attachment to the nitrogen atom,
  $Q^1$ represents hydroxycarbonyl or $(C_1-C_4)$-alkoxycarbonyl,
  $L^1$ represents straight-chain $(C_1-C_{12})$-alkanediyl in which
    (a) two carbon atoms may be bridged in 1,3- or 1,4-relation to one another including the one or the two carbon atom(s) located between them to form a phenyl ring or (b) up to three $CH_2$ groups not adjacent to one another may be replaced by —O—, $Q^2$ represents hydroxyl, amino or methylamino
and
$L^2$ represents straight-chain $(C_2-C_{12})$-alkanediyl which may be mono- or disubstituted by methyl and in which up to three $CH_2$ groups not adjacent to one another may be replaced by —O—,
$R^2$ represents methyl or hydroxyl,
$R^3$ represents hydrogen,
$R^4$ represents benzyl, 4-hydroxybenzyl, 1-phenylethyl or 1H-indol-3-ylmethyl
or
$R^3$ and $R^4$ together with the carbon atom to which both are attached form a 2-phenylcyclopropane-1,1-diyl group of the formula

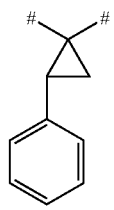

in which
# denotes the points of attachment to the other parts of the molecule
and
ring A with the N—O grouping contained therein represents a mono- or bicyclic, optionally substituted heterocycle of the formula

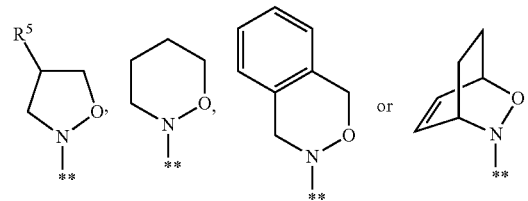

in which
** denotes the point of attachment to the carbonyl group,
and
$R^5$ represents hydrogen, hydroxyl or benzyloxy,
and also their salts, solvates and solvates of the salts.

In the context of the present invention, particular preference is given to compounds of the formula (I) in which
$R^1$ represents hydrogen, methyl or a group of the formula $Q^1$-$L^1$-* or $Q^2L^2$-* in which
  * denotes the point of attachment to the nitrogen atom,
  $Q^1$ represents hydroxycarbonyl, methoxycarbonyl or ethoxycarbonyl,
  $L^1$ represents straight-chain $(C_1-C_6)$-alkanediyl in which two carbon atoms may be bridged in 1,4-relation to one another including the two carbon atoms located between them to form a phenyl ring,
  $Q^2$ represents hydroxyl or amino
  and
  $L^2$ represents straight-chain $(C_2-C_6)$-alkanediyl,
$R^2$ represents methyl,
$R^3$ represents hydrogen,
$R^4$ represents benzyl, 1-phenylethyl or 1H-indol-3-ylmethyl or R³ and R⁴ together with the carbon atom to which both are attached form a (1S,2R)-2-phenyl-cyclopropane-1,1-diyl group of the formula

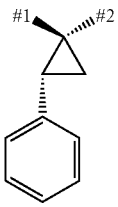

in which
1 denotes the point of attachment to the adjacent nitrogen atom
and
2 denotes the point of attachment to the carbonyl group
and
ring A with the N—O grouping contained therein represents a mono- or bicyclic, optionally substituted heterocycle of the formula

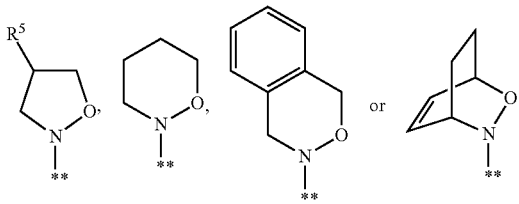

in which
** denotes the point of attachment to the carbonyl group, and
R⁵ represents hydrogen, hydroxyl or benzyloxy,
and also their salts, solvates and solvates of the salts.

Of particular importance in the context of the present invention are compounds of the formula (I-A)

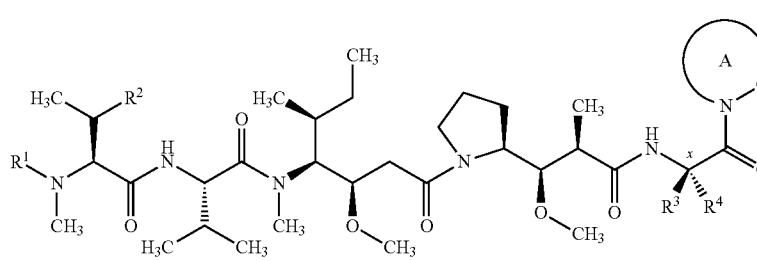

in which R¹, R², R³, R⁴ and ring A have the meanings defined above and the $C^x$ carbon atom carrying the radicals R³ and R⁴ has the S configuration shown,
and also their salts, solvates and solvates of the salts.

Independently of the respective combinations of radicals given, the specific radical definition given in the respective combinations or preferred combinations of radicals are also replaced by radical definitions of other combinations.

Very particular preference is given to combinations of two or more of the preferred ranges mentioned above.

The invention furthermore provides a process for preparing the compounds of the formula (I) according to the invention, characterized in that a compound of the formula (II)

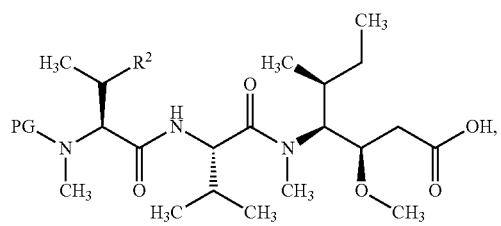

in which R² has the meaning given above
and
PG represents an amino protective group such as, for example, (9H-fluoren-9-ylmethoxy)-carbonyl, tert-butoxycarbonyl or benzyloxycarbonyl
is coupled in an inert solvent with activation of the carboxyl function in (II) either
[A] first with the compound of the formula (III)

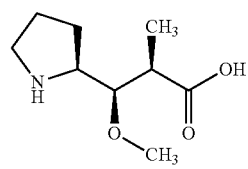

or a salt thereof to give a compound of the formula (IV)

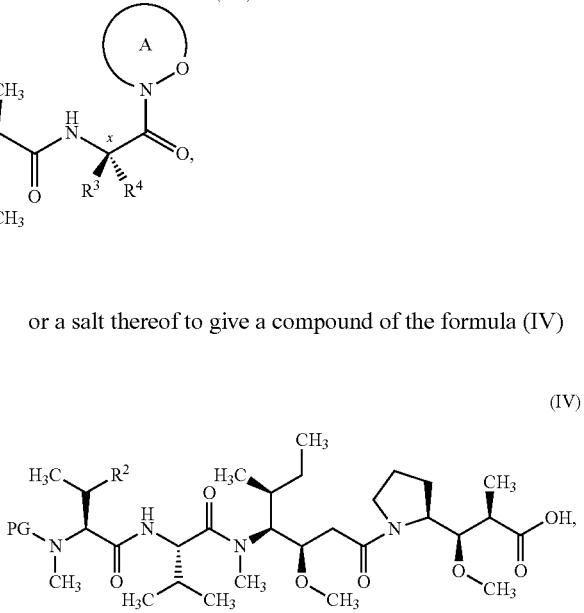

in which $R^2$ and PG have the meanings given above
and this compound is then coupled in an inert solvent with activation of the carboxyl function with a compound of the formula (V)

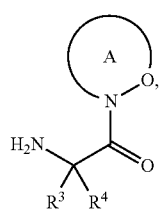

(V)

in which $R^3$, $R^4$ and ring A have the meaning given above or a salt of this compound to give a compound of the formula (VI)

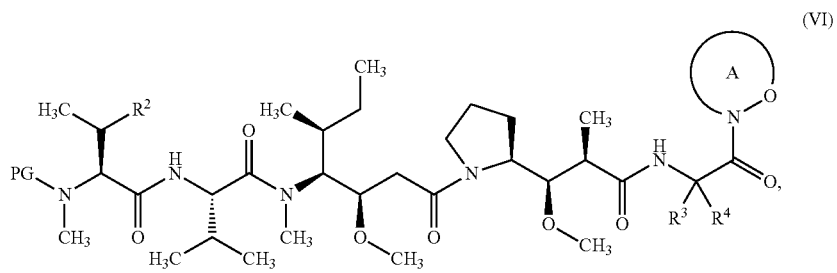

(VI)

in which $R^2$, $R^3$, $R^4$, ring A and PG have the meanings given above, or

[B] with a compound of the formula (VII)

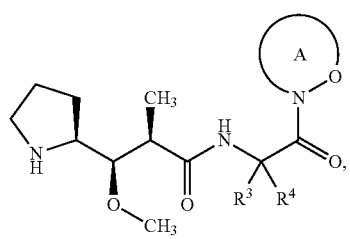

(VII)

in which $R^3$, $R^4$ and ring A have the meanings given above or a salt of this compound, likewise to give the compound of the formula (VI)

in which $R^2$, $R^3$, $R^4$, ring A and PG gave the meanings given above, and the respective resulting compound of the formula (VI) is then deprotected by customary methods of peptide chemistry to give a compound of the formula (I-B) according to the invention

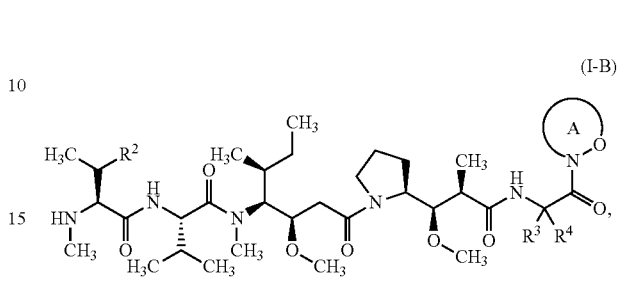

(I-B)

in which $R^2$, $R^3$, $R^4$ and ring A have the meanings given above, and this is subsequently, if desired, converted either (i) by base-induced alkylation with a compound of the formula (VIII)

$$R^{1A}—X$$

(VIII)

in which $R^{1A}$ has the meaning of $R^1$ given above, but does not represent hydrogen, and X represents a leaving group such as, for example, chloride, bromide, iodide, mesylate, triflate or tosylate, into a compound of the formula (I-C) according to the invention

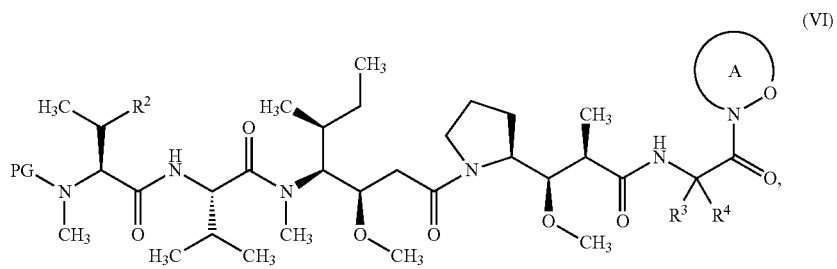

(VI)

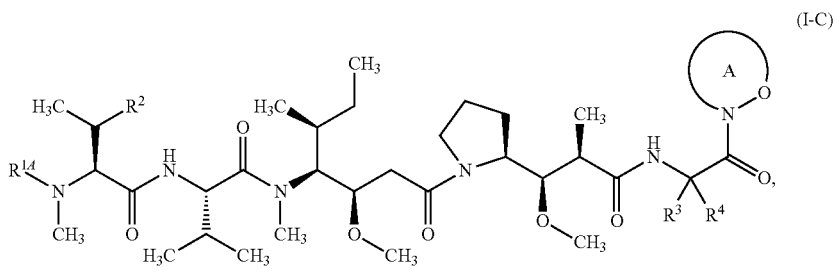

(I-C)

in which $R^{1A}$, $R^2$, $R^3$, $R^4$ and ring A have the meanings given above or (ii) by reaction with a compound of the formula (IX)

(IX)

in which $R^{1B}$ has the meaning of $R^{1A}$ given above, but with the alkyl chain length reduced by one $CH_2$ unit, in the presence of a suitable reducing agent into a compound of the formula (I-D)

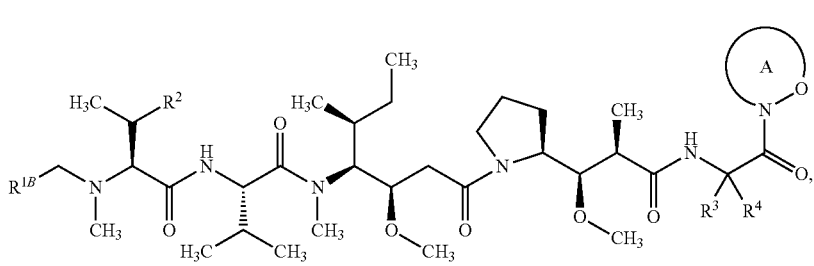

(I-D)

in which $R^{1B}$, $R^2$, $R^3$, $R^4$ and ring A have the meanings given above, and the compounds of the formulae (I-B), (I-C) and (I-D) obtained in this manner are optionally separated into their enantiomers and/or diastereomers and/or converted with the appropriate (i) solvents and/or (ii) bases or acids into their solvates, salts and/or solvates of the salts.

The coupling reactions described above (amide formation from the respective amine and carboxylic acid component) are carried out by generally customary methods of peptide chemistry [see, for example, M. Bodanszky, *Principles of Peptide Synthesis*, Springer-Verlag, Berlin, 1993; M. Bodanszky and A. Bodanszky, *The Practice of Peptide Synthesis*, Springer-Verlag, Berlin, 1984; H.-D. Jakubke and H. Jeschkeit, *Aminosaüren, Peptide, Proteine*, Verlag Chemie, Weinheim, 1982].

Inert solvents for the coupling reactions (II)+(III)→(IV), (IV)+(V)→(VI) and (II)+(VII)→(VI) are, for example, ethers such as diethyl ether, diisopropyl ether, tert-butyl methyl ether, tetrahydrofuran, 1,4-dioxane, 1,2-dimethoxyethane or bis-(2-methoxyethyl)ether, hydrocarbons such as benzene, toluene, xylene, pentane, hexane, heptane, cyclohexane or mineral oil fractions, halogenated hydrocarbons such as dichloromethane, trichloromethane, carbon tetrachloride, 1,2-dichloroethane, trichlorethylene or chlorobenzene, or dipolar aprotic solvents such as acetone, methyl ethyl ketone, acetonitrile, ethyl acetate, pyridine, dimethyl sulphoxide (DMSO), N,N-dimethylformamide (DMF), N,N-dimethylacetamide (DMA), N,N'-dimethylpropyleneurea (DMPU) or N-methylpyrrolidinone (NMP). It is also possible to use mixtures of such solvents. Preference is given to using N,N-dimethylformamide.

Suitable activating/condensing agents for these coupling reactions are, for example, carbodiimides such as N,N'-diethyl-, N,N'-dipropyl-, N,N'-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, phosphorus compounds such as propanephosphonic anhydride, diethyl cyanophosphonate, bis-(2-oxo-3-oxazolidinyl)phosphoryl chloride, benzotriazol-1-yloxytris(dimethylamino)phosphonium hexafluorophosphate or benzotriazol-1-yloxytris (pyrrolidino)phosphonium hexafluorophosphate (PyBOP), or uranium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluranium tetrafluoroborate (TPTU), O-(7-azabenzotriazol-1-yl)-N,N,N',N'-tetramethyluranium hexafluorophosphate (HATU) or O-(1H-6-chlorobenzotriazol-1-yl)-1,1,3,3-tetramethyluranium tetrafluoroborate (TCTU), if appropriate in combination with further auxiliaries such as 1-hydroxybenzotriazole (HOBt) or N-hydroxysuccinimide (HOSu), and suitable bases are alkali metal carbonates, for example sodium carbonate or potassium carbonate, or tertiary amine bases such as triethylamine, N-methylmorpholine, N-methylpiperidine, N,N-diisopropylethylamine, pyridine or 4-N,N-dimethylaminopyridine.

In the context of the present invention, an activating agent/condensing agent preferably used for such coupling reactions is N-(3-dimethylaminoisopropyl)-N'-ethylcarbodiimide hydrochloride (EDC) in combination with 1-hydroxybenzotriazole (HOBt) and N,N-diisopropylethylamine, or O-(7-azabenzotriazol-1-yl)-N,N,N',N'-tetramethyluranium hexafluorophosphate (HATU) likewise in combination with N,N-diisopropylethylamine.

The coupling reactions (II)+(III)→(IV), (IV)+(V)→(VI) and (II)+(VII)→(VI) are generally carried out in a temperature range of from −20° C. to +60° C., preferably at from 0° C. to +40° C. The reactions can be carried out at atmospheric, at elevated or at reduced pressure (for example from 0.5 to 5 bar); in general, the reactions are carried out at atmospheric pressure.

Suitable inert solvents for the reaction (I-B)+(VII)→(I-C) are, for example, ethers such as diethyl ether, diisopropyl ether, methyl tert-butyl ether, tetrahydrofuran, 1,4-dioxane, 1,2-dimethoxyethane or bis-(2-methoxyethyl)ether, hydrocarbons such as benzene, toluene, xylene, pentane, hexane, heptane, cyclohexane or mineral oil fractions, or dipolar aprotic solvents such as acetone, methyl ethyl ketone, acetonitrile, dimethyl sulphoxide (DMSO), N,N-dimethylformamide (DMF), N,N-dimethylacetamide (DMA), N,N'-dimethylpropyleneurea (DMPU), N-methylpyrrolidinone (NMP) or pyridine. It is also possible to use mixtures of such solvents. Preference is given to using N,N-dimethylformamide.

Suitable bases for this alkylation reaction are in particular alkali metal hydroxides such as, for example, lithium hydroxide, sodium hydroxide or potassium hydroxide, alkali metal or alkaline earth metal carbonates such as lithium carbonate, sodium carbonate, potassium carbonate, calcium carbonate or caesium carbonate, or customary organic amines such as triethylamine, N-methylmorpholine, N-methylpiperidine, N,N-diisopropylethylamine, pyridine or 4-N,N-dimethylaminopyridine. Preference is given to using potassium carbonate or caesium carbonate. If appropriate, the addition of an alkylation catalyst such as, for example, lithium bromide or lithium iodide, sodium iodide or potassium iodide, tetra-n-butylammonium bromide or tetra-n-butylammonium iodide or benzyltriethylammonium bromide is advantageous.

The reaction (I-B)+(VIII)→(I-C) is generally carried out in a temperature range of from −20° C. to +60° C., preferably at from 0° C. to +40° C. The reaction can be carried out at atmospheric, at elevated or at reduced pressure (for example from 0.5 to 5 bar); in general, the reaction is carried out at atmospheric pressure.

The reaction (I-B)+(IX)→(I-D) is carried out in solvents which are customary for a reductive amination and inert under the reaction conditions, if appropriate in the presence of an acid and/or a dehydrating agent as catalyst. Such solvents include, for example, alcohols such as methanol, ethanol, n-propanol, isopropanol, n-butanol or tert-butanol, ethers such as tetrahydrofuran, 1,4-dioxane, 1,2-dimethoxyethane or bis-(2-methoxyethyl)ether, or other solvents such as dichloromethane, 1,2-dichloroethane, N,N-dimethylformamide or else water. It is also possible to use mixtures of these solvents. Preferably, the solvent used is a 1,4-dioxane/water mixture with addition of acetic acid or dilute hydrochloric acid as catalyst.

Suitable reducing agents for this reaction are in particular complex borohydrides such as, for example, sodium borohydride, sodium cyanoborohydride, sodium triacetoxyborohydride or tetra-n-butylammonium borhydride. Preference is given to using sodium cyanoborohydride.

The reaction (I-B)+(IX)→(I-D) is generally carried out in a temperature range of from 0° C. to +120° C., preferably at from +50° C. to +100° C. The reaction can be carried out at atmospheric, at elevated or at reduced pressure (for example from 0.5 to 5 bar); in general, the reaction is carried out at atmospheric pressure.

Any functional groups present in the radicals $R^1$, $R^{1A}$, $R^{1B}$, $R^2$, $R^4$, $R^5$ and/or $R^6$—such as amino, hydroxyl and carboxyl groups in particular — may also be present in a temporarily protected form during the above-described process steps, if useful or necessary. In these cases, such protective groups are introduced and removed in accordance with customary methods known from peptide chemistry [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. Where two or more protected groups are present, they can be liberated again optionally simultaneously in a one-pot reaction, or else liberated again in separate reaction steps.

As an amino-protective group it is preferred to use tert-butoxycarbonyl (Boc), benzyloxycarbonyl (Z) or (9H-fluoren-9-ylmethoxy)carbonyl (Fmoc); for a hydroxyl or carboxyl function it is preferred to use tert-butyl or benzyl as protective group. The removal of a tert-butyl or tert-butoxycarbonyl group is typically accomplished by treatment with a strong acid, such as hydrogen chloride, hydrogen bromide or trifluoroacetic acid, in an inert solvent such as diethyl ether, 1,4-dioxane, dichloromethane or acetic acid; this reaction may optionally also be carried out without addition of an inert solvent. In the case of benzyl or benzyloxycarbonyl as protective group, this group is removed preferably by hydrogenolysis in the presence of a suitable palladium catalyst, such as palladium on activated carbon, for example. The (9H-fluoren-9-ylmethoxy)carbonyl group is generally removed using a secondary amine base such as diethylamine or piperidine.

The compounds of the formula (II) can be prepared by customary methods of peptide chemistry, for example by first coupling N-(benzyloxycarbonyl)-L-valine of the formula (X)

(X)

in which Z represents the benzyloxycarbonyl protective group
with the aid of a condensing agent with a compound of the formula (XI)

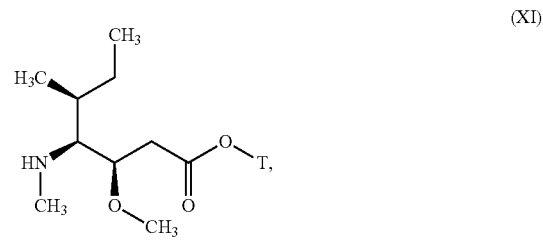

(XI)

in which T represents $(C_1-C_4)$-alkyl
or a salt of this compound to give a compound of the formula (XII)

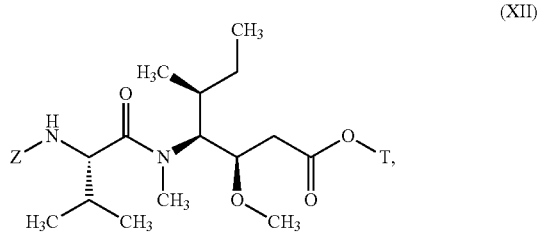

in which T and Z have the meanings given above,
then, after hydrogenolytic removal of the Z protective group, coupling this compound in the presence of a condensing agent with N-protected N-methyl-L-valine or N-methyl-L-threonine of the formula (XIII)

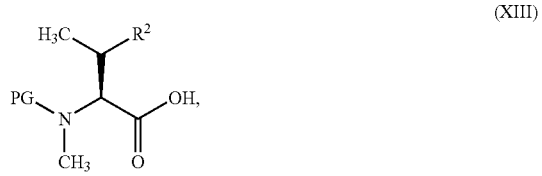

in which $R^2$ has the meaning given above
and
PG represents an amino protective group such as, for example, (9H-fluoren-9-ylmethoxy)-carbonyl, tert-butoxycarbonyl or benzyloxycarbonyl,
to give a compound of the formula (XIV)

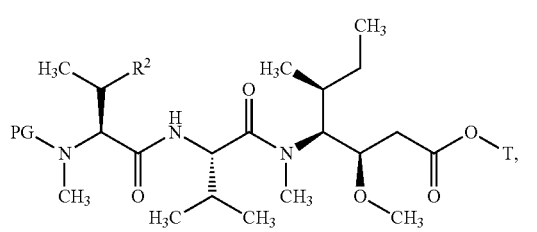

in which $R^2$, PG and T have the meanings given above,
and finally converting the ester grouping —C(O)OT in (XIV) by customary methods into the free carboxylic acid.

The coupling reactions (X)+(XI)→(XII) and Z-deprotected (XII)+(XIII)→(XIV) are carried out under reaction conditions analogous to those described above in the coupling steps of processes [A] and [B].

The hydrolysis of the ester group —C(O)OT in process step (XIV)→(II) is carried out by customary methods by treating the ester in an inert solvent with an acid or a base, where in the latter variant the carboxylate salt initially formed is converted into the free carboxylic acid by subsequent addition of an acid. In the case of a tert-butyl ester, the cleavage is preferably carried out using an acid.

Here, the alkyl radical T in compound (XI) is chosen such that the conditions of its removal are compatible with the respective protective group PG in compound (XIII).

Suitable bases for the ester hydrolysis are the customary inorganic bases. These include in particular alkali metal or alkaline earth metal hydroxides such as, for example, lithium hydroxide, sodium hydroxide, potassium hydroxide or barium hydroxide, or alkali metal or alkaline earth metal carbonates such as sodium carbonate, potassium carbonate or calcium carbonate. Preference is given to lithium hydroxide, sodium hydroxide or potassium hydroxide.

Suitable acids for the ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid or mixtures thereof, if appropriate with addition of water. Preference is given to hydrogen chloride or trifluoroacetic acid in the case of a tert-butyl ester and hydrochloric acid for a methyl ester.

Inert solvents suitable for these reactions are water or the organic solvents customary for an ester cleavage. These preferably include lower alcohols such as methanol, ethanol, n-propanol or isopropanol, ethers such as diethyl ether, tetrahydrofuran, 1,4-dioxane or 1,2-dimethoxyethane, or other solvents such as dichloromethane, acetone, methyl ethyl ketone, N,N-dimethylformamide or dimethyl sulphoxide. It is also possible to use mixtures of these solvents. In the case of a basic ester hydrolysis, preference is given to using mixtures of water with 1,4-dioxane, tetrahydrofuran, methanol, ethanol and/or dimethylformamide. In the case of a reaction with trifluoroacetic acid, preference is given to using dichloromethane, and in the case of a reaction with hydrogen chloride, preference is given to using tetrahydrofuran, diethyl ether, 1,4-dioxane or water.

The ester cleavage is generally carried out in a temperature range of from −20° C. to +100° C., preferably at from 0° C. to +50° C.

The compounds of the formula (V) can be prepared analogously to known processes for example by coupling a protected amino acid of the formula (XV)

in which $R^3$ and $R^4$ have the meanings given above and Boc represents the tert-butoxycarbonyl protective group
with activation of the carboxyl function either
[C] with a compound of the formula (XVI)

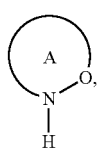

in which ring A has the meaning given above,
or a salt of this compound to give a compound of the formula (XVII)

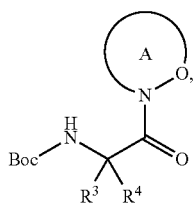

(XVII)

in which R³, R⁴, ring A and Boc have the meanings given above, or

[D] first coupling with hydroxylamine or a salt thereof to give a compound of the formula (XVIII)

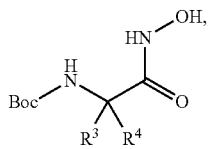

(XVIII)

in which R³, R⁴ and Boc have the meanings given above and then alkylating this compound in the presence of a base with a dibromide of the formula (XIX)

(XIX)

in which the linking group A' corresponds to the other optionally substituted elements of the above-defined ring A—except for the N—O grouping, with cyclization, likewise giving the compound of the formula (XVII)

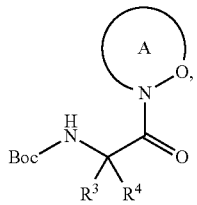

(XVII)

in which R³, R⁴, ring A and Boc have the meanings given above and then removing the Boc protective group in (XVII) in a customary manner by treatment with an acid.

The coupling reactions (XV)+(XVI)→(XVII) and (XV)+hydroxylamine→(XVIII) are carried out under reaction conditions analogous to those described above in the coupling steps of processes [A] and [B].

The bases used for the cycloalkylation in the process step (XVIII)+(XIX)→(XVII) are preferably alkali metal hydroxides such as, for example, lithium hydroxide, sodium hydroxide or potassium hydroxide, or alkali metal or alkaline earth metal carbonates such as lithium carbonate, sodium carbonate, potassium carbonate, calcium carbonate or caesium carbonate.

Suitable inert solvents for this reaction are in particular alcohols such as methanol, ethanol, n-propanol, isopropanol, n-butanol or tert-butanol, or dipolar aprotic solvents such as acetone, methyl ethyl ketone, N,N-dimethylformamide or dimethyl sulphoxide. Preference is given to using acetone.

The reaction (XVIII)+(XIX)→(XVII) is generally carried out in a temperature range of from +20° C. to +120° C., preferably at from +50° C. to +80° C. The reaction can be carried out at atmospheric, at elevated or at reduced pressure (for example from 0.5 to 5 bar); in general, the reaction is carried out at atmospheric pressure.

For their part, the compounds of the formula (VII) can be obtained by coupling the compound (V) described above with the compound (XX)

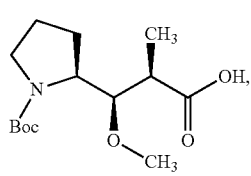

(XX)

in which Boc represents the tert-butoxycarbonyl protective group to give a compound of the formula (XXI)

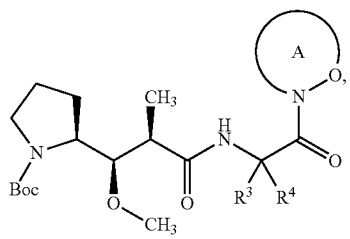

(XXI)

in which R³, R⁴, ring A and Boc have the meanings given above, and subsequent removal of the Boc protective group. For its part, the compound (XX) can be obtained from the compound (III) by introducing an appropriate protective group.

The coupling reaction (V)+(XX)→(XXI) is again carried out under conditions analogous to those described above in the coupling steps of processes [A] and [B].

The compounds of the formulae (III), (VIII), (IX), (X), (XI), (XIII), (XV), (XVI) and (XIX), including, where appropriate, chiral or diastereomeric forms thereof, are available commercially or are described as such in the literature, or they can be prepared by routes that are obvious to the skilled person, in analogy to methods published in the literature. Numerous comprehensive instructions and also literature information on the preparation of the starting materials are also given in the experimental section, in the section relating to the preparation of the starting compounds and intermediates.

If appropriate isomerically pure starting materials are not available, separation of the compounds according to the invention into the corresponding enantiomers and/or diastereomers can expediently also be carried out as early as at the stage of the compounds (V), (VI), (VII), (XV), (XVI), (XVII), (XVIII) or (XXI), which are then reacted further in separated form according to the reaction steps described above. Such a separation of the stereoisomers can be effected by customary methods known to the person skilled in the art. Preference is given to using chromatographic processes on achiral or chiral separation phases; in the case of free carboxylic acids as intermediates, there may alternatively also be separation via diastereomeric salts with the aid of chiral bases.

The preparation of the compounds according to the invention can be illustrated in an exemplary manner by the reaction schemes below:

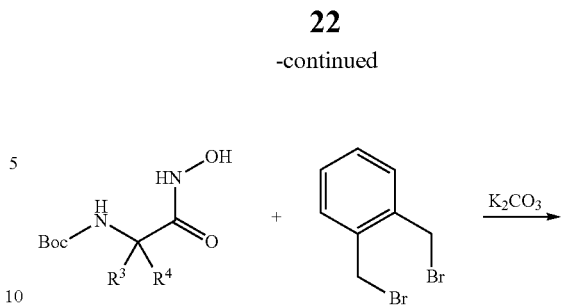

Scheme 1

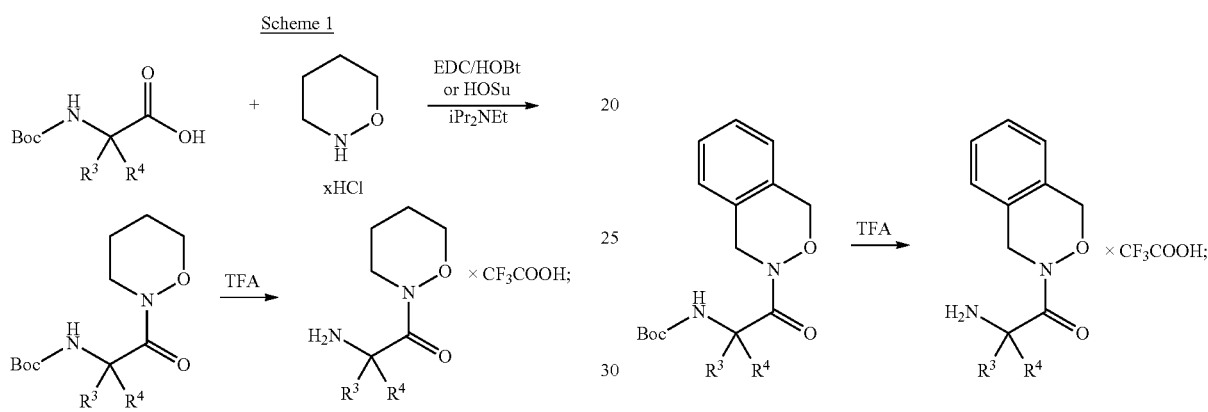

Scheme 2

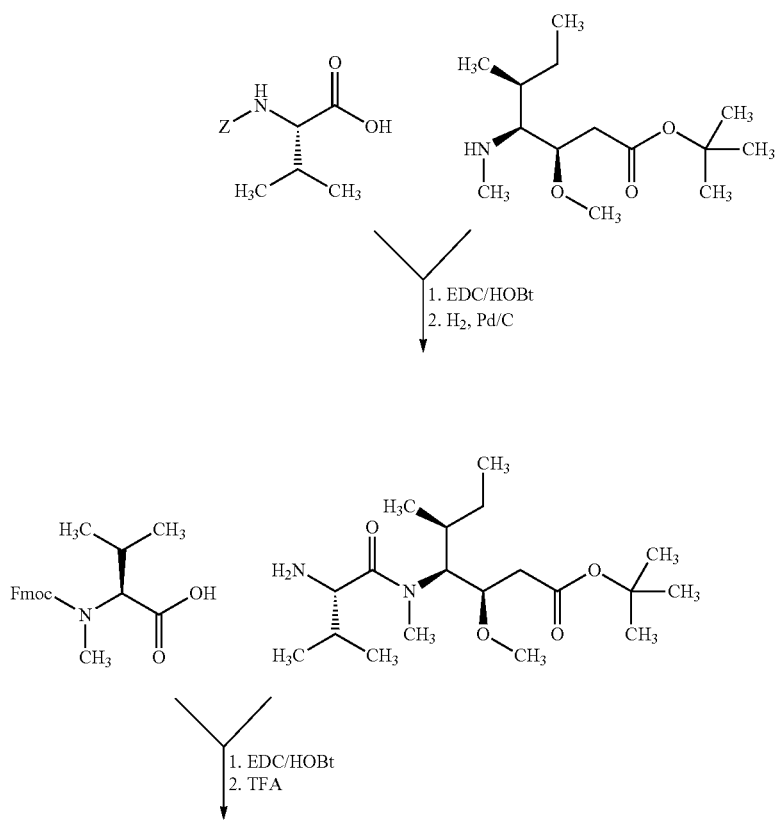

-continued
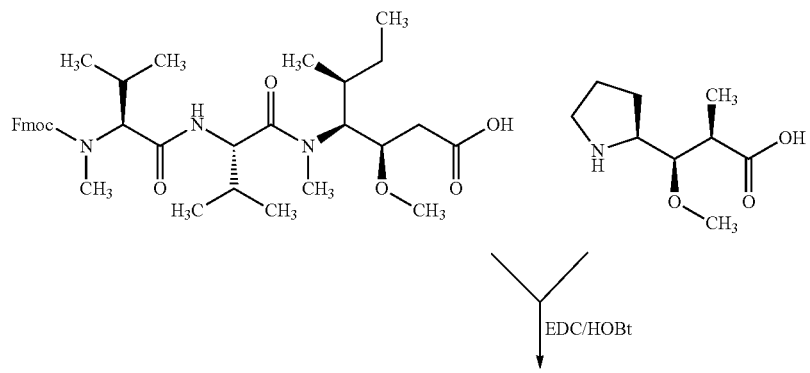
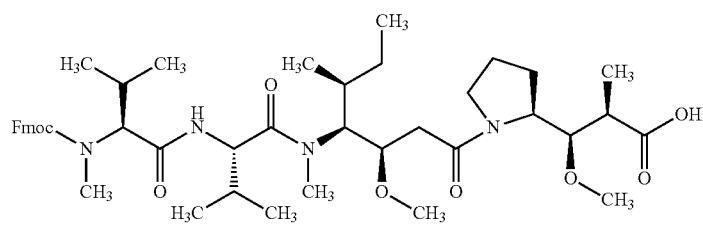
Scheme 3
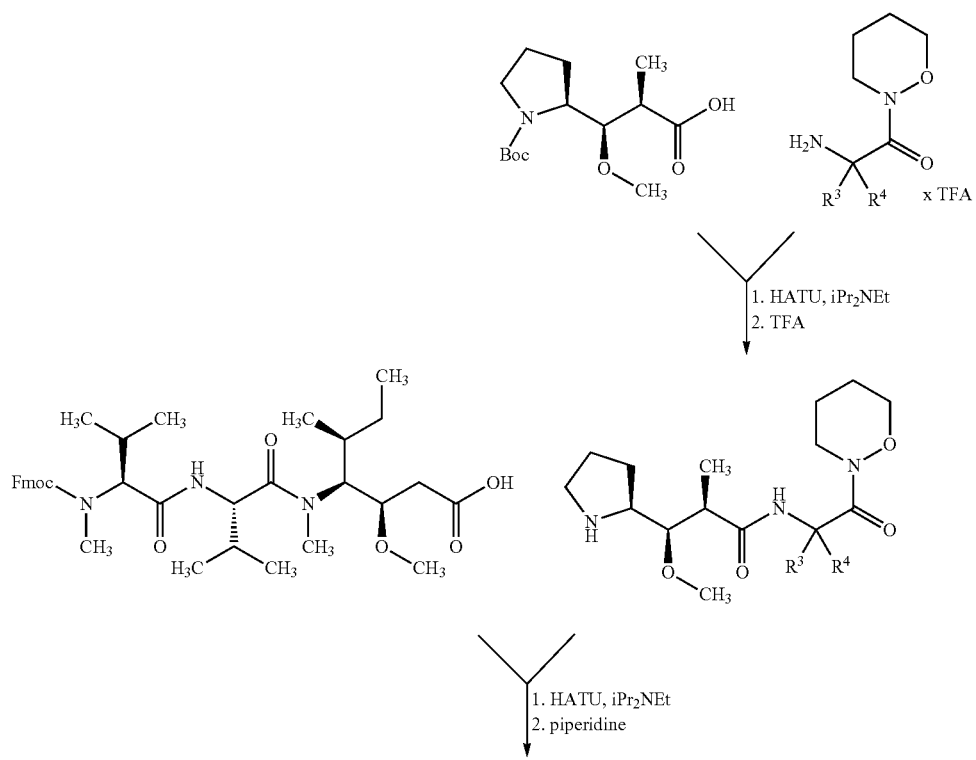

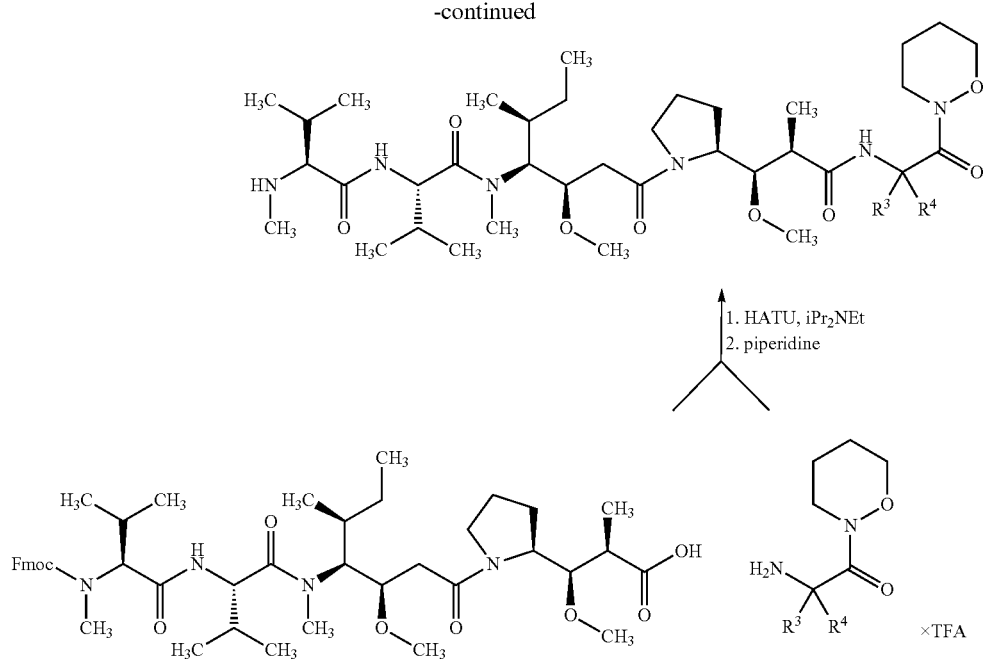
Scheme 4
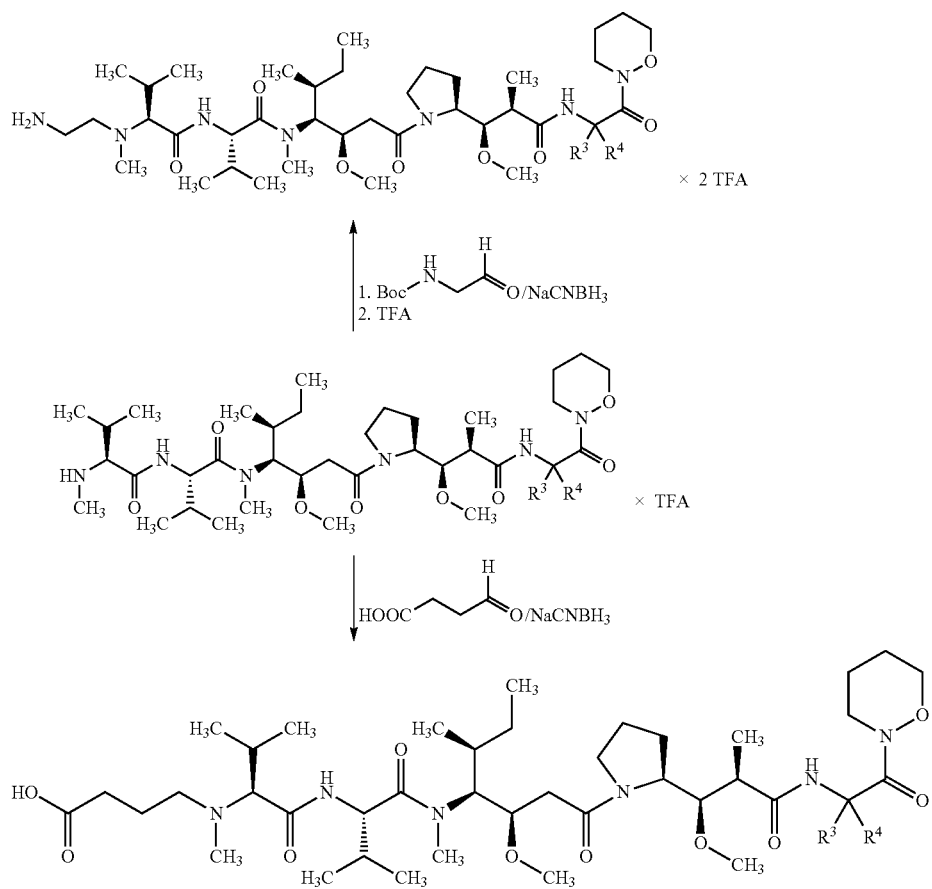

The compounds according to the invention have useful pharmacological properties and can be used for the prevention and treatment of disorders in humans and animals.

Compared to monomethylauristatin F (MMAF), the compounds according to the invention have considerably stronger cytotoxic activity and moreover, compared to known ester derivatives of MMAF, such as MMAF-OMe, have a significantly higher stability in plasma. On the basis of this profile of properties, the compounds according to the invention are therefore suitable to a particular degree for the treatment of hyperproliferative diseases in humans and in mammals generally. The compounds are able on the one hand to inhibit, block, reduce or lower cell proliferation and cell division, and on the other hand to increase apoptosis.

The hyperproliferative disorders for the treatment of which the compounds according to the invention can be employed include in particular the group of cancer and tumour diseases. In the context of the present invention, these are understood as meaning, in particular, the following disorders, but without being limited to them: mammary carcinomas and mammary tumours (ductal and lobular forms, also in situ), tumours of the respiratory tract (parvicellular and non-parvicellular carcinoma, bronchial carcinoma), cerebral tumours (e.g. of the brain stem and of the hypothalamus, astrocytoma, medulloblastoma, ependymoma and neuro-ectodermal and pineal tumours), tumours of the digestive organs (oesophagus, stomach, gall bladder, small intestine, large intestine, rectum), liver tumours (including hepatocellular carcinoma, cholangiocellular carcinoma and mixed hepatocellular and cholangiocellular carcinoma), tumours of the head and neck region (larynx, hypopharynx, nasopharynx, oropharynx, lips and oral cavity), skin tumours (squamous epithelial carcinoma, Kaposi sarcoma, malignant melanoma, Merkel cell skin cancer and non-melanomatous skin cancer), tumours of soft tissue (including soft tissue sarcomas, osteosarcomas, malignant fibrous histiocytomas, lymphosarcomas and rhabdomyosarcomas), tumours of the eyes (including intraocular melanoma and retinoblastoma), tumours of the endocrine and exocrine glands (e.g. thyroid and parathyroid glands, pancreas and salivary gland), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testicles in men). These also include proliferative blood disorders in solid form and as circulating blood cells, such as lymphomas, leukaemias and myeloproliferative diseases, e.g. acute myeloid, acute lymphoblastic, chronic lymphocytic, chronic myelogenic and hair cell leukaemia, and also AIDS-correlated lymphomas, Hodgkin's lymphomas, non-Hodgkin's lymphomas, cutaneous T-cell lymphomas, Burkitt's lymphomas and lymphomas in the central nervous system.

These well-described diseases in humans can also occur with a comparable aetiology in other mammals and can be treated there with the compounds of the present invention.

In the context of this invention the term "treatment" or "treat" is used in the conventional sense and means attending to, caring for and nursing a patient with the aim of combating, reducing, attenuating or alleviating a disease or health abnormality and improving the living conditions impaired by this disease, such as, for example, with a cancerous disorder.

The present invention furthermore provides the use of the compounds according to the invention for the treatment and/or prevention of disorders, in particular the disorders mentioned above.

The present invention furthermore provides the use of the compounds according to the invention for the preparation of a medicament for the treatment and/or prevention of disorders, in particular the disorders mentioned above.

The present invention furthermore provides the use of the compounds according to the invention in a method for the treatment and/or prevention of diseases, in particular the above-mentioned diseases.

The present invention furthermore provides a method for the treatment and/or prevention of disorders, in particular the disorders mentioned above, using an effective amount of at least one of the compounds according to the invention.

The compounds according to the invention can be employed by themselves or, if required, in combination with one or more other pharmacologically active substances, as long as this combination does not lead to unwanted and unacceptable side effects. The present invention furthermore therefore provides medicaments comprising at least one of the compounds according to the invention and one or more further drugs, in particular for the treatment and/or prevention of the abovementioned disorders.

For example, the compounds of the present invention can be combined with known antihyperproliferative, cytostatic or cytotoxic substances for the treatment of cancerous disorders. Suitable drugs in the combination which may be mentioned by way of example are as follows:
aldesleukin, alendronic acid, alfaferone, alitretinoin, allopurinol, aloprim, ALOXI (palonosetron), altretamine, aminoglutethimide, amifostine, amrubicin, amsacrine, anastrozole, anzmet, ARANESP (darbepoeitin alfa), arglabin, arsenic trioxide, aromasin, 5-azacytidine, azathioprine, BCG or tice-BCG, bestatin, betamethasone acetate, betamethasone sodium phosphate, bexarotene, bleomycin sulphate, broxuridine, bortezomib, busulfan, calcitonin, CAMPATH (alemtuzumab), capecitabine, carboplatin, CASODEX (bicalutamide), cefesone, celmoleukin, cerubidin, chlorambucil, cisplatin, cladribin, clodronic acid, cyclophosphamide, cytarabine, dacarbazine, dactinomycin, DAUNOXOME (danorubicin), DECADRON (dexamethasone), DECADRON (dexamethasone) phosphate, delestrogen, denileukin diftitox, depomedrol, deslorelin, dexrazoxane, diethylstilbestrol, DIFLUCAN (fluconazole), docetaxel, doxifluridine, doxorubicin, dronabinol, DW-166HC, ELIGARD (leuprolide), ELITEK (rasburicase), ELLENCE (epirubicin), EMEND (aprepitant), epirubicin, epoetin-alfa, EPOGEN (epoetin alfa), eptaplatin, ergamisol, ESTRACE (estradiol), estradiol, estramustine sodium phosphate, ethinylestradiol, ETHYOL (amifostine), etidronic acid, ETOPOPHOS (etoposide), etoposide, fadrozole, farstone, filgrastim, finasteride, fligrastim, floxuridine, fluconazole, fludarabin, 5-fluorodeoxyuridine monophosphate,5 -fluorouracil (5-FU), fluoxymesterone, flutamide, formestane, fosteabine, fotemustine, fulvestrant, GAMMAGARD (immune globulin infusion (human)), gemcitabine, gemtuzumab, GLEEVEC (imatinib), GLIADEL (carmustine), goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon- alpha-2α, interferon-alpha-2β, interferon-alpha-n1, interferon-alpha-n 3, interferon-beta, interferon-gamma-lα, interleukin-2, intronA, iressa, irinotecan, kytril, lentinan sulphate, letrozole, leucovorin, leuprolide, leuprolide acetate, levamisole, levofolic acid calcium salt, levothroid, levoxyl, lomustine, lonidamine, MARINOL (dronabinol), mechlorethamine, mecobalamin, medroxyprogesterone acetate, megestrol acetate, melphalan, MENEST (esterified estrogen), 6-mercaptopurine, mesna, methotrexate, METVIX (methyl aminolevulinate), miltefosine, minocycline, mitomycin C, mitotane, mitoxantrone, MODRENAL (trilostane), MYOCET (non-pegylated liposomal doxorubicin), nedaplatin, NEULASTA (pegfilgrastim), NEUMEGA (oprelvekin), NEUPOGEN (filgrastim), nilutamide, NOVALDEX (tamoxifen), NSC-631570, OCT-43, octreotide, ondansetron hydrochloride, ORAPRED (prednisolone), oxaliplatin, paclitaxel, PEDIAPRED (prednisolone), pegaspargase, PEGASYS (peginterfereon alfa-2a), pentostatin, PICIBANIL, pilocarpine hydrochloride, pirarubicin, plicamycin, porfimer sodium, prednimustine, prednisolone, prednisone, PREMARIN (conjugated estrogens), procarbazine, PROCRIT (epoetin alfa), raltitrexed, REBIF (interferon beta-1 a), rhenium-186 etidronate, rituximab, roferon-A, romurtide, SALAGEN (pilocarpine), sandostatin, sargramostim, semustine, sizofiran, sobuzoxane, SOLU-MEDROL (methylprednisolone), streptozocin, strontium-89 chloride, SYNTHROID (levothyroxine), tamoxifen, tamsulosin, tasonermin, tastolactone, taxoter, teceleukin, temozolomide, teniposide, testosterone propionate, TESTRED (methyltestosterone), thioguanine, thiotepa, thyrotropin, tiludronic acid, topotecan, toremifen, tositumomab, tastuzumab, teosulfan, tretinoin, TREXALL (methotrexate), trimethylmelamine, trimetrexate, triptorelin acetate, triptorelin pamoate, UFT, uridine, valrubicin, vesnarinone, vinblastine, vincristine, vindesine, vinorelbine, VIRULIZIN (LOR-253), ZINECARD (dexrazoxane), zinostatin-stimalamer, ZOFRAN (ondansetron); ABI-007, acolbifen, ACTIMMUNE (interferon gamma-1b), AFFINITAK, aminopterin, arzoxifen, asoprisnil, atamestane, atrasentan, avastin, BAY 43-9006 (sorafenib), CCI-779, CDC-501, CELEBREX (celecoxib), cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet hemocyanine, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, OSIDEM, paclitaxel polyglutamate, pamidronate disodium, PN-401, QS-21, quazepam, R-1549, raloxifen, ranpirnas, 13-cis-retic acid, satraplatin, seocalcitol, T-138067, TARCEVA (erlotinib), taxoprexin, thymosin-alpha-1, tiazofurin, tipifarnib, tirapazamine, TLK-286, toremifen, transMID-107R, valspodar, vapreotide, vatalanib, verteporfin, vinflunin, Z-100, zoledronic acid and combinations of these.

In a preferred embodiment, the compounds of the present invention can be combined with antihyperproliferative agents, which can be, by way of example—without this list being conclusive—as follows:
aminoglutethimide, L-asparaginase, azathioprine, 5-azacytidine, bleomycin, busulfan, carboplatin, carmustine, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and its derivatives, erythrohydroxynonyladenin, ethinylestradiol, etoposide, fludarabin phosphate, 5-fluorodeoxyuridine, 5-fluorodeoxyuridine monophosphate, 5-fluorouracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, N-phosphonoacetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine and vinorelbine.

The compounds of the invention can also be combined in a very promising manner with biological therapeutics such as antibodies (e.g. avastin, rituxan, erbitux, herceptin). The compounds of the invention can also achieve positive effects in combination with therapies directed against angiogenesis, such as, for example, with avastin, axitinib, recentin, regorafenib, sorafenib or sunitinib. Combinations with inhibitors of the proteasome and of mTOR and also with antihormones and steroidal metabolic enzyme inhibitors are likewise particularly suitable because of their favourable profile of side effects.

Generally, the following aims can be pursued with the combination of compounds of the present invention with other agents having a cytostatic or cytotoxic action:
an improved activity in slowing down the growth of a tumour, in reducing its size or even in its complete elimination compared with treatment with an individual drug;
the possibility of employing the chemotherapeutics used in a lower dosage than in monotherapy;
the possibility of a more tolerable therapy with few side effects compared with individual administration;
the possibility of treatment of a broader spectrum of tumour diseases;
the achievement of a higher rate of response to the therapy;
a longer survival time of the patient compared with present-day standard therapy.

The compounds according to the invention can moreover also be employed in combination with radiotherapy and/or surgical intervention.

The present invention furthermore provides medicaments which comprise at least one compound according to the invention, conventionally together with one or more inert, non-toxic, pharmaceutically suitable excipients, and the use thereof for the abovementioned purposes.

The compounds of the invention can act systemically and/or locally. They can be administered in a suitable manner for this purpose, such as for example orally, parenterally, pulmonally, nasally, sublingually, lingually, buccally, rectally, dermally, transdermally, conjunctivally, otically or as an implant or stent.

The compounds according to the invention can be administered in suitable administration forms for these administration routes.

Administration forms which function according to the prior art, release the compounds of the invention rapidly and/or in a modified manner and contain the compounds of the invention in crystalline and/or amorphized and/or dissolved form are suitable for oral administration, such as e.g. tablets (non-coated or coated tablets, for example with coatings which are resistant to gastric juice or dissolve in a delayed manner or are insoluble and control the release of the compound of the invention), films/oblates or tablets, which disintegrate rapidly in the oral cavity, films/lyophilizates, capsules (for example hard or soft gelatine capsules), film-coated tablets, granules, pellets, powders, emulsions, suspensions, aerosols or solutions.

Parenteral administration can be effected with bypassing of an absorption step (e.g. intravenously, intraarterially, intracardially, intraspinally or intralumbally) or with inclusion of an absorption (e.g. intramuscularly, subcutaneously, intracutaneously, percutaneously or intraperitoneally). Administration forms which are suitable for parenteral administration include injection and infusion formulations in the form of solutions, suspensions, emulsions, lyophilizates or sterile powders.

For the other administration routes, e.g. inhalation medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents are suitable.

Oral and parenteral administration are preferred, in particular oral and intravenous administration.

The compounds according to the invention can be converted into the administration forms mentioned. This can be effected in a manner known per se by mixing with inert, non-toxic, pharmaceutically suitable excipients. These excipients include inter alia carrier substances (for example microcrystalline cellulose, lactose, mannitol), solvents (e.g. liquid polyethylene glycols), emulsifiers and dispersing or wetting agents (for example sodium dodecyl sulphate, polyoxysorbitan oleate), binders (for example polyvinylpyrrolidone), synthetic and natural polymers (for example albumin), stabilizers (e.g. antioxidants, such as, for example, ascorbic acid), colorants (e.g. inorganic pigments, such as, for example, iron oxides) and taste and/or odour correctants.

In general, it has proved advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, and in particular depending on the body weight, administration route, individual behaviour towards the active compound, nature of the formulation and point of time or interval at which administration takes place. Thus in some cases it may be sufficient to manage with less than the above-mentioned minimum amount, while in other cases the upper limit mentioned must be exceeded. In the case where relatively large amounts are administered, it may be advisable to distribute these into several individual doses over the day.

The following working examples illustrate the invention. The invention is not limited to the examples.

The percentage figures in the following tests and examples are percentages by weight, unless stated otherwise; parts are parts by weight. Solvent ratios, dilution ratios and concentration data of liquid/liquid solutions in each case relate to the volume.

A. Examples

| Abbreviations and acronyms: | |
|---|---|
| abs. | absolute |
| Ac | acetyl |
| aq. | aqueous, aqueous solution |
| Boc | tert-butoxycarbonyl |
| br. | broad (in NMR) |
| Ex. | example |
| CI | chemical ionization (in MS) |
| d | doublet (in NMR) |
| d | day(s) |

-continued

| Abbreviations and acronyms: | |
|---|---|
| TLC | thin-layer chromatography |
| DCI | direct chemical ionization (in MS) |
| dd | doublet of a doublet (in NMR) |
| DMAP | 4-N,N-dimethylaminopyridine |
| DME | 1,2-dimethoxyethane |
| DMF | N,N-dimethylformamide |
| DMSO | dimethyl sulphoxide |
| DPBS | Dulbecco's phosphate-buffered saline solution |
| dt | doublet of a triplet (in NMR) |
| EDC | N'-(3-dimethylaminopropyl)-N-ethylcarbodiimide hydrochloride |
| EI | electron impact ionization (in MS) |
| eq. | equivalent(s) |
| ESI | electrospray ionization (in MS) |
| FCS | foetal calf serum |
| Fmoc | (9H-fluoren-9-ylmethoxy)carbonyl |
| sat. | saturated |
| GTP | guanosine 5'-triphosphate |
| h | hour(s) |
| HATU | O-(7-azabenzotriazol-1-yl)-N,N,N',N'-tetramethyluronium hexafluorophosphate |
| HEPES | 4-(2-hydroxyethyl)piperazine-1-ethanesulphonic acid |
| HOAc | acetic acid |
| HOBt | 1-hydroxy-1H-benzotriazole hydrate |
| HOSu | N-hydroxysuccinimide |
| HPLC | high-pressure, high-performance liquid chromatography |
| conc. | concentrated |
| LC-MS | liquid chromatography-coupled mass spectrometry |
| m | multiplet (in NMR) |
| min | minute(s) |
| MS | mass spectrometry |
| MTT | 3-(4,5-dimethylthiazol-2-yl)-2,5-diphenyl-2H-tetrazolium bromide |
| NMM | N-methylmorpholine |
| NMP | N-methyl-2-pyrrolidinone |
| NMR | nuclear magnetic resonance spectrometry |
| PBS | phosphate-buffered saline solution |
| Pd/C | palladium on activated carbon |
| quant. | quantitative (for yield) |
| quart | quartet (in NMR) |
| quint | quintet (in NMR) |
| $R_f$ | retention index (for TLC) |
| RT | room temperature |
| $R_t$ | retention time (for HPLC) |
| s | singlet (in NMR) |
| t | triplet (in NMR) |
| tert | tertiary |
| TFA | trifluoroacetic acid |
| THF | tetrahydrofuran |
| UV | ultraviolet spectrometry |
| v/v | volume to volume ratio (of a solution) |
| Z | benzyloxycarbonyl |
| tog. | together |

HPLC and LC-MS Methods:

Method 1 (LC-MS):

Instrument: Waters Acquity SQD UPLC System; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.

Method 2 (LC-MS):

Instrument: Micromass QuattroPremier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 3 (LC-MS):

Instrument: Micromass Quattro Micro MS with HPLC Agilent Serie 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 4 (LC-MS):

MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 5 (HPLC):

Instrument: HP 1090 Serie II; column: Merck Chromolith SpeedROD RP-18e, 50 mm×4.6 mm; precolumn: Merck Chromolith Guard Cartridge Kit RP-18e, 5 mm×4.6 mm; injection volume: 5 μl; mobile phase A: 70% HClO$_4$ in water (4 ml/liter), mobile phase B: acetonitrile; gradient: 0.00 min 20% B→0.50 min 20% B→3.00 min 90% B→3.50 min 90% B→3.51 min 20% B→4.00 min 20% B; flow rate: 5 ml/min; column temperature: 40° C.

Method 6 (HPLC):

Instrument: Waters 2695 with DAD 996; column: Merck Chromolith SpeedROD RP-18e, 50 mm×4.6 mm; precolumn: Merck Chromolith Guard Cartridge Kit RP-18e, 5 mm×4.6 mm; mobile phase A: 70% HClO$_4$ in water (4 ml/liter), mobile phase B: acetonitrile; gradient: 0.00 min 5% B→0.50 min 5% B→3.00 min 95% B→4.00 min 95% B; flow rate: 5 ml/min.

Method 7 (LC-MS):

MS instrument type: Waters ZQ; HPLC instrument type: Agilent 1100 Series; UV DAD; column: Thermo Hypersil GOLD 3μ20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.

Method 8 (LC-MS):

MS instrument type: Waters ZQ; HPLC instrument type: Agilent 1100 Series; UV DAD; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→2.0 min 60% A→2.3 min 40% A→3.0 min 20% A→4.0 min 10% A→4.2 min 100% A (flow rate 2.5 ml/min); oven: 55° C.; flow rate: 2 ml/min; UV detection: 210 nm.

Method 9 (LC-MS):

Instrument: Waters Acquity SQD UPLC System; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

For all reactants or reagents whose preparation is not explicitly described below, they were obtained commercially from generally available sources. For all other reactants or reagents whose preparation is likewise not described below, and which were not available commercially or were obtained from sources which are not generally available, a reference is given to the published literature in which their preparation is described.

Starting Materials and Intermediates

Starting Material 1

(2R,3R)-3-[(2S)-1-(tert-Butoxycarbonyl)pyrrolidin-2-yl]-3-methoxy-2-methylpropanoic acid (Boc-dolaproine)

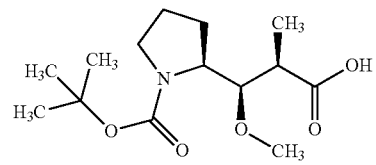 [SMILES: CO[C@H]([C@@H](C)C(=O)O)[C@@H]1CCCN1C(=O)OC(C)(C)C]

The title compound can be prepared by various routes in accordance with literature procedures, see, for example, Pettit et al., *Synthesis* 1996, 719; Shioiri et al., *Tetrahedron Lett.* 1991, 32, 931; Shioiri et al., *Tetrahedron* 1993, 49, 1913; Koga et al., *Tetrahedron Lett.* 1991, 32, 2395; Vidal et al., *Tetrahedron* 2004, 60, 9715; Poncet et al., *Tetrahedron* 1994, 50, 5345. Here, it was prepared either as free acid (as shown) or in the form of the corresponding dicyclohexylamine salt.

Starting Material 2 tert-Butyl (3R,4S,5S)-3-methoxy-5-methyl-4-(methylamino)heptanoate hydrochloride (dolaisoleucine-OtBu×HCl)

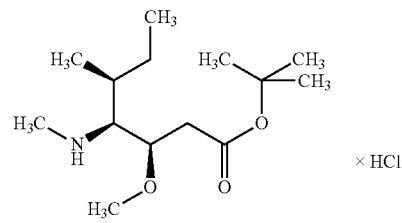 [SMILES: CC[C@H](C)[C@H](NC)[C@@H](CC(=O)OC(C)(C)C)OC]

The title compound can be prepared by various routes in accordance with literature procedures, see, for example, Pettit et al., *J. Org. Chem.* 1994, 59, 1796; Koga et al., *Tetrahedron Lett.* 1991, 32, 2395; Shioiri et al., *Tetrahedron Lett.* 1991, 32, 931; Shioiri et al., *Tetrahedron* 1993, 49, 1913.

Starting Material 3

N$^{\alpha}$-(tert-Butoxycarbonyl)-N-hydroxy-L-phenylalaninamide

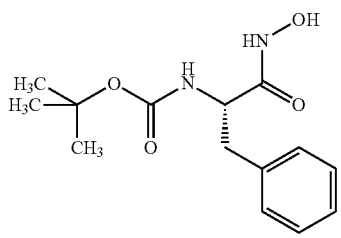 [SMILES: CC(C)(C)OC(=O)N[C@@H](Cc1ccccc1)C(=O)NO]

The title compound was prepared according to literature procedures (A. Ritter et al., *J. Org. Chem.* 1994, 59, 4602).
Yield: 750 mg (75% of theory)
LC-MS (Method 3): R$_t$=1.67 min; MS (ESIpos): m/z=281 (M+H)$^+$.

Starting Material 4

1,2-Oxazolidine hydrochloride

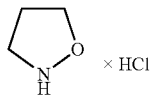

The title compound can be prepared according to literature procedures, see, for example, H. King, *J. Chem. Soc.* 1942, 432; it is also commercially available.

Starting Material 5

1,2-Oxazinane hydrochloride

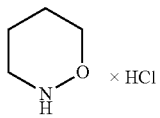

The title compound can be prepared according to literature procedures, see, for example, H. King, *J. Chem. Soc.* 1942, 432.

Starting Material 6

2-Oxa-3-azabicyclo[2.2.2]oct-5-ene

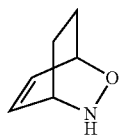

The title compound can be prepared in Boc-protected form according to a literature procedure (see, for example, C. Johnson et al., *Tetrahedron Lett.* 1998, 39, 2059); deprotection is carried out in a customary manner by treatment with trifluoroacetic acid and subsequent neutralization.
Yield: 149 mg (89% of theory).

Starting Material 7

1,2-Oxazolidin-4-ol

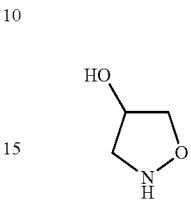

The title compound can be prepared according to literature procedures, see, for example, N. Amlalky, *Synthesis* 1982, 5, 426.

Starting Material 8 tert-Butyl[(1S,2R)-1-(hydroxycarbamoyl)-2-phenylcyclopropyl]carbamate

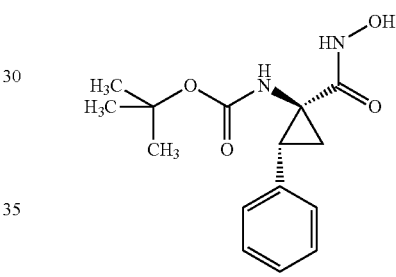

The title compound was prepared in accordance with a literature procedure (A. Ritter et al., *J. Org. Chem.* 1994, 59, 4602) from commercially available (1S,2R)-1-[(tert-butoxycarbonyl)amino]-2-phenylcyclopropanecarboxylic acid (C. Cativiela et al., *Chirality* 1999, 11, 583).
Yield: 339 mg (59% of theory)
LC-MS (Method 1): R$_t$=0.82 min; MS (ESIpos): m/z=293 (M+H)$^+$.

Intermediate 1 tert-Butyl (3R,4S,5S)-4-[{N-[(benzyloxy)carbonyl]-L-valyl}(methyl)amino]-3-methoxy-5-methyl-heptanoate

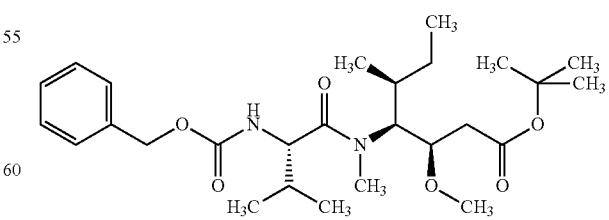

425 mg (1.7 mmol) of N-[(benzyloxy)carbonyl]-L-valine were dissolved in 50 ml of DMF, and 500 mg (1.7 mmol) of tert-butyl (3R,4S,5S)-3-methoxy-5-methyl-4-(methylamino) heptanoate hydrochloride (Starting Material 2), 356 mg (1.9 mmol) of 1-(3-dimethylaminopropyl)-3-ethylcarbodiimide hydrochloride, 285 mg (1.9 mmol) of 1-hydroxy-1H-benzotriazole hydrate and 655 mg (5.1 mmol) of N,N-diisopropylethylamine were added in succession. The mixture was stirred at RT for 20 h. Another 142 mg (0.5 mmol) of N-[(benzyloxy)carbonyl]-L-valine, 119 mg (0.6 mmol) of 1-(3-dimethylaminopropyl)-3-ethylcarbodiimide hydrochloride, 95 mg (0.6 mmol) of 1-hydroxy-1H-benzotriazole hydrate and 218 mg (1.7 mmol) of N,N-diisopropylethylamine were added, and the mixture was treated with ultrasound for 90 min. The mixture was then poured into a mixture of semisaturated aqueous ammonium chloride solution and ethyl acetate. The organic phase was separated off, washed successively with saturated sodium bicarbonate solution and saturated sodium chloride solution, dried over magnesium sulphate, filtered and concentrated. The residue was purified by preparative HPLC. This gave 329 mg (40% of theory) of the title compound as a colourless oil.

HPLC (Method 5): $R_t$=2.5 min;

LC-MS (Method 1): $R_t$=1.45 min; MS (ESIpos): m/z=493 (M+H)$^+$.

Intermediate 2 tert-Butyl (3R,4S,5S)-3-methoxy-5-methyl-4-[methyl(L-valyl)amino]heptanoate

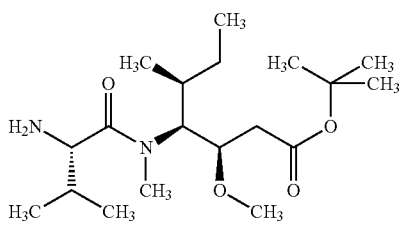 [SMILES: CC[C@H](C)[C@@H]([C@@H](CC(=O)OC(C)(C)C)OC)N(C)C(=O)[C@@H](N)C(C)C]

500 mg (1 mmol) of tert-butyl (3R,4S,5S)-4-[{N-[(benzyloxy)carbonyl]-L-valyl}(methyl)amino]-3-methoxy-5-methylheptanoate (Intermediate 1) were dissolved in 50 ml of methanol and, after addition of 100 mg of 10% palladium on activated carbon, hydrogenated at RT under atmospheric pressure for 1 h. The catalyst was then filtered off and the solvent was removed under reduced pressure. This gave 370 mg (quant.) of the title compound as an almost colourless oil.

HPLC (Method 5): $R_t$=1.59 min;

LC-MS (Method 1): $R_t$=0.74 min; MS (ESIpos): m/z=359 (M+H)$^+$.

Intermediate 3

N-[(9H-Fluoren-9-ylmethoxy)carbonyl]-N-methyl-L-valyl-N-[(3R,4S,5S)-1-tert-butoxy-3-methoxy-5-methyl-1-oxoheptan-4-yl]-N-methyl-L-valinamide

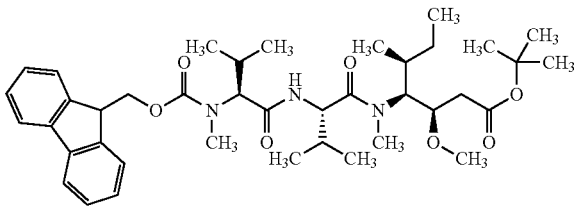 [SMILES: CC[C@H](C)[C@@H]([C@@H](CC(=O)OC(C)(C)C)OC)N(C)C(=O)[C@@H](NC(=O)[C@H](C(C)C)N(C)C(=O)OCC1c2ccccc2-c2ccccc21)C(C)C]

396 mg (1.1 mmol) of N-[(9H-fluoren-9-ylmethoxy)carbonyl]-N-methyl-L-valine were dissolved in 20 ml of DMF, and 365 mg (1 mmol) of tert-butyl (3R,4S,5S)-3-methoxy-5-methyl-4-[methyl(L-valyl)amino]heptanoate (Intermediate 2), 234 mg (1.2 mmol) of 1-(3-dimethylaminopropyl)-3-ethylcarbodiimide hydrochloride and 187 mg (1.2 mmol) of 1-hydroxy-1H-benzotriazole hydrate were added in succession. The mixture was stirred at RT overnight. The reaction was then poured into a mixture of semisaturated aqueous ammonium chloride solution and ethyl acetate. The organic phase was separated off, washed successively with saturated sodium bicarbonate solution and saturated sodium chloride solution, dried over magnesium sulphate, filtered and concentrated. The residue was used directly, without further purification, for the next step.

Yield: 660 mg (68% of theory)

HPLC (Method 5): $R_t$=3 0 min;

LC-MS (Method 1): $R_t$=1.61 min; MS (ESIpos): m/z=694 (M+H)$^+$.

Intermediate 4

N-[(9H-Fluoren-9-ylmethoxy)carbonyl]-N-methyl-L-valyl-N-[(2R,3S,4S)-1-carboxy-2-methoxy-4-methylhexan-3-yl]-N-methyl-L-valinamide

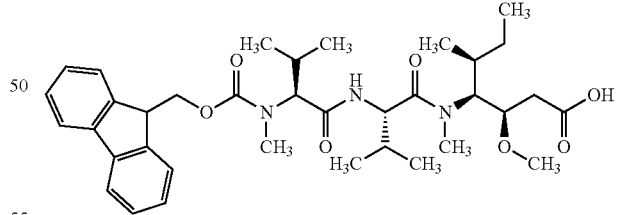

650 mg (0.94 mmol) of N-[(9H-fluoren-9-ylmethoxy)carbonyl]-N-methyl-L-valyl-N-[(3R,4S,5S)-1-tert-butoxy-3-methoxy-5-methyl-1-oxoheptan-4-yl]-N-methyl-L-valinamide (Intermediate 3) were taken up in 5 ml of dichloromethane, 5 ml of trifluoroacetic acid were added and the mixture was stirred at RT overnight. The mixture was then concentrated under reduced pressure, and the residue that remained was purified by preparative HPLC. This gave 430 mg (72% of theory) of the title compound as a colourless foam.

HPLC (Method 5): $R_t$=2 4 min;

LC-MS (Method 2): $R_t$=1.51 min; MS (ESIpos): m/z=638 (M+H)$^+$.

Intermediate 5 tert-Butyl[(2S)-1-(1,2-oxazinan-2-yl)-1-oxo-3-phenylpropan-2-yl]carbamate

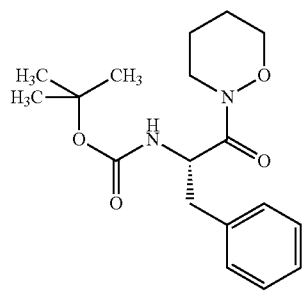 [SMILES: CC(C)(C)OC(=O)N[C@@H](Cc1ccccc1)C(=O)N1CCCCO1]

500 mg (1.9 mmol) of N-(tert-butoxycarbonyl)-L-phenylalanine were dissolved in 10 ml of DMF, and 466 mg (3.8 mmol) of 1,2-oxazinane hydrochloride (Starting Material 5), 433 mg (2.3 mmol) of 1-(3-dimethylaminopropyl)-3-ethylcarbodiimide hydrochloride, 382 mg (2.8 mmol) of 1-hydroxy-1H-benzotriazole hydrate and 731 mg (5.7 mmol) of N,N-diisopropylethylamine were added in succession. The mixture was stirred at RT overnight. The reaction was then poured into a mixture of semisaturated aqueous ammonium chloride solution and ethyl acetate. The organic phase was separated off, washed successively with saturated sodium bicarbonate solution and saturated sodium chloride solution, dried over magnesium sulphate, filtered and concentrated. This gave 620 mg (98% of theory) of the title compound.

HPLC (Method 5): $R_t$=1 8 min;

LC-MS (Method 2): $R_t$=1.62 min; MS (ESIpos): m/z=235 (M-C$_4$H$_8$—CO$_2$+H)$^+$.

Intermediate 6

(2S)-2-Amino-1-(1,2-oxazinan-2-yl)-3-phenylpropan-1-one, trifluoroacetic acid salt

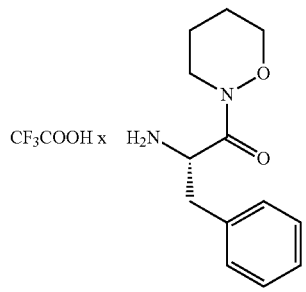

620 mg (1.85 mmol) of tert-butyl[(2S)-1-(1,2-oxazinan-2-yl)-1-oxo-3-phenylpropan-2-yl]carbamate (Intermediate 5) were taken up in 5 ml of dichloromethane, 10 ml of trifluoroacetic acid were added and the mixture was stirred at RT for 30 min. The mixture was then concentrated under reduced pressure, and the residue that remained was lyophilized from water/acetonitrile. In this manner, 750 mg of the title compound were obtained as a colourless foam.

HPLC (Method 5): $R_t$=0.45 min;

LC-MS (Method 3): $R_t$=1.09 min; MS (ESIpos): m/z=235 (M+H)$^+$.

Intermediate 7

(2R,3R)-3-Methoxy-2-methyl-N-[(2S)-1-(1,2-oxazinan-2-yl)-1-oxo-3-phenylpropan-2-yl]-3-[(2S)-pyrrolidin-2-yl]propanamide, trifluoroacetic acid salt First, (2R,3R)-3-[(2S)-1-(tert-butoxycarbonyl)pyrrolidin-2-yl]-3-methoxy-2-methylpropanoic acid (Starting Material 1) was released from 50 mg (0.11 mmol) of its dicyclohexylamine salt by taking up the salt in ethyl acetate and extracting with aqueous potassium bisulphate solution. The organic phase was dried over magnesium sulphate, filtered and concentrated. The residue was taken up in 10 ml of DMF, and 49 mg (0.11 mmol) of (2S)-2-amino-1-(1,2-oxazinan-2-yl)-3-phenylpropan-1-one, trifluoroacetic acid salt (Intermediate 6), 61 mg (0.16 mmol) of O-(7-azabenzotriazol-1-yl)-N,N,N',N'-tetramethyluronium hexafluorophosphate (HATU) and 56 µl (0.16 mmol) of N,N-diisopropylethylamine were added in succession. The mixture was stirred at RT for 1 h. The reaction was then concentrated and the residue was purified by preparative HPLC. This gave 44 mg (82% of theory) of the Boc-protected intermediate tert-butyl (2S)-2-[(1R,2R)-1-methoxy-2-methyl-3-{[(2S)-1-(1,2-oxazinan-2-yl)-1-oxo-3-phenylpropan-2-yl]amino}-3-oxopropyl]-pyrrolidine-1-carboxylate.

HPLC (Method 5): $R_t$=1.9 min;

LC-MS (Method 2): $R_t$=1.27 min; MS (ESIpos): m/z=504 (M+H)$^+$.

44 mg (0.09 mmol) of this intermediate were taken up in 3 ml of dichloromethane, 1 ml of trifluoroacetic acid was added and the mixture was stirred at RT for 30 min. The mixture was then concentrated under reduced pressure, and the residue that remained was lyophilized from water/acetonitrile. This gave 39 mg (86% of theory) of the title compound as a colourless foam.

HPLC (Method 5): $R_t$=0.94 min;

LC-MS (Method 1): $R_t$=0.65 min; MS (ESIpos): m/z=404 (M+H)$^+$.

Intermediate 8

(2S)-2-Amino-1-(2-oxa-3-azabicyclo[2.2.2]oct-5-en-3-yl)-3-phenylpropan-1-one, trifluoroacetic acid salt

Intermediate 9

(2R,3R)-3-Methoxy-2-methyl-N-[(2S)-1-(2-oxa-3-azabicyclo[2.2.2]oct-5-en-3-yl)-1-oxo-3-phenylpropan-2-yl]-3-[(2S)-pyrrolidin-2-yl]propanamide, trifluoroacetic acid salt

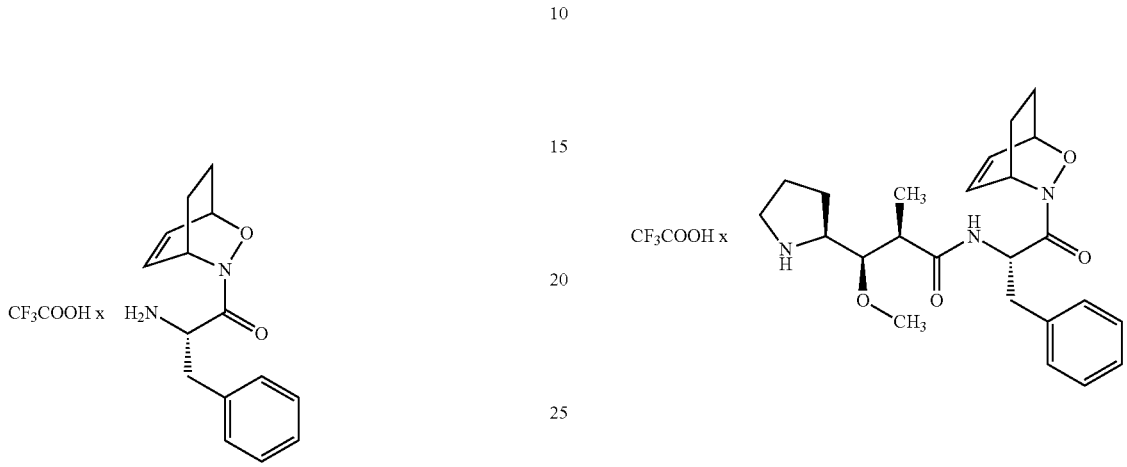

41 mg (0.37 mmol) of 2,5-dioxopyrrolidin-1-yl N-(tert-butoxycarbonyl)-L-phenylalaninate were taken up in 10 ml of DMF, and 149 mg (0.41 mmol) of 2-oxa-3-azabicyclo[2.2.2]oct-5-ene (Starting Material 6) and 72 µl (0.41 mmol) of N,N-diisopropylethylamine were added. The mixture was stirred at RT for 1 h. The solvent was then removed under reduced pressure, and the residue was taken up in ethyl acetate and extracted with 5% strength citric acid solution and then with 5% strength sodium bicarbonate solution. The organic phase was concentrated and the residue was purified by flash chromatography on silica gel using the mobile phase toluene/ethanol 10:1. The appropriate fractions were combined and the solvent was removed under reduced pressure. Drying of the residue under high vacuum gave 69 mg (47% of theory) of the Boc-protected intermediate tert-butyl[(2S)-1-(2-oxa-3-azabicyclo[2.2.2]oct-5-en-3-yl)-1-oxo-3-phenylpropan-2-yl]carbamate as a mixture of diastereomers.

LC-MS (Method 1): $R_t$=1.1 min; MS (ESIpos): m/z=359 (M+H)$^+$.

64 mg (0.18 mmol) of this intermediate were taken up in 10 ml of dichloromethane, 1 ml of trifluoroacetic acid was added and the mixture was stirred at RT for 30 min. The mixture was then concentrated under reduced pressure, and the residue that remained was lyophilized from water/dioxane. In this manner, 66 mg (quant.) of the title compound were obtained as a colourless foam.

HPLC (Method 6): $R_t$=1.45 min;
LC-MS (Method 3): $R_t$=1.12 min; MS (ESIpos): m/z=259 (M+H)$^+$.

First, (2R,3R)-3-[(2S)-1-(tert-butoxycarbonyl)pyrrolidin-2-yl]-3-methoxy-2-methylpropanoic acid (Starting Material 1) was released from 83 mg (0.18 mmol) of its dicyclohexylamine salt by taking up the salt in ethyl acetate and extracting with aqueous potassium bisulphate solution. The organic phase was dried over magnesium sulphate, filtered and concentrated. The residue was taken up in 10 ml of DMF, and 66 mg (0.18 mmol) of (2S)-2-amino-1-(2-oxa-3-azabicyclo[2.2.2]oct-5-en-3-yl)-3-phenylpropan-1-one, trifluoroacetic acid salt (Intermediate 8), 101 mg (0.266 mmol) of O-(7-azabenzotriazol-1-yl)-N,N,N',N'-tetramethyluronium hexafluorophosphate (HATU) and 93 µl (0.53 mmol) of N,N-diisopropylethylamine were added in succession. The mixture was stirred at RT for 30 min. The reaction was then concentrated and the residue was purified by preparative HPLC. This gave 52 mg (56% of theory) of the Boc-protected intermediate tert-butyl (2S)-2-[(1R,2R)-1-methoxy-2-methyl-3-{[(2S)-1-(2-oxa-3-azabicyclo[2.2.2]oct-5-en-3-yl)-1-oxo-3-phenylpropan-2-yl]amino}-3-oxopropyl]pyrrolidine-1-carboxylate.

HPLC (Method 6): $R_t$=2.13 min;
LC-MS (Method 1): $R_t$=1.13 min; MS (ESIpos): m/z=528 (M+H)$^+$.

52 mg (0.1 mmol) of this intermediate were taken up in 10 ml of dichloromethane, 1 ml of trifluoroacetic acid was added and the mixture was stirred at RT for 20 min. The mixture was then concentrated under reduced pressure, and the residue that remained was triturated with 20 ml of diethyl ether. After 10 min, the mixture was filtered off and the filter residue was dried under high vacuum. In this manner, 39 mg (72% of theory) of the title compound were obtained.

HPLC (Method 6): $R_t$=1.62 min;
LC-MS (Method 1): $R_t$=0.68 min; MS (ESIpos): m/z=428 (M+H)$^+$.

Intermediate 10

(2S)-2-Amino-1-(1,4-dihydro-3H-2,3-benzoxazin-3-yl)-3-phenylpropan-1-one, trifluoroacetic acid salt

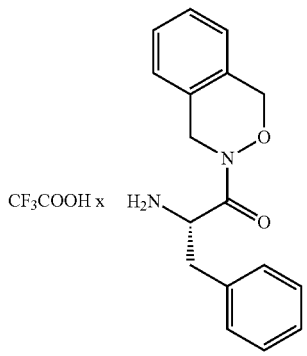

First, starting with 75 mg (0.27 mmol) of $N^\alpha$-(tert-butoxycarbonyl)-N-hydroxy-L-phenyl-alaninamide (Starting Material 3), the Boc-protected intermediate tert-butyl[(2S)-1-(1,4-dihydro-3H-2,3-benzoxazin-3-yl)-1-oxo-3-phenylpropan-2-yl]carbamate was prepared by reaction with 1,2-bis(bromomethyl)benzene analogously to a literature procedure (see H. King, *J. Chem. Soc.* 1942, 432).

Yield: 36 mg (35% of theory)

LC-MS (Method 3): $R_t$=2.49 min; MS (ESIpos): m/z=383 (M+H)$^+$.

36 mg (0.094 mmol) of this intermediate were taken up in 5 ml of dichloromethane, 0.5 ml of trifluoroacetic acid was added and the mixture was stirred at RT for 20 min. The mixture was then concentrated under reduced pressure, and the residue that remained was purified by preparative HPLC. The appropriate fractions were combined, concentrated under reduced pressure to a volume of about 15 ml and then lyophilized. This gave 16 mg (43% of theory) of the title compound as a colourless foam.

HPLC (Method 6): $R_t$=1 7 min;

LC-MS (Method 1): $R_t$=0.69 min; MS (ESIpos): m/z=283 (M+H)$^+$.

Intermediate 11

(2R,3R)—N-[(2S)-1-(1,4-Dihydro-3H-2,3-benzoxazin-3-yl)-1-oxo-3-phenylpropan-2-yl]-3-methoxy-2-methyl-3-[(2S)-pyrrolidin-2-yl]propanamide, trifluoroacetic acid salt

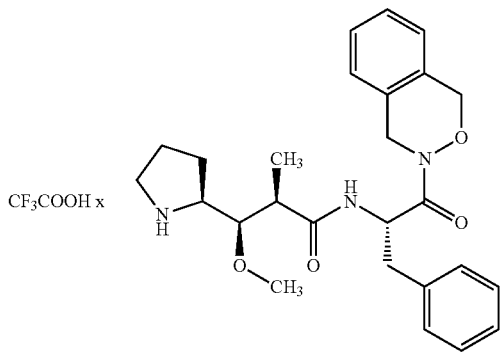

Initially, (2R,3R)-3-[(2S)-1-(tert-butoxycarbonyl)pyrrolidin-2-yl]-3-methoxy-2-methylpropanoic acid (Starting Material 1) was released from 15 mg (0.031 mmol) of its dicyclohexylamine salt by taking up the salt in ethyl acetate and extracting with aqueous potassium bisulphate solution. The organic phase was dried over magnesium sulphate, filtered and concentrated. The residue was taken up in 10 ml of DMF, and 16 mg (0.031 mmol) of (2S)-2-amino-1-(1,4-dihydro-3H-2,3-benzoxazin-3-yl)-3-phenylpropan-1-one, trifluoroacetic acid salt (Intermediate 10), 18 mg (0.047 mmol) of O-(7-azabenzotriazol-1-yl)-N,N,N',N'-tetramethyluranium hexafluorophosphate (HATU) and 16 µl (0.53 mmol) of N,N-diisopropylethylamine were added in succession. The mixture was stirred at RT for 16 h. The reaction was then concentrated and the residue was purified by preparative HPLC. This gave 14 mg (81% of theory) of the Boc-protected intermediate tert-butyl (2S)-2-[(1R,2R)-3-{[(2S)-1-(1,4-dihydro-3H-2,3-benzoxazin-3-yl)-1-oxo-3-phenylpropan-2-yl]amino}-1-methoxy-2-methyl-3-oxopropyl]pyrrolidine-1-carboxylate.

HPLC (Method 6): $R_t$=2.35 min;

LC-MS (Method 2): $R_t$=1.39 min; MS (ESIpos): m/z=552 (M+H)$^+$.

14 mg (0.025 mmol) of this intermediate were taken up in 5 ml of dichloromethane, 1 ml of trifluoroacetic acid was added and the mixture was stirred at RT for 20 min. The mixture was then concentrated under reduced pressure, and the residue that remained was lyophilized from dioxane. In this manner, 14 mg (98% of theory) of the title compound were obtained.

HPLC (Method 6): $R_t$=1.83 min;

LC-MS (Method 1): $R_t$=0.78 min; MS (ESIpos): m/z=452 (M+H)$^+$.

Intermediate 12

(2S)-2-Amino-3-(1H-indol-3-yl)-1-(1,2-oxazinan-2-yl)propan-1-one, trifluoroacetic acid salt

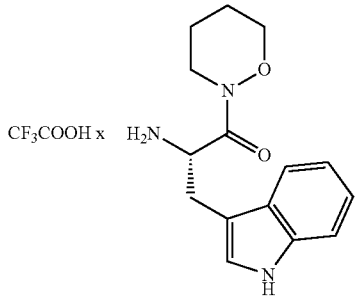

130 mg (0.324 mmol) of 2,5-dioxopyrrolidin-1-yl N-(tert-butoxycarbonyl)-L-tryptophanate were taken up in 15 ml of DMF, and 50 mg (0.405 mmol) of 1,2-oxazinane hydrochloride (Starting Material 5) and 140 µl of N,N-diisopropylethylamine were added. The mixture was stirred at RT for 24 h. The same amount of 1,2-oxazinane hydrochloride and N,N-diisopropylethylamine were then added. After a further 4 h of stirring at RT, the reaction was concentrated under reduced pressure, and the residue was taken up in dichloromethane and extracted first with sodium bicarbonate solution and then with water. The organic phase was concentrated and the residue was purified by flash chromatography on silica gel using the mobile phase dichloromethane/ethyl acetate 4:1. The appropriate fractions were concentrated and the residue was dried under high vacuum. This gave 63 mg (52% of theory) of the Boc-protected intermediate tert-butyl[(2S)-3-(1H-indol-3-yl)-1-(1,2-oxazinan-2-yl)-1-oxopropan-2-yl]carbamate.

HPLC (Method 6): $R_t$=2.05 min;
LC-MS (Method 3): $R_t$=2.16 min; MS (ESIpos): m/z=374 (M+H)$^+$.

63 mg (0.167 mmol) of this intermediate were taken up in 15 ml of dichloromethane, 2 ml of trifluoroacetic acid were added and the mixture was treated in an ultrasonic bath for 40 min. The reaction was then concentrated under reduced pressure and the residue was lyophilized from dioxane/water. In this manner, 65 mg (90% of theory) of the title compound were obtained.

HPLC (Method 6): $R_t$=1.53 min;
LC-MS (Method 1): $R_t$=0.61 min; MS (ESIpos): m/z=274 (M+H)$^+$.

Intermediate 13

(2R,3R)—N-[(2S)-3-(1H-Indol-3-yl)-1-(1,2-oxazinan-2-yl)-1-oxopropan-2-yl]-3-methoxy-2-methyl-3-[(2S)-pyrrolidin-2-yl]propanamide, trifluoroacetic acid salt

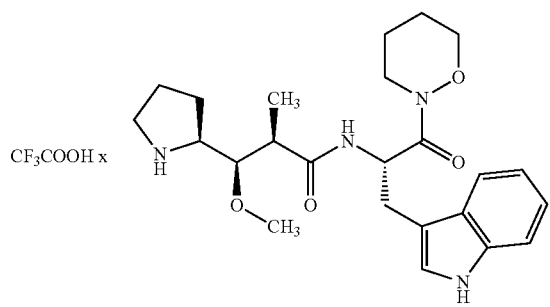

The title compound was prepared analogously to the synthesis of Intermediate 7 in two steps from the dicyclohexylamine salt of Starting Material 1 and (2S)-2-amino-3-(1H-indol-3-yl)-1-(1,2-oxazinan-2-yl)propan-1-one, trifluoroacetic acid salt (Intermediate 12).

Yield over 2 steps: 62 mg (67% of theory)
HPLC (Method 6): $R_t$=1.65 min;
LC-MS (Method 1): $R_t$=0.7 min; MS (ESIpos): m/z=443 (M+H)$^+$.

Intermediate 14

(2S)-2-Amino-1-(1,2-oxazolidin-2-yl)-3-phenylpropan-1-one, trifluoroacetic acid salt

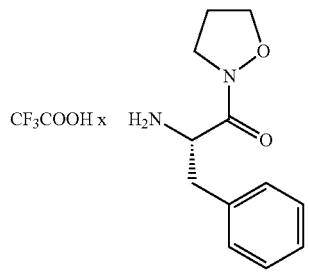

The title compound was prepared analogously to the synthesis of Intermediates 5 and 6 in two steps from N-(tert-butoxycarbonyl)-L-phenylalanine and 1,2-oxazolidine hydrochloride (Starting Material 4).

Yield over 2 steps: 1650 mg (97% of theory)
HPLC (Method 5): $R_t$=0.29 min;
LC-MS (Method 1): $R_t$=0.41 min; MS (ESIpos): m/z=221 (M+H)$^+$.

Intermediate 15

(2R,3R)-3-Methoxy-2-methyl-N-[(2S)-1-(1,2-oxazolidin-2-yl)-1-oxo-3-phenylpropan-2-yl]-3-[(2S)-pyrrolidin-2-yl]propanamide, trifluoroacetic acid salt

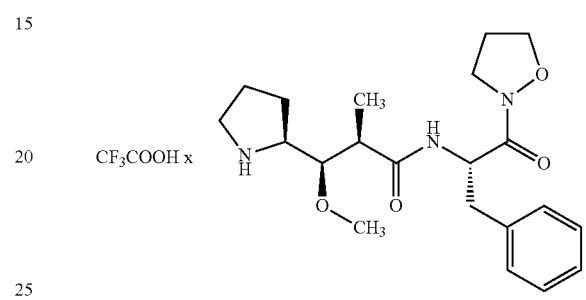

The title compound was prepared analogously to the synthesis of Intermediate 7 in two steps from the dicyclohexylamine salt of Starting Material 1 and (2S)-2-amino-1-(1,2-oxazolidin-2-yl)-3-phenylpropan-1-one, trifluoroacetic acid salt (Intermediate 14).

Yield over 2 steps: 110 mg (97% of theory)
HPLC (Method 5): $R_t$=0.52 min;
LC-MS (Method 3): $R_t$=1.15 min; MS (ESIpos): m/z=390 (M+H)$^+$.

Intermediate 16

(2S,3S)-2-Amino-1-(1,2-oxazinan-2-yl)-3-phenylbutan-1-one, trifluoroacetic acid salt

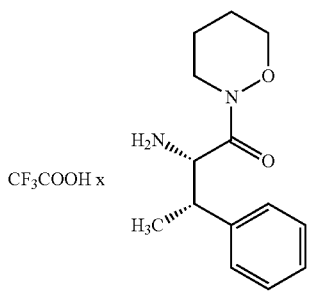 [SMILES: "CF3COOH x" ; C[C@@H](c1ccccc1)[C@H](N)C(=O)N1CCCCO1]

The title compound was prepared analogously to the synthesis of Intermediates 5 and 6 in two steps from (βS)—N-(tert-butoxycarbonyl)-β-methyl-L-phenylalanine and 1,2-oxazinane hydrochloride (Starting Material 5).

Yield over 2 steps: 652 mg (63% of theory)
HPLC (Method 5): $R_t$=0.53 min;
LC-MS (Method 1): $R_t$=1.25 min; MS (ESIpos): m/z=249 (M+H)$^+$.

Intermediate 17

(2R,3R)-3-Methoxy-2-methyl-N-[(2S,3S)-1-(1,2-oxazinan-2-yl)-1-oxo-3-phenylbutan-2-yl]-3-[(2S)-pyrrolidin-2-yl]propanamide, trifluoroacetic acid salt

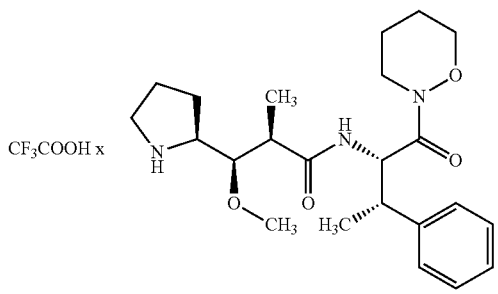

The title compound was prepared analogously to the synthesis of Intermediate 7 in two steps from the dicyclohexylamine salt of Starting Material 1 and (2S,3S)-2-amino-1-(1,2-oxazinan-2-yl)-3-phenylbutan-1-one, trifluoroacetic acid salt (Intermediate 16).

Yield over 2 steps: 101 mg (90% of theory)
HPLC (Method 5): $R_t$=1.07 min;
LC-MS (Method 3): $R_t$=1.33 min; MS (ESIpos): m/z=418 $(M+H)^+$.

Intermediate 18 (2S)-2-Amino-3-(4-hydroxy-3-nitrophenyl)-1-(1,2-oxazinan-2-yl)propan-1-one, trifluoroacetic acid salt

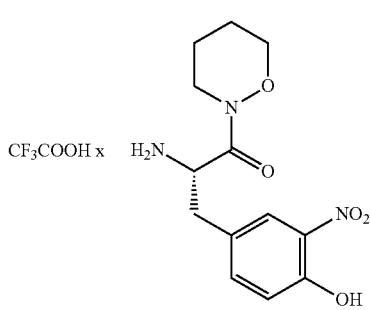

The title compound was prepared analogously to the synthesis of Intermediates 5 and 6 in two steps from N-(tert-butoxycarbonyl)-3-nitro-L-tyrosine and 1,2-oxazinane hydrochloride (Starting Material 5).

Yield over 2 steps: 374 mg (47% of theory)
HPLC (Method 5): $R_t$=0 4 min;
LC-MS (Method 1): $R_t$=0.5 min; MS (ESIpos): m/z=296 $(M+H)^+$.

Intermediate 19

(2R,3R)—N-[(2S)-3-(4-Hydroxy-3-nitrophenyl)-1-(1,2-oxazinan-2-yl)-1-oxopropan-2-yl]-3-methoxy-2-methyl-3-[(2S)-pyrrolidin-2-yl]propanamide, trifluoroacetic acid salt

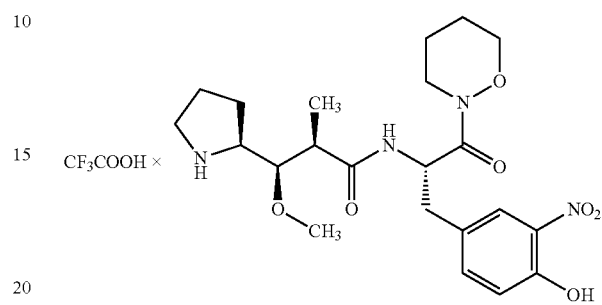

The title compound was prepared analogously to the synthesis of Intermediate 7 in two steps from the dicyclohexylamine salt of Starting Material 1 and (2S)-2-amino-3-(4-hydroxy-3-nitrophenyl)-1-(1,2-oxazinan-2-yl)propan-1-one, trifluoroacetic acid salt (Intermediate 18). The product, which was obtained in a purity of 63%, was used as such, without further purification, for subsequent reactions.

Yield over 2 steps: 128 mg (61% of theory)
HPLC (Method 5): $R_t$=0 8 min;
LC-MS (Method 3): $R_t$=1.24 min; MS (ESIpos): m/z=465 $(M+H)^+$.

Intermediate 20

N-(tert-Butoxycarbonyl)-N-methyl-L-valyl-N-[(2R,3S,4S)-1-carboxy-2-methoxy-4-methylhexan-3-yl]-N-methyl-L-valinamide

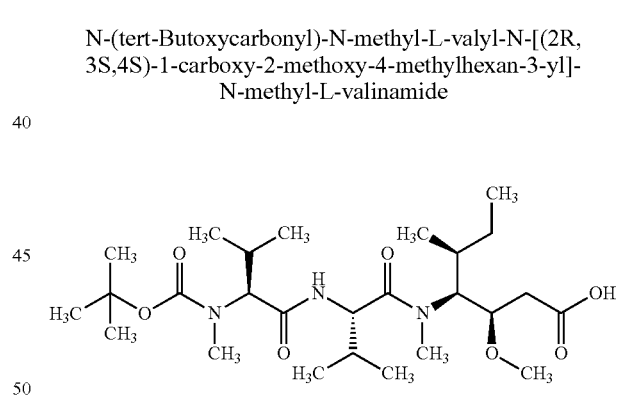

51 mg (0.08 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were dissolved in 10 ml of DMF, and 0.5 ml of piperidine was added. After 10 min of stirring at RT, the reaction was concentrated under reduced pressure and the residue was triturated with diethyl ether. The insoluble components were filtered off and washed repeatedly with diethyl ether. The filter residue was then taken up in 5 ml of dioxane/water (1:1), and the solution was adjusted to pH 11 with 1 N aqueous sodium hydroxide solution. With ultrasound treatment, a total of 349 mg (1.6 mmol) of di-tert-butyl dicarbonate were added in a plurality of portions, the pH of the solution being maintained at 11. After the reaction had ended, the dioxane was evaporated and the aqueous solution was adjusted to a pH of 2-3 using citric acid. The mixture was extracted twice with in each case 50 ml of ethyl acetate. The organic phases were combined, dried over magnesium sulphate and concentrated under reduced pressure. The residue was taken up in diethyl ether and the product was precipitated with pentane. The solvent was removed by decanting. The residue was repeatedly digested with pentane and finally dried under high vacuum. This gave 31 mg (93% of theory) of the title compound.

HPLC (Method 6): $R_t$=2.2 min;
LC-MS (Method 2): $R_t$=1.32 min; MS (ESIpos): m/z=516 (M+H)$^+$.

Intermediate 21 tert-Butyl (2S)-2-[(1R,2R)-3-{[(2S)-3,3-dimethyl-1-(1,2-oxazinan-2-yl)-1-oxobutan-2-yl]amino}-1-methoxy-2-methyl-3-oxopropyl]pyrrolidine-1-carboxylate

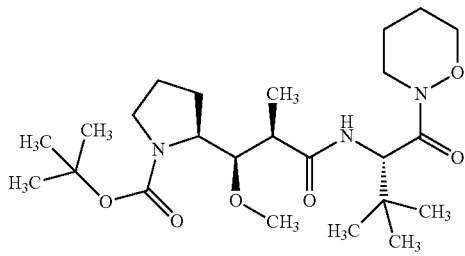 [SMILES: CO[C@H]([C@@H](C)C(=O)N[C@H](C(=O)N1CCCCO1)C(C)(C)C)[C@@H]1CCCN1C(=O)OC(C)(C)C]

The title compound was prepared analogously to the synthesis of Intermediates 5 and 6 in three steps by coupling commercially available N-(tert-butoxycarbonyl)-3-methyl-L-valine with 1,2-oxazinane hydrochloride (Starting Material 5), subsequent deprotection with trifluoroacetic acid and another coupling with Starting Material 1. The end product was purified by preparative HPLC.

HPLC (Method 5): $R_t$=1.92 min;
LC-MS (Method 7): $R_t$=2.19 min; MS (ESIpos): m/z=470 (M+H)$^+$.

Intermediate 22 tert-Butyl (2S)-2-[(1R,2R)-1-methoxy-2-methyl-3-{[(2S)-1-(1,2-oxazinan-2-yl)-1-oxo-3,3-diphenylpropan-2-yl]amino}-3-oxopropyl]pyrrolidine-1-carboxylate

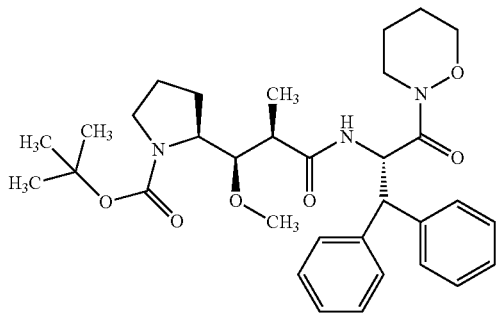 [SMILES: CO[C@H]([C@@H](C)C(=O)N[C@H](C(=O)N1CCCCO1)C(c1ccccc1)c1ccccc1)[C@@H]1CCCN1C(=O)OC(C)(C)C]

The title compound was prepared analogously to the synthesis of Intermediates 5 and 6 in three steps by coupling commercially available N-(tert-butoxycarbonyl)-β-phenyl-L-phenylalanine with 1,2-oxazinane hydrochloride (Starting Material 5), subsequent deprotection with trifluoroacetic acid and another coupling with Starting Material 1. The end product was purified by preparative HPLC.

HPLC (Method 5): $R_t$=2.07 min;
LC-MS (Method 1): $R_t$=1.22 min; MS (ESIpos): m/z=580 (M+H)$^+$.

Intermediate 23 tert-Butyl (2S)-2-[(1R,2R)-1-methoxy-2-methyl-3-{[(1S,2S)-1-(1,2-oxazinan-2-ylcarbonyl)-2-phenylcyclopropyl]amino}-3-oxopropyl]pyrrolidine-1-carboxylate

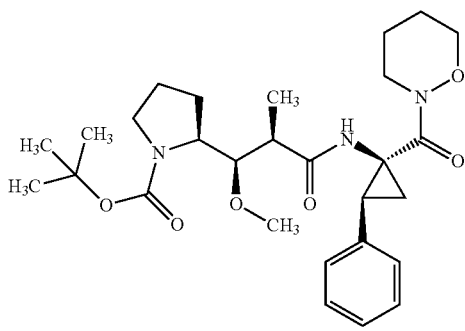 [SMILES: CO[C@H]([C@@H](C)C(=O)N[C@@]1(C(=O)N2CCCCO2)C[C@H]1c1ccccc1)[C@@H]1CCCN1C(=O)OC(C)(C)C]

The title compound was prepared analogously to the synthesis of Intermediates 5 and 6 in three steps by coupling commercially available (1S,2S)-1-[(tert-butoxycarbonyl)amino]-2-phenylcyclopropanecarboxylic acid with 1,2-oxazinane hydrochloride (Starting Material 5), subsequent deprotection with trifluoroacetic acid and another coupling with Starting Material 1. The end product was purified by preparative HPLC.

HPLC (Method 5): $R_t$=2.19 min;
LC-MS (Method 3): $R_t$=2.28 min; MS (ESIpos): m/z=516 (M+H)$^+$.

Intermediate 24 tert-Butyl (2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidine-1-carboxylate

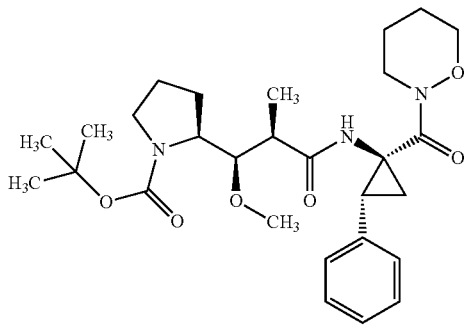 [SMILES: CO[C@H]([C@@H](C)C(=O)N[C@@]1(C(=O)N2CCCCO2)C[C@@H]1c1ccccc1)[C@@H]1CCCN1C(=O)OC(C)(C)C]

The title compound was prepared analogously to the synthesis of Intermediates 5 and 6 in three steps by coupling commercially available (1S,2R)-1-[(tert-butoxycarbonyl)amino]-2-phenylcyclopropanecarboxylic acid with 1,2-oxazinane hydrochloride (Starting Material 5), subsequent deprotection with trifluoroacetic acid and another coupling with Starting Material 1. The end product was purified by preparative HPLC.

HPLC (Method 5): $R_t$=2.12 min;

LC-MS (Method 2): $R_t$=1.25 min; MS (ESIpos): m/z=516 (M+H)$^+$.

Intermediate 25 tert-Butyl[(2S)-1-(4-hydroxy-1,2-oxazolidin-2-yl)-1-oxo-3-phenylpropan-2-yl]carbamate (Diastereomers 1 and 2)

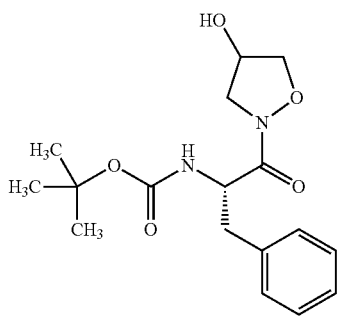 [SMILES: CC(C)(C)OC(=O)N[C@@H](Cc1ccccc1)C(=O)N1CC(O)CO1]

200 mg (1.59 mmol) of 1,2-oxazolidin-4-ol (Starting Material 7) were taken up in 10 ml of DMF, and 606 mg (1.67 mmol) of 2,5-dioxopyrrolidin-1-yl-N-(tert-butoxycarbonyl)-L-phenylalaninate and 277 μl of N,N-diisopropylethylamine were added. After 60 h of stirring at RT, the reaction was concentrated under reduced pressure and the residue was taken up in 100 ml of ethyl acetate. The mixture was extracted in each case twice with 5% strength citric acid solution and 10% strength sodium bicarbonate solution. The organic phase was then concentrated under reduced pressure. Further purification and separation of the two diastereomers was carried out by flash chromatography on silica gel using the mobile phase dichloromethane/methanol 98:2. The appropriate fractions were concentrated and the residue was dried under high vacuum.

Diastereomer 1:

Yield: 154 mg [still contaminated by N-(tert-butoxycarbonyl)-L-phenylalanine, which was removed in the next step]

$R_f$=0.44 (dichloromethane/methanol 95:5).

Diastereomer 2:

Yield: 86 mg (16% of theory)

$R_f$=0.40 (dichloromethane/methanol 95:5).

Intermediate 26 tert-Butyl {(2S)-1-[4-(benzyloxy)-1,2-oxazolidin-2-yl]-1-oxo-3-phenylpropan-2-yl]carbamate (Diastereomer 1)

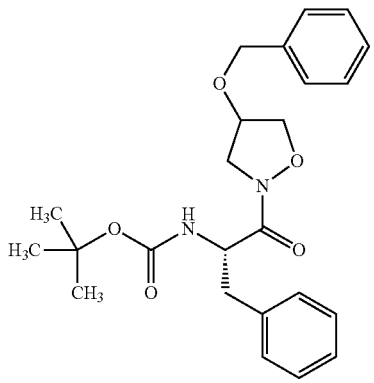 [SMILES: CC(C)(C)OC(=O)N[C@@H](Cc1ccccc1)C(=O)N1CC(OCc2ccccc2)CO1]

75 mg (about 0.22 mmol) of Diastereomer 1 of Intermediate 25 were taken up in 10 ml of acetone, and 228 mg (1.34 mmol) of benzyl bromide, 616 mg (4.46 mmol) of potassium carbonate and a spatula tip of tetra-n-butylammonium iodide were added. The reaction was heated under reflux for 20 h and then concentrated under reduced pressure. The residue was stirred with 100 ml of dichloromethane and filtered, and the dichloromethane phase was then concentrated. The residue that remained was purified by preparative HPLC. This gave 68 mg (72% of theory) of the title compound.

HPLC (Method 6): $R_t$=2.31 min;

LC-MS (Method 1): $R_t$=1.18 min; MS (ESIpos): m/z=427 (M+H)$^+$.

Intermediate 27 tert-Butyl {(2S)-1-[4-(benzyloxy)-1,2-oxazolidin-2-yl]-1-oxo-3-phenylpropan-2-yl}carbamate (Diastereomer 2)

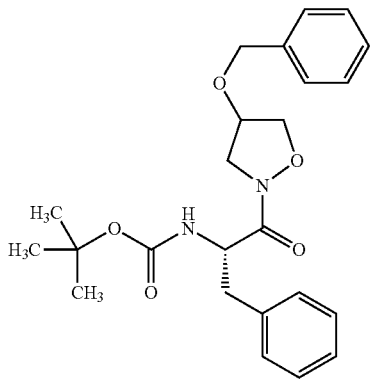 [SMILES: CC(C)(C)OC(=O)N[C@@H](Cc1ccccc1)C(=O)N1CC(OCc2ccccc2)CO1]

83 mg (0.25 mmol) of Diastereomer 2 of Intermediate 25 were taken up in 15 ml of acetone, and 127 mg (0.74 mmol) of benzyl bromide, 682 mg (4.93 mmol) of potassium carbonate and a spatula tip of tetra-n-butylammonium iodide were added. The reaction was heated under reflux for 20 h and then concentrated under reduced pressure. The residue was stirred with 100 ml of dichloromethane and filtered, and the dichloromethane phase was then concentrated. The residue that remained was purified by preparative HPLC. This gave 87 mg (83% of theory) of the title compound.

HPLC (Method 6): $R_t$=2.30 min;

LC-MS (Method 1): $R_t$=1.22 min; MS (ESIpos): m/z=427 (M+H)$^+$.

Intermediate 28

(2S)-2-Amino-1-[4-(benzyloxy)-1,2-oxazolidin-2-yl]-3-phenylpropan-1-one, trifluoroacetic acid salt (Diastereomer 1)

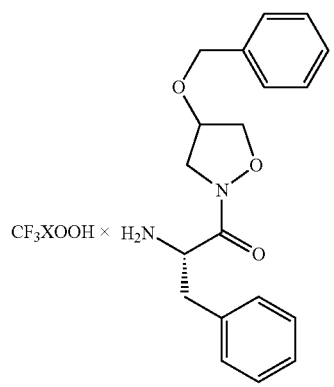 [SMILES: N[C@@H](Cc1ccccc1)C(=O)N1CC(OCc2ccccc2)CO1]

68 mg (0.16 mmol) of tert-butyl {(2S)-1-[4-(benzyloxy)-1,2-oxazolidin-2-yl]-1-oxo-3-phenylpropan-2-yl}carbamate (Diastereomer 1, Intermediate 26) were taken up in 10 ml of dichloromethane, 1 ml of trifluoroacetic acid was added and the mixture was stirred at RT for 30 min. The mixture was then concentrated under reduced pressure, and the residue that remained was lyophilized from dioxane/water. This gave 69 mg (98% of theory) of the title compound as a colourless foam.

HPLC (Method 6): $R_t$=1.72 min;

LC-MS (Method 3): $R_t$=1.41 min; MS (ESIpos): m/z=327 (M+H)$^+$.

Intermediate 29

(2S)-2-Amino-1-[4-(benzyloxy)-1,2-oxazolidin-2-yl]-3-phenylpropan-1-one, trifluoroacetic acid salt (Diastereomer 2)

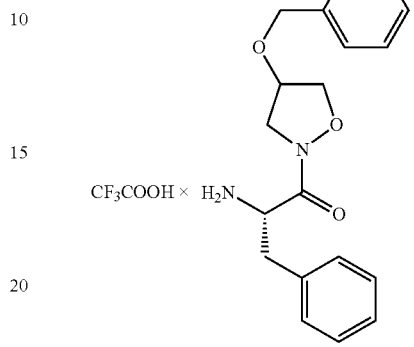

82 mg (0.19 mmol) of tert-butyl {(2S)-1-[4-(benzyloxy)-1,2-oxazolidin-2-yl]-1-oxo-3-phenylpropan-2-yl}carbamate (Diastereomer 2, Intermediate 27) were taken up in 10 ml of dichloromethane, 1 ml of trifluoroacetic acid was added and the mixture was stirred at RT for 30 min. The mixture was then concentrated under reduced pressure, and the residue that remained was lyophilized from dioxane/water. This gave 80 mg (95% of theory) of the title compound as a colourless foam.

HPLC (Method 6): $R_t$=1.80 min;

LC-MS (Method 3): $R_t$=1.50 min; MS (ESIpos): m/z=327 (M+H)$^+$.

Intermediate 30

N-[(9H-Fluoren-9-ylmethoxy)carbonyl]-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide

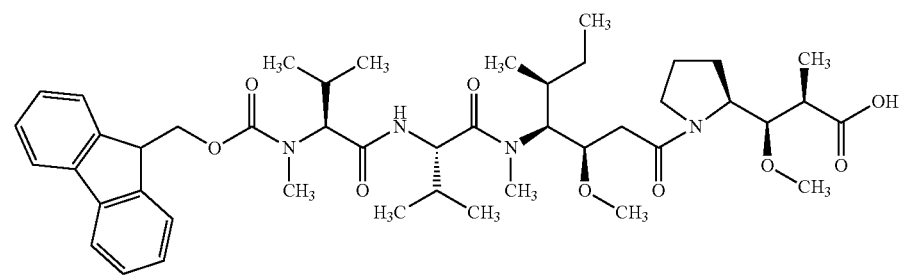 [SMILES: CC[C@H](C)[C@@H]([C@@H](CC(=O)N1CCC[C@H]1[C@H](OC)[C@@H](C)C(=O)O)OC)N(C)C(=O)[C@@H](NC(=O)[C@H](C(C)C)N(C)C(=O)OCC1c2ccccc2-c2ccccc21)C(C)C]

315 mg (0.494 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were dissolved in 12 ml of DMF, 104 mg (0.543 mmol) of 1-(3-dimethylaminopropyl)-3-ethylcarbodiimide hydrochloride and 83 mg (0.543 mmol) of 1-hydroxy-1H-benzotriazole hydrate were added and the mixture was stirred at RT for 90 min 112 µl of N,N-diisopropylethylamine and 149 mg (0.494 mmol) of (2R,3R)-3-methoxy-2-methyl-3-[(2S)-pyrrolidin-2-yl]propanoic acid, trifluoroacetic acid salt, which had been prepared beforehand from Starting Material 1 by removal of the Boc protective group with trifluoroacetic acid, were added. The mixture was stirred at RT for 2 h and then concentrated under high vacuum. The residue that remained was purified by two preparative HPLCs. This gave 140 mg (35% of theory) of the title compound in the form of a colourless foam.

HPLC (Method 5): $R_t$=2.40 min;
LC-MS (Method 1): $R_t$=1.38 min; MS (ESIpos): m/z=807 (M+H)$^+$.

Intermediate 31

[(1S,2R)-1-Amino-2-phenylcyclopropyl](1,4-dihydro-3H-2,3-benzoxazin-3-yl)methanone, trifluoroacetic acid salt

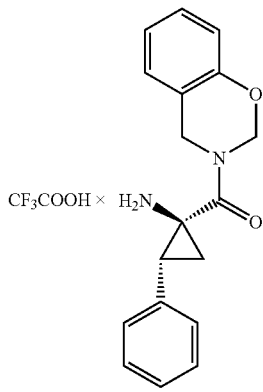 [SMILES: N[C@@]1(C(=O)N2COc3ccccc3C2)C[C@@H]1c1ccccc1]

The title compound was prepared analogously to the synthesis of Intermediate 10 starting with tert-butyl[(1S,2R)-1-(hydroxycarbamoyl)-2-phenylcyclopropyl]carbamate (Starting Material 8).

HPLC (Method 6): $R_t$=1.60 min;
LC-MS (Method 1): $R_t$=0.70 min; MS (ESIpos): m/z=295 (M+H)$^+$.

Intermediate 32

N-[(Benzyloxy)carbonyl]-N-methyl-L-threonyl-N-[(2R,3S,4S)-1-carboxy-2-methoxy-4-methylhexan-3-yl]-N-methyl-L-valinamide

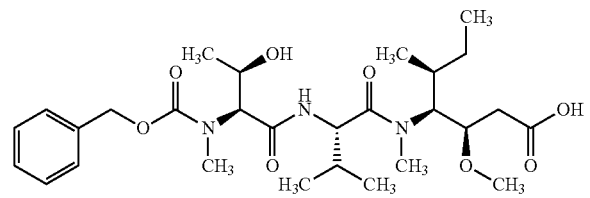 [SMILES: CC[C@H](C)[C@@H]([C@@H](CC(=O)O)OC)N(C)C(=O)[C@@H](NC(=O)[C@H]([C@@H](C)O)N(C)C(=O)OCc1ccccc1)C(C)C]

First, N-[(benzyloxy)carbonyl]-N-methyl-L-threonine was released from 237 mg (0.887 mmol) of its dicyclohexylamine salt by taking the salt up in ethyl acetate and extracting with 5% strength aqueous sulphuric acid. The organic phase was dried over magnesium sulphate, filtered and concentrated. The residue was taken up in 16 ml of DMF, and 365 mg (1 mmol) of tert-butyl (3R,4S,5S)-3-methoxy-5-methyl-4-[methyl(L-valyl)amino]heptanoate (Intermediate 2), 185 mg (0.967 mmol) of 1-(3-dimethylaminopropyl)-3-ethylcarbodiimide hydrochloride and 148 mg (0.967 mmol) of 1-hydroxy-1H-benzotriazole hydrate were added in succession. The mixture was stirred at RT for 2 h. The reaction was then poured into a mixture of semisaturated aqueous ammonium chloride solution and ethyl acetate. The organic phase was separated off, washed successively with saturated sodium bicarbonate solution and saturated sodium chloride solution, dried over magnesium sulphate, filtered and concentrated. The residue was purified by preparative HPLC. This gave 283 mg (53% of theory) of the tert-butyl ester intermediate N-[(benzyloxy)carbonyl]-N-methyl-L-threonyl-N-[(3R,4S,5S)-1-tert-butoxy-3-methoxy-5-methyl-1-oxoheptan-4-yl]-N-methyl-L-valinamide.

HPLC (Method 5): $R_t$=2.17 min.

283 mg (0.466 mmol) of this intermediate were taken up in 5 ml of dichloromethane, 5 ml of anhydrous trifluoroacetic acid were added and the mixture was stirred at RT for 2 h. The reaction was then concentrated under high vacuum, and the residue that remained was purified by preparative HPLC. This gave 156 mg (61% of theory) of the title compound as a colourless foam.

HPLC (Method 5): $R_t$=1.50 min;
LC-MS (Method 2): $R_t$=1.09 min; MS (ESIpos): m/z=552 (M+H)$^+$.

Intermediate 33

(2R)-2-Amino-1-(1,2-oxazinan-2-yl)-3-phenylpropan-1-one, trifluoroacetic acid salt

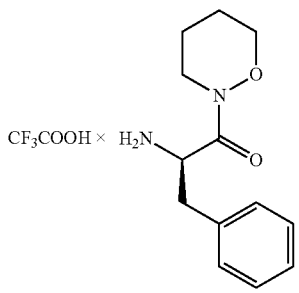 [SMILES: N[C@H](Cc1ccccc1)C(=O)N1CCCCO1]

The title compound was prepared analogously to the synthesis of Intermediate 6 starting with N-(tert-butoxycarbonyl)-D-phenylalanine.

HPLC (Method 6): $R_t$=1.40 min;
LC-MS (Method 1): $R_t$=0.50 min; MS (ESIpos): m/z=235 (M+H)$^+$.

Intermediate 34

(2S)-2-Amino-2-methyl-1-(1,2-oxazinan-2-yl)-3-phenylpropan-1-one, trifluoroacetic acid salt

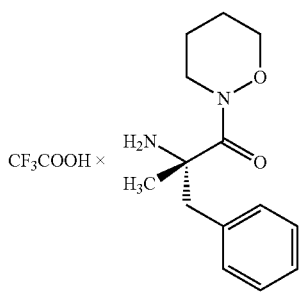 [SMILES: C[C@](N)(Cc1ccccc1)C(=O)N1CCCCO1]

The title compound was prepared analogously to the synthesis of Intermediate 6 starting with commercially available N-(tert-butoxycarbonyl)-α-methyl-L-phenylalanine.

HPLC (Method 5): $R_t$=0.45 min;
LC-MS (Method 2): $R_t$=0.61 min; MS (ESIpos): m/z=249 (M+H)$^+$.

WORKING EXAMPLES

Example 1

N-Methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt 143 mg (0.223 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 15 ml of DMF, and 141 mg (0.22 mmol) of (2R,3R)-3-methoxy-2-methyl-N-[(2S)-1-(1,2-oxazinan-2-yl)-1-oxo-3-phenylpropan-2-yl]-3-[(2S)-pyrrolidin-2-yl]propanamide, trifluoroacetic acid salt (Intermediate 7), 102 mg (0.27 mmol) of O-(7-azabenzotriazol-1-yl)-N,N,N',N'-tetramethyluranium hexafluorophosphate (HATU) and 128 µl (0.74 mmol) of N,N-diisopropylethylamine were added in succession. The mixture was stirred at RT for 3 h. The reaction was then poured into a mixture of semisaturated aqueous ammonium chloride solution and ethyl acetate. The organic phase was separated off, washed successively with saturated sodium bicarbonate solution and saturated sodium chloride solution, dried over magnesium sulphate, filtered and concentrated. This gave 275 mg (quant.) of the Fmoc-protected intermediate N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]-pyrrolidin-1-yl}-5-methyl-1-oxoheptan-4-yl]-N-methyl-L-valinamide.

HPLC (Method 5): $R_t$=2.73 min;
LC-MS (Method 4): $R_t$=3.19 min; MS (ESIpos): m/z=1023 (M+H)$^+$.

46 mg (0.045 mmol) of this intermediate were dissolved in 4 ml of DMF. After addition of 1 ml of piperidine, the mixture was stirred at RT for 1 h. The mixture was then concentrated under reduced pressure and the residue was purified by preparative HPLC (mobile phase: acetonitrile+0.01% TFA/water+0.01% TFA). This gave 22 mg (54% of theory) of the title compound as a colourless foam.

HPLC (Method 5): $R_t$=1.68 min;
LC-MS (Method 2): $R_t$=1.03 min; MS (ESIpos): m/z=801 (M+H)$^+$ $^1$H-NMR (600 MHz, DMSO-d$_6$): δ=8.8 (m, 2H), 8.7 (m, 1H), 8.42 and 8.15 (2d, 1H), 7.3-7.1 (m, 5H), 5.12 and 4.95 (2m, 1H), 4.70 and 4.62 (2m, 1H), 4.62 and 4.50 (2t, 1H), 4.1-3.9 (m, 3H), 3.85 (m, 1H), 3.75-3.6 (m, 2H), 3.23, 3.18, 3.17, 3.14, 3.02 and 2.96 (6s, 9H), 3.1-2.9 and 2.75 (2m, 2H), 2.46 (m, 3H), 2.4-2.1 (m, 2H), 2.05 (br. m, 2H), 1.85-1.55 (br. m, 6H), 1.5-1.2 (br. m, 3H), 1.1-0.8 (m, 18H), 0.75 (t, 3H) [further signals hidden under H$_2$O peak].

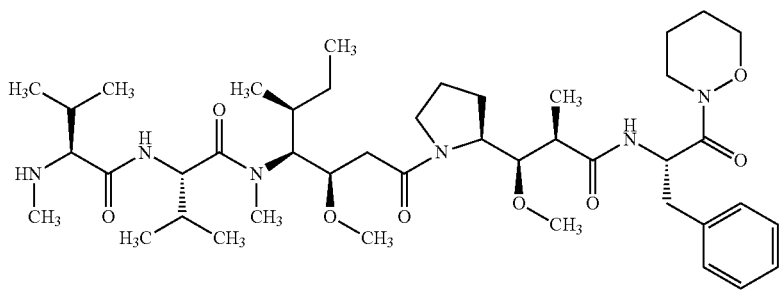

Example 2

N-(2-Hydroxyethyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

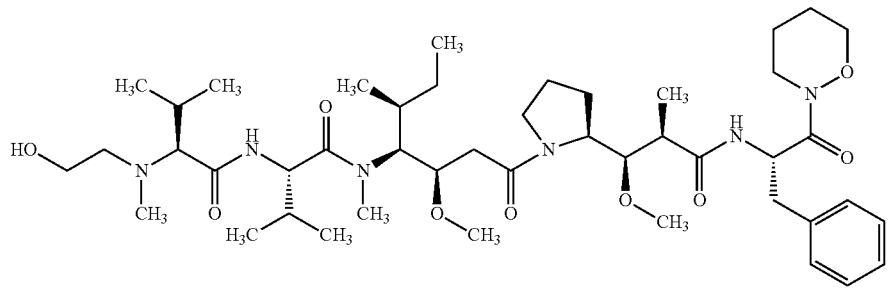 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCO)C(C)C]

50 mg (0.0411 mmol) of N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]-pyrrolidin-1-yl}-5-methyl-1-oxoheptan-4-yl]-N-methyl-L-valinamide, trifluoroacetic acid salt (Example 1) were dissolved in 3 ml of dioxane/water (1:1), and 4.9 mg (0.081 mmol) of dimeric glycolaldehyde were added. 2.8 mg (0.045 mmol) of sodium cyanoborohydride were then added. The mixture was then adjusted to pH 4-5 using 50 µl 0.1 N hydrochloric acid and stirred at 100° C. for 1 h. The reaction was then poured into a mixture of semisaturated aqueous sodium bicarbonate solution and ethyl acetate. The organic phase was separated off, washed with saturated sodium chloride solution, dried over magnesium sulphate, filtered and concentrated. The residue was purified by preparative HPLC. This gave 21 mg (61% of theory) of the title compound in the form of a colourless foam.

HPLC (Method 5): $R_t$=1.69 min;

LC-MS (Method 1): $R_t$=0.92 min; MS (ESIpos): m/z=845 (M+H)$^+$ $^1$H-NMR (600 MHz, DMSO-d$_6$): δ=9.2 (m, 1H), 8.9 (m, 1H), 8.4 and 8.15 (2d, 1H), 7.3-7.1 (m, 5H), 5.12 and 4.95 (2m, 1H), 4.70 and 4.62 (2m, 1H), 4.62 and 4.55 (2t, 1H), 4.1-3.9 (m, 3H), 3.9-3.7 (m, 5H), 3.23, 3.18, 3.17, 3.15, 3.02 and 2.98 (6s, 9H), 2.95 and 2.75 (2m, 2H), 2.8 (m, 3H), 2.46-2.00 (m, 4H), 1.85-1.55 (br. m, 6H), 1.5-1.2 (br. m, 3H), 1.1-0.8 (m, 18H), 0.75 (t, 3H) [further signals hidden under H$_2$O peak].

Example 3

N,N-Dimethyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

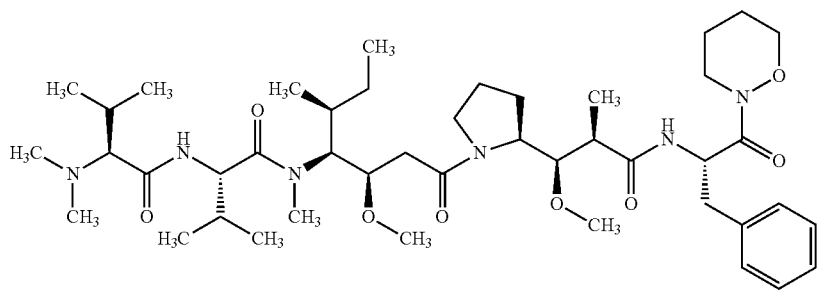 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)C)C(C)C]

20 mg (0.022 mmol) of N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt (Example 1) were dissolved in 1 ml of DMF, 3.4 mg (1 µl) of iodomethane and 7.6 mg (0.055 mmol) of potassium carbonate were added and the mixture was stirred at RT for 1 h. The same amount of potassium carbonate was then added, and the reaction was treated in an ultrasonic bath for 10 min. The solvent was then distilled off under reduced pressure, and the residue that remained was purified by preparative HPLC. This gave 8 mg (44% of theory) of the title compound.

HPLC (Method 5): $R_t$=1.71 min;

LC-MS (Method 2): $R_t$=1.04 min; MS (ESIpos): m/z=815 (M+H)$^+$

¹H-NMR (600 MHz, DMSO-d₆): δ=9.55 (m, 1H), 8.9-8.7 (m, 1H), 8.45 and 8.15 (2d, 1H), 7.3-7.1 (m, 5H), 5.12 and 4.95 (2m, 1H), 4.70 and 4.62 (2m, 1H), 4.62 and 4.55 (2t, 1H), 4.1-3.9 (m, 3H), 3.9-3.6 (m, 3H), 3.55 (m, 2H), 3.23, 3.18, 3.17, 3.15, 3.02 and 2.98 (6s, 9H), 2.95 and 2.7 (2m, 2H), 2.8-2.7 (2 br. s, 6H), 2.46-2.00 (m, 4H), 1.85-1.55 (br. m, 6H), 1.5-1.2 (br. m, 3H), 1.1-0.8 (m, 18H), 0.75 (t, 3H) [further signals hidden under H₂O peak].

added in succession. The mixture was stirred at RT overnight. The reaction was then poured into a mixture of semisaturated aqueous ammonium chloride solution and ethyl acetate. The organic phase was separated off, washed successively with saturated sodium bicarbonate solution and saturated sodium chloride solution, dried over magnesium sulphate, filtered and concentrated. This gave 220 mg (quant.) of the Fmoc-protected intermediate N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide.

HPLC (Method 5): R$_t$=2.77 min;
LC-MS (Method 1): R$_t$=1.5 min; MS (ESIpos): m/z=1037 (M+H)⁺.

220 mg (0.212 mmol) of this intermediate were dissolved in 5 ml of DMF. After addition of 1 ml of piperidine, the mixture was stirred at RT for 1 h. The mixture was then concentrated under reduced pressure and the residue was purified by preparative HPLC (mobile phase: acetonitrile+0.01% TFA/water+0.01% TFA). This gave 91 mg (46% of theory) of the title compound as a colourless foam.

Example 4

N-Methyl-L-valyl-N-[(3R,4S,5S)-3-methoxy-1-{(2S)-2-[(1R,2R)-1-methoxy-2-methyl-3-{[(2S,3S)-1-(1,2-oxazinan-2-yl)-1-oxo-3-phenylbutan-2-yl]amino}-3-oxopropyl]pyrrolidin-1-yl}-5-methyl-1-oxoheptan-4-yl]-N-methyl-L-valinamide, trifluoroacetic acid salt

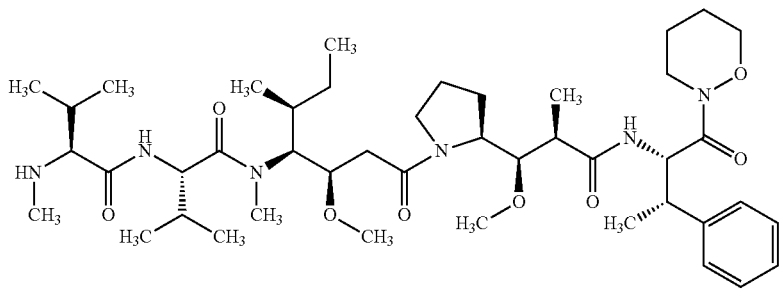

× CF₃COOH 126 mg (0.198 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 10 ml of DMF, and 105 mg (0.198 mmol) of (2R,3R)-3-methoxy-2-methyl-N-[(2S,3S)-1-(1,2-oxazinan-2-yl)-1-oxo-3-phenylbutan-2-yl]-3-[(2S)-pyrrolidin-2-yl]propanamide, trifluoroacetic acid salt (Intermediate 17), 41.6 mg (0.217 mmol) of 1-(3-dimethylaminopropyl)-3-ethylcarbodiimide hydrochloride, 33 mg (0.217 mmol) of 1-hydroxy-1H-benzotriazole hydrate and 79 nl (0.454 mmol) of N,N-diisopropylethylamine were HPLC (Method 5): R$_t$=1.71 min;
LC-MS (Method 1): R$_t$=0.9 min; MS (ESIpos): m/z=815 (M+H)⁺

¹H-NMR (600 MHz, DMSO-d₆): δ=8.87 and 8.80 (2d, 2H), 8.75 (m, 1H), 8.40 and 7.98 (2d, 1H), 7.3-7.1 (m, 5H), 5.45 and 5.2 (2t, 1H), 4.78 and 4.62 (2m, 1H), 4.73 and 4.58 (2t, 1H), 4.2-4.0 (m, 3H), 3.7-3.6 (m, 1H), 3.35, 3.20, 3.18, 3.14, 3.12 and 3.00 (6s, 9H), 3.1 and 2.95 (2m, 2H), 2.46 (m, 3H), 2.4-2.0 (m, 4H), 1.9-1.6 (m, 4H), 1.6-1.2 (m, 5H), 1.1-0.75 (m, 21H), 0.80 (t, 3H) [further signals hidden under H₂O peak].

Example 5

N-Methyl-L-valyl-N-[(3R,4S,5S)-3-methoxy-1-
{(2S)-2-[(1R,2R)-1-methoxy-2-methyl-3-{[(2S)-1-
(1,2-oxazolidin-2-yl)-1-oxo-3-phenylpropan-2-yl]
amino}-3-oxopropyl]pyrrolidin-1-yl}-5-methyl-1-
oxoheptan-4-yl]-N-methyl-L-valinamide,
trifluoroacetic acid salt

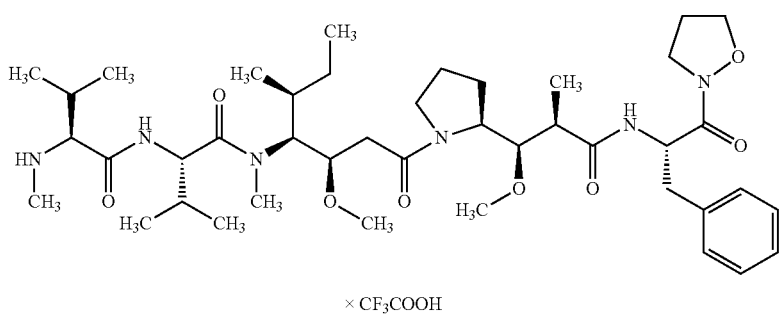 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCO1)OC)N(C)C(=O)[C@@H](NC(=O)[C@@H](NC)C(C)C)C(C)C]

138 mg (0.216 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 14 ml of DMF, and 109 mg (0.216 mmol) of (2R,3R)-3-methoxy-2-methyl-N-[(2S)-1-(1,2-oxazolidin-2-yl)-1-oxo-3-phenylpropan-2-yl]-3-[(2S)-pyrrolidin-2-yl]propanamide, trifluoroacetic acid salt (Intermediate 15), 45.6 mg (0.238 mmol) of 1-(3-dimethylaminopropyl)-3-ethylcarbodiimide hydrochloride, 36.5 mg (0.38 mmol) of 1-hydroxy-1H-benzotriazole hydrate and 49 µl (0.281 mmol) of N,N-diisopropylethylamine were added in succession. The mixture was stirred at RT overnight. The reaction was then poured into a mixture of semisaturated aqueous ammonium chloride solution and ethyl acetate. The organic phase was separated off, washed successively with saturated sodium bicarbonate solution and saturated sodium chloride solution, dried over magnesium sulphate, filtered and concentrated. This gave 170 mg (78% of theory) of the Fmoc-protected intermediate N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(2S)-1-(1,2-oxazolidin-2-yl)-1-oxo-3-phenylpropan-2-yl]amino}-3-oxopropyl]pyrrolidin-1-yl}-5-methyl-1-oxoheptan-4-yl]-N-methyl-L-valinamide.

HPLC (Method 5): $R_t$=2.64 min;

LC-MS (Method 1): $R_t$=1.44 min; MS (ESIpos): m/z=1009 (M+H)$^+$.

170 mg (0.168 mmol) of this intermediate were dissolved in 5 ml of DMF. After addition of 1 ml of piperidine, the mixture was stirred at RT for 1 h. The mixture was then concentrated under reduced pressure and the residue was purified by preparative HPLC (mobile phase: acetonitrile+0.01% TFA/water+0.01% TFA). This gave 37 mg (24% of theory) of the title compound as a colourless foam.

HPLC (Method 5): $R_t$=1.57 min;

LC-MS (Method 1): $R_t$=0.84 min; MS (ESIpos): m/z=787 (M+H)$^+$ $^1$H-NMR (600 MHz, DMSO-$d_6$): δ=8.9-8.7 (m, 3H), 8.5 and 8.2 (2m, 1H), 7.3-7.1 (m, 5H), 5.6 and 5.4 (2m, 1H), 4.7 and 4.6 (2m, 1H), 4.65 and 4.55 (2t, 1H), 4.0-3.9 (m, 3H), 3.75-3.6 (m, 2H), 3.23, 3.20, 3.15, 3.05 and 2.98 (5s, 9H), 3.0 and 2.7 (2m, 2H), 2.46 (m, 3H), 2.35-2.15 (m, 4H), 2.1-2.0 (m, 2H), 1.85-1.6 (m, 3H), 1.45 (m, 1H), 1.25 (m, 1H), 1.1-0.85 (m, 18H), 0.75 (t, 3H) [further signals hidden under $H_2O$ peak].

Example 6

N-Methyl-L-valyl-N-[(3R,4S,5S)-3-methoxy-1-{(2S)-2-[(1R,2R)-1-methoxy-2-methyl-3-{[(2S)-1-(2-oxa-3-azabicyclo[2.2.2]oct-5-en-3-yl)-1-oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt

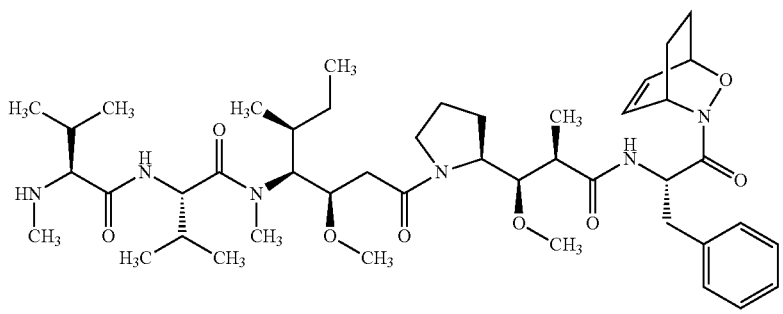

× CF$_3$COOH 44.5 mg (0.071 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 10 ml of DMF, and 38.6 mg (0.071 mmol) of (2R,3R)-3-methoxy-2-methyl-N-[(2S)-1-(2-oxa-3-azabicyclo[2.2.2]oct-5-en-3-yl)-1-oxo-3-phenylpropan-2-yl]-3-[(2S)-pyrrolidin-2-yl]propanamide, trifluoroacetic acid salt (Intermediate 9), 32.5 mg (0.086 mmol) of O-(7-azabenzotriazol-1-yl)-N,N,N',N'-tetramethyluranium hexafluorophosphate (HATU) and 41 µl (0.235 mmol) of N,N-diisopropylethylamine were added in succession. The mixture was stirred at RT for 1 h. The reaction was then concentrated under reduced pressure and the residue was taken up in ethyl acetate. The organic phase was washed successively with 5% strength citric acid solution and 5% strength sodium bicarbonate solution, dried over magnesium sulphate, filtered and concentrated. This gave 73 mg (98% of theory) of the Fmoc-protected intermediate N-[(9H-fluoren-9-yl-methoxy)carbonyl]-N-methyl-L-valyl-N-[(3R,4S,5S)-3-methoxy-1-{(2S)-2-[(1R,2R)-1-methoxy-2-methyl-3-{[(2S)-1-(2-oxa-3-azabicyclo[2.2.2]oct-5-en-3-yl)-1-oxo-3-phenylpropan-2-yl]amino}-3-oxopropyl]pyrrolidin-1-yl}-5-methyl-1-oxoheptan-4-yl]-N-methyl-L-valinamide.

HPLC (Method 6): $R_t$=2.78 min;

LC-MS (Method 3): $R_t$=2.96 min; MS (ESIpos): m/z=1047 (M+H)$^+$.

73 mg (0.071 mmol) of this intermediate were dissolved in 5 ml of DMF. After addition of 0.5 ml of piperidine, the reaction was stirred at RT for 10 min. The mixture was then concentrated under reduced pressure and the residue was digested repeatedly with diethyl ether. After the ether had been decanted, the residue was purified by preparative HPLC (mobile phase: acetonitrile/0.1% aq. TFA). This gave 16 mg (26% of theory) of the title compound as a colourless foam.

HPLC (Method 6): $R_t$=1.94 min;

LC-MS (Method 3): $R_t$=1.71 min; MS (ESIpos): m/z=825 (M+H)$^+$ $^1$H-NMR (400 MHz, DMSO-d$_6$): δ=8.9-8.6 (m, 3H), 8.4, 8.3, 8.1 and 8.0 (4d, 1H), 7.3-7.1 (m, 5H), 6.7-6.5 (m, 2H), 5.2-4.8 (m, 3H), 4.75-4.55 (m, 3H), 4.05-3.95 (m, 1H), 3.7-3.4 (m, 4H), 3.22, 3.17, 3.15, 3.05, 3.02 and 2.95 (6s, 9H), 3.0 and 2.7 (2 br. m, 2H), 2.46 (m, 3H), 2.4-1.2 (br. m, 13H), 1.1-0.85 (m, 18H), 0.75 (m, 3H) [further signals hidden under H$_2$O peak].

Example 7

N-Methyl-L-valyl-N-[(3R,4S,5S)-1-{(2S)-2-[(1R,2R)-3-{[(2S)-3-(4-hydroxy-3-nitrophenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt

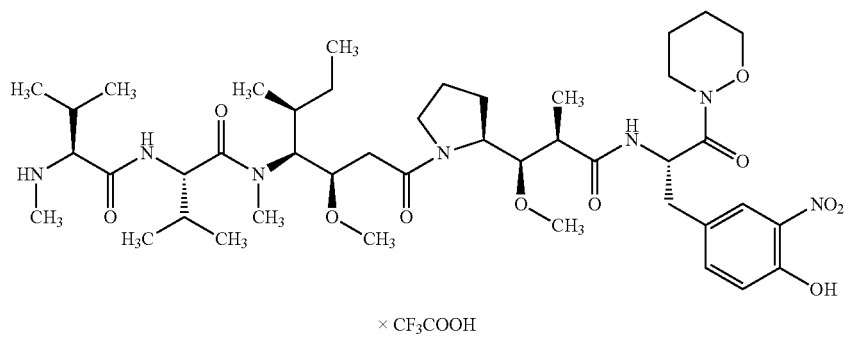 [SMILES: CC[C@H](C)[C@@H]([C@@H](CC(=O)N1CCC[C@H]1[C@H](OC)[C@@H](C)C(=O)N[C@@H](Cc1ccc(O)c([N+](=O)[O-])c1)C(=O)N1CCCCO1)OC)N(C)C(=O)[C@@H](NC(=O)[C@@H](NC)C(C)C)C(C)C]

× CF₃COOH 160 mg (0.251 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 13 ml of DMF, and 145 mg (0.251 mmol) of (2R,3R)—N-[(2S)-3-(4-hydroxy-3-nitrophenyl)-1-(1,2-oxazinan-2-yl)-1-oxopropan-2-yl]-3-methoxy-2-methyl-3-[(2S)-pyrrolidin-2-yl]propanamide, trifluoroacetic acid salt (Intermediate 19), 53 mg (0.276 mmol) of 1-(3-dimethylaminopropyl)-3-ethylcarbodiimide hydrochloride, 42.2 mg (0.276 mmol) of 1-hydroxy-1H-benzotriazole hydrate and 65 µl (0.376 mmol) of N,N-diisopropylethylamine were added in succession. The mixture was stirred at RT overnight. The reaction was then poured into a mixture of semisaturated aqueous ammonium chloride solution and ethyl acetate. The organic phase was separated off, washed successively with saturated sodium bicarbonate solution and saturated sodium chloride solution, dried over magnesium sulphate, filtered and concentrated. This gave 260 mg (96% of theory) of the crude Fmoc-protected intermediate N-[(9H-fluoren-9-ylmethoxy)carbonyl]-N-methyl-L-valyl-N-[(3R,4S,5S)-1-{(2S)-2-[(1R,2R)-3-{[(2S)-3-(4-hydroxy-3-nitrophenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide which was used without further purification for the next step.

260 mg (0.24 mmol) of this intermediate were dissolved in 3 ml of DMF. After addition of 0.6 ml of piperidine, the mixture was stirred at RT for 1 h. The mixture was then concentrated under reduced pressure and the residue was purified by preparative HPLC (mobile phase: acetonitrile+ 0.01% TFA/water+0.01% TFA). This gave 105 mg (45% of theory) of the title compound as a slightly yellowish foam.

HPLC (Method 5): $R_t$=1.62 min;

LC-MS (Method 1): $R_t$=0.87 min; MS (ESIpos): m/z=862 (M+H)⁺

¹H-NMR (500 MHz, DMSO-d₆): δ=10.85 and 10.72 (2s, 1H), 8.9-8.6 (m, 3H), 8.45 and 8.2 (2d, 1H), 7.70 and 7.72 (2s, 1H), 7.40 and 7.32 (2d, 1H), 7.01 and 7.00 (2d, 1H), 5.0-4.85 (m, 1H), 4.7-4.5 (m, 2H), 4.15-4.0 (m, 2H), 3.95-3.75 (m, 2H), 3.7-3.6 (m, 2H), 3.28, 3.21, 3.16, 3.15, 3.02 and 2.96 (6s, 9H), 2.9 and 2.75 (2m, 2H), 2.46 (m, 3H), 2.4-2.3 (m, 1H), 2.3-2.2 (m, 1H), 2.1-1.95 (br. m, 2H), 1.85-1.7 (m, 4H), 1.7-1.55 (m, 2H), 1.55-1.35 (m, 2H), 1.35 (m, 1H), 1.1-0.8 (m, 18H), 0.75 (t, 3H) [further signals hidden under H₂O peak].

Example 8

N-Methyl-L-valyl-N-[(3R,4S,5S)-1-{(2S)-2-[(1R,2R)-3-{[(2S)-1-(1,4-dihydro-3H-2,3-benzoxazin-3-yl)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt

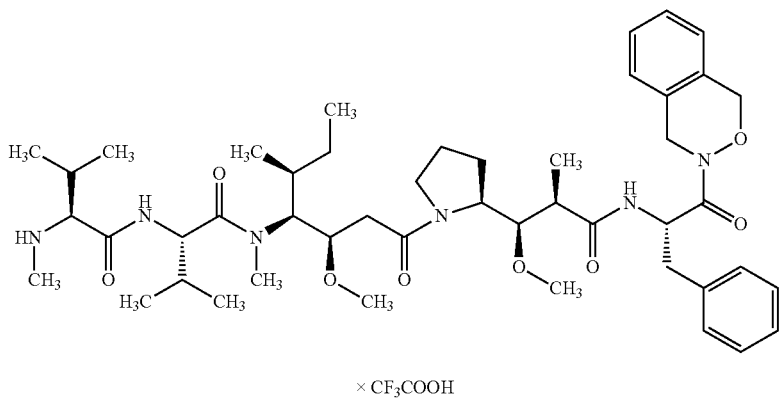 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1Cc2ccccc2CO1)OC)N(C)C(=O)[C@@H](NC(=O)[C@@H](NC)C(C)C)C(C)C]

× CF₃COOH 15.8 mg (0.025 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 5 ml of DMF, and 14 mg (0.025 mmol) of (2R,3R)—N-[(2S)-1-(1,4-dihydro-3H-2,3-benzoxazin-3-yl)-1-oxo-3-phenylpropan-2-yl]-3-methoxy-2-methyl-3-[(2S)-pyrrolidin-2-yl]propanamide, trifluoroacetic acid salt (Intermediate 11), 11.3 mg (0.03 mmol) of O-(7-azabenzotriazol-1-yl)-N,N,N',N'-tetramethyluranium hexafluorophosphate (HATU) and 14 µl (0.082 mmol) of N,N-diisopropylethylamine were added in succession. The mixture was stirred at RT for 10 min. The reaction was then concentrated under reduced pressure and the residue was purified directly by preparative HPLC. This gave 13 mg (49% of theory) of the Fmoc-protected intermediate N-[(9H-fluoren-9-ylmethoxy)carbonyl]-N-methyl-L-valyl-N-[(3R,4S,5S)-1-{(2S)-2-[(1R,2R)-3-{[(2S)-1-(1,4-dihydro-3H-2,3-benzoxazin-3-yl)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide.

HPLC (Method 6): $R_t$=2.93 min;
LC-MS (Method 3): $R_t$=3.10 min; MS (ESIpos): m/z=1071 (M+H)⁺.

13 mg (0.012 mmol) of this intermediate were dissolved in 2 ml of DMF. After addition of 0.5 ml of piperidine, the mixture was stirred at RT for 10 min. The mixture was then concentrated under reduced pressure and the residue was purified by preparative HPLC (mobile phase: acetonitrile/0.1% aq. TFA). This gave 10 mg (97% of theory) of the title compound.

HPLC (Method 6): $R_t$=2.10 min;
LC-MS (Method 1): $R_t$=0.97 min; MS (ESIpos): m/z=849 (M+H)⁺

¹H-NMR (400 MHz, DMSO-d₆): δ=8.90-8.62 (m, 3H), 8.60 and 8.33 (2d, 1H), 7.35-7.1 (m, 9H), 5.4-5.0 (m, 4H), 4.7-4.5 (m, 3H), 3.95 (m, 1H), 3.7-3.4 (m, 3H), 3.24, 3.20, 3.18, 3.16, 3.10 and 3.08 (6s, 9H), 3.0 and 2.85 (2 br. m, 2H), 2.46 (m, 3H), 2.3 (br. m, 2H), 2.05 (br. m, 2H), 1.9-1.6 (m, 3H), 1.5-1.2 (br. m, 2H), 1.1-0.85 (m, 18H), 0.75 (m, 3H) [further signals hidden under H₂O peak].

Example 9

N-Methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt

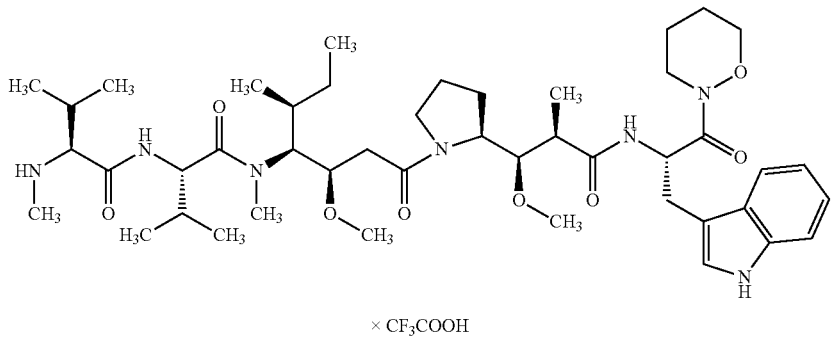 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@@H](NC)C(C)C)C(C)C]

× CF$_3$COOH 40 mg (0.076 mmol) of N-(tert-butoxycarbonyl)-N-methyl-L-valyl-N-[(2R,3S,4S)-1-carboxy-2-methoxy-4-methylhexan-3-yl]-N-methyl-L-valinamide (Intermediate 20) were taken up in 5 ml of DMF, and 43 mg (0.078 mmol) of (2R,3R)—N-[(2S)-3-(1H-indol-3-yl)-1-(1,2-oxazinan-2-yl)-1-oxopropan-2-yl]-3-methoxy-2-methyl-3-[(2S)-pyrrolidin-2-yl]propanamide, trifluoroacetic acid salt (Intermediate 13), 35 mg (0.093 mmol) of O-(7-azabenzotriazol-1-yl)-N,N,N',N'-tetramethyluronium hexafluorophosphate (HATU) and 45 µl (0.256 mmol) of N,N-diisopropylethylamine were added in succession. The mixture was stirred at RT for 2 h. The reaction was concentrated under reduced pressure and the residue was purified directly by preparative HPLC. This gave 10 mg (14% of theory) of the Boc-protected intermediate N-(tert-butoxycarbonyl)-N-methyl-L-valyl-N-[(3R,4S,5S)-1-{(2S)-2-[(1R,2R)-3-{[(2S)-3-(1H-indol-3-yl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide.

HPLC (Method 6): R$_t$=2.52 min;
LC-MS (Method 1): R$_t$=1.35 min; MS (ESIpos): m/z=940 (M+H)$^+$.

5 mg (0.005 mmol) of this intermediate were dissolved in 3 ml of dichloromethane. After addition of 0.5 ml of trifluoroacetic acid, the reaction was treated in an ultrasonic bath for 30 min and then stirred at RT for a further 30 min. The mixture was then concentrated under reduced pressure, acetonitrile was added to the residue and the mixture was concentrated again. Lyophilization from dioxane/water gave 5 mg (99% of theory) of the title compound.

HPLC (Method 6): R$_t$=1.94 min;
LC-MS (Method 2): R$_t$=0.99 min; MS (ESIpos): m/z=840 (M+H)$^+$ $^1$H-NMR (400 MHz, DMSO-d$_6$): δ=10.8 and 8.8 (2m, 3H), 8.35 and 8.05 (2d, 1H), 7.55 (m, 1H), 7.3 (d, 1H), 7.20-6.91 (m, 3H), 5.12 and 4.95 (2m, 1H), 4.7-4.5 (m, 2H), 4.1-3.9 (m, 2H), 3.85 (m, 2H), 3.75-3.4 (m, 5H), 3.21, 3.15, 3.14, 3.10, 2.95 and 2.85 (6s, 9H), 2.46 (m, 3H), 2.4-2.2 (m, 2H), 2.1-1.9 (m, 2H), 1.85-1.65 (m, 4H), 1.65-1.2 (m, 3H), 1.05 and 1.0 (2d, 3H), 0.95-0.8 (m, 15H), 0.75 (m, 3H) [further signals hidden under H$_2$O peak].

Example 10

N-Methyl-L-valyl-N-[(3R,4S,5S)-1-{(2S)-2-[(1R,2R)-3-{[(2S)-3-(4-hydroxy-3-nitrophenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide hydrochloride

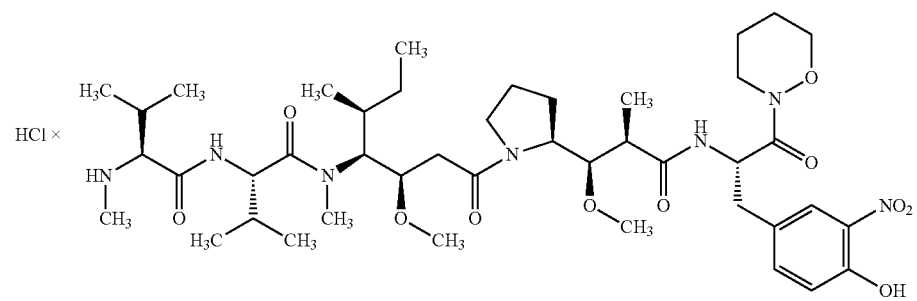 [SMILES: CC[C@H](C)[C@@H]([C@@H](CC(=O)N1CCC[C@H]1[C@H](OC)[C@@H](C)C(=O)N[C@@H](Cc1ccc(O)c([N+](=O)[O-])c1)C(=O)N1CCCCO1)OC)N(C)C(=O)[C@@H](NC(=O)[C@@H](NC)C(C)C)C(C)C]

25 mg (0.026 mmol) of N-methyl-L-valyl-N-[(3R,4S,5S)-1-{(2S)-2-[(1R,2R)-3-{[(2S)-3-(4-hydroxy-3-nitrophenyl)-1-(1,2-oxazinan-2-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (Example 7) were dissolved in 2 ml of 1 N hydrochloric acid and then lyophilized This gave 16.4 mg (71% of theory) of the title compound as a slightly yellowish foam.

HPLC (Method 5): $R_t$=1.63 min;
LC-MS (Method 1): $R_t$=0.87 min; MS (ESIpos): m/z=862 (M+H)$^+$.

Example 11

N-Methyl-L-valyl-N-[(3R,4S,5S)-1-{(2S)-2-[(1R,2R)-3-({(2S)-1-[4-(benzyloxy)-1,2-oxazolidin-2-yl]-1-oxo-3-phenylpropan-2-yl}amino)-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (Diastereomer 1)

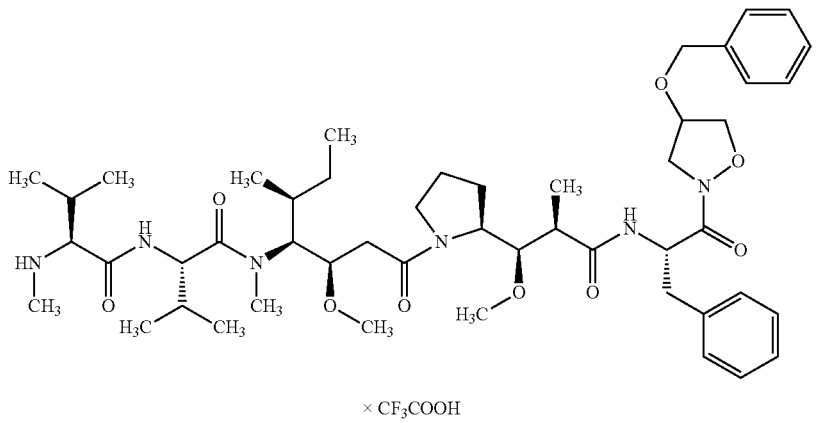 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CC(OCc2ccccc2)CO1)OC)N(C)C(=O)[C@@H](NC(=O)[C@@H](NC)C(C)C)C(C)C]

× CF$_3$COOH

The title compound was prepared analogously to the synthesis of Example 8 by coupling Starting Material 1 with Intermediate 28, subsequent deprotection with trifluoroacetic acid, then coupling with Intermediate 4 and finally deprotection with piperidine. Purification of the end product was carried out by preparative HPLC (mobile phase: acetonitrile/0.1% aq. TFA). This gave 16.4 mg of the title compound.

HPLC (Method 5): $R_t$=2.08 min;

LC-MS (Method 3): $R_t$=1.90 min; MS (ESIpos): m/z=893 (M+H)$^+$ $^1$H-NMR (400 MHz, DMSO-d$_6$): δ=8.8-8.6 (m, 3H), 8.45 and 8.4 (2d, 1H), 7.35-7.1 (m, 10H), 5.2 and 5.0 (2m, 1H), 4.7-4.5 (m, 5H), 4.15 (d, 1H), 4.0-3.6 (m, 5H), 3.6-3.4 (m, 2H), 3.75-3.4 (m, 5H), 3.22, 3.16, 3.15, 3.05 and 2.96 (5s, 9H), 3.1-2.9 and 2.8-2.6 (2m, 2H), 2.45 and 2.44 (2s, 3H), 2.4-2.2 (m, 2H), 2.1-2.0 (m, 2H), 1.85-1.6 (m, 2H), 1.5-1.2 (m, 3H), 1.1-0.8 (m, 18H), 0.75 (m, 3H).

Example 12

N-Methyl-L-valyl-N-[(3R,4S,5S)-1-{(2S)-2-[(1R,2R)-3-({(2S)-1-[4-(benzyloxy)-1,2-oxazolidin-2-yl]-1-oxo-3-phenylpropan-2-yl}amino)-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (Diastereomer 2)

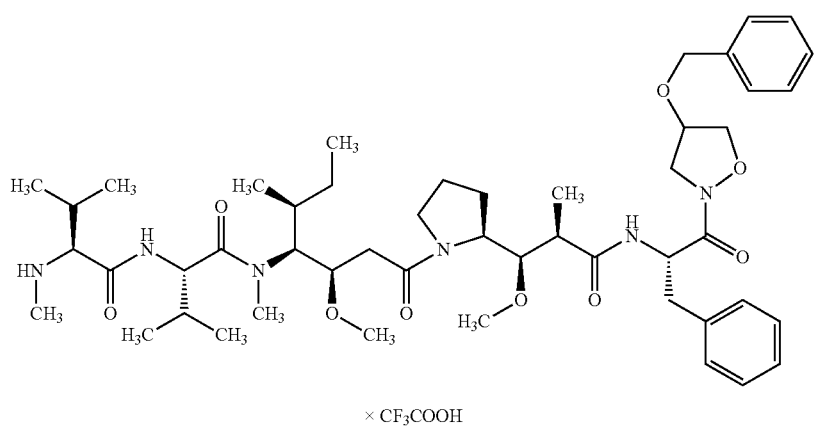 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CC(OCc2ccccc2)CO1)OC)N(C)C(=O)[C@@H](NC(=O)[C@@H](NC)C(C)C)C(C)C]

× CF₃COOH

The title compound was prepared analogously to the synthesis of Example 8 by coupling Starting Material 1 with Intermediate 29, subsequent deprotection with trifluoroacetic acid, then coupling with Intermediate 4 and finally deprotection with piperidine. Purification of the end product was carried out by preparative HPLC (mobile phase: acetonitrile/0.1% aq. TFA). This gave 28 mg of the title compound.

HPLC (Method 5): $R_t$=2.11 min;

LC-MS (Method 7): $R_t$=1.96 min; MS (ESIpos): m/z=893 (M+H)⁺

¹H-NMR (400 MHz, DMSO-d₆): δ=8.9-8.6 (m, 3H), 8.45 and 8.3 (2d, 1H), 7.4-7.1 (m, 10H), 5.2 and 4.95 (2m, 1H), 4.7-4.5 (m, 5H), 4.25 (d, 1H), 4.0-3.8 (m, 3H), 3.7-3.6 (m, 2H), 3.6-3.4 (m, 2H), 3.23, 3.19, 3.18, 3.15, 3.05 and 2.96 (6s, 9H), 3.1-3.0 and 2.8-2.65 (2m, 2H), 2.5-2.4 (m, 3H), 2.35-2.15 (m, 2H), 2.1-1.95 (m, 2H), 1.8-1.6 (m, 2H), 1.5-1.2 (m, 3H), 1.1-0.8 (m, 18H), 0.75 (m, 3H).

Example 13

N-Methyl-L-valyl-N-[(3R,4S,5S)-1-{(2S)-2-[(1R,2R)-3-{[(2S)-1-(4-hydroxy-1,2-oxazolidin-2-yl)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (Diastereomer 2)

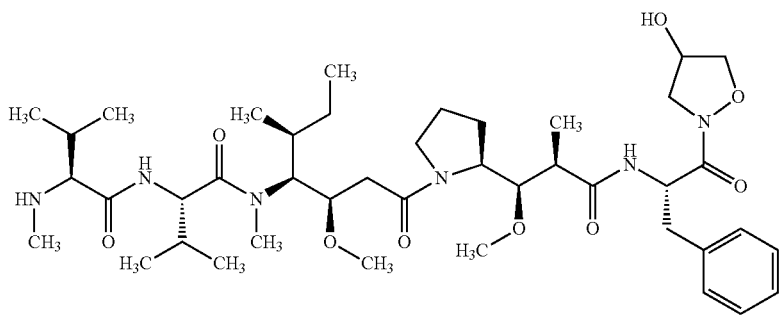 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CC(O)CO1)OC)N(C)C(=O)[C@@H](NC(=O)[C@@H](NC)C(C)C)C(C)C]

27 mg (0.03 mmol) of the compound from Example 12 were taken up in a mixture of 42 ml of THF and 22 ml of water, 1.35 ml of 2M hydrochloric acid were added and the mixture was hydrogenated for 20 min at RT and atmospheric pressure over 10% palladium/carbon. The catalyst was then filtered off and the reaction mixture was neutralized with aqueous sodium bicarbonate solution. The mixture was then extracted with ethyl acetate. After separation of the phases, the ethyl acetate phase was concentrated and the residue was purified by flash chromatography on silica gel using the mobile phase dichloromethane/methanol/17% aq ammonia (125:3:0.3). The appropriate fractions were concentrated and the residue was lyophilized from dioxane. This gave 25 mg of the title compound.

HPLC (Method 6): $R_t$=1.74 min;

LC-MS (Method 8): $R_t$=2.06 min; MS (ESIpos): m/z=803 (M+H)$^+$ $^1$H-NMR (400 MHz, DMSO-d$_6$): δ=8.45 and 8.2 (2d, 1H), 8.1 (m, 1H), 7.3-7.1 (m, 5H), 5.5 (m, 1H), 5.15 and 4.95 (2m, 1H), 4.7-4.4 (m, 3H), 4.1-3.9 (m, 3H), 3.5-3.4 (m, 3H), 3.23, 3.19, 3.18, 3.16, 3.05 and 2.96 (6s, 9H), 3.1-3.0 and 2.8-2.65 (2m, 2H), 2.4-2.15 (m, 5H), 2.1-1.95 (m, 2H), 1.8-1.6 (m, 3H), 1.5-1.2 (m, 2H), 1.05-0.8 (m, 18H), 0.75 (m, 3H).

Example 14

N-Methyl-L-valyl-N-[(3R,4S,5S)-1-{(2S)-2-[(1R,2R)-3-{[(2S)-3,3-dimethyl-1-(1,2-oxazinan-2-yl)-1-oxobutan-2-yl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt

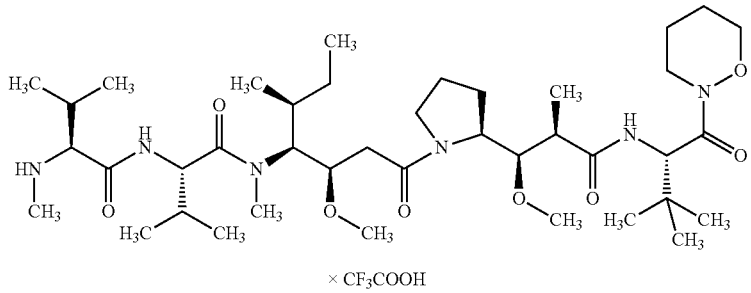 [SMILES: CC[C@H](C)[C@@H]([C@@H](CC(=O)N1CCC[C@H]1[C@H](OC)[C@@H](C)C(=O)N[C@H](C(=O)N1CCCCO1)C(C)(C)C)OC)N(C)C(=O)[C@@H](NC(=O)[C@@H](NC)C(C)C)C(C)C]

The title compound was prepared in three steps starting with Intermediate 21, first by deprotecting with trifluoroacetic acid, followed by coupling with Intermediate 4 and finally deprotecting with piperidine. Purification of the end product was carried out by preparative HPLC (mobile phase: acetonitrile+0.01% TFA/water+0.01% TFA). This gave 2.5 mg of the title compound.

HPLC (Method 5): $R_t$=1.67 min;
LC-MS (Method 1): $R_t$=0.90 min; MS (ESIpos): m/z=767 (M+H)$^+$.

Example 15

N-Methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3,3-diphenylpropan-2-yl]amino}-3-oxopropyl]pyrrolidin-1-yl}-5-methyl-1-oxoheptan-4-yl]-N-methyl-L-valinamide, trifluoroacetic acid salt

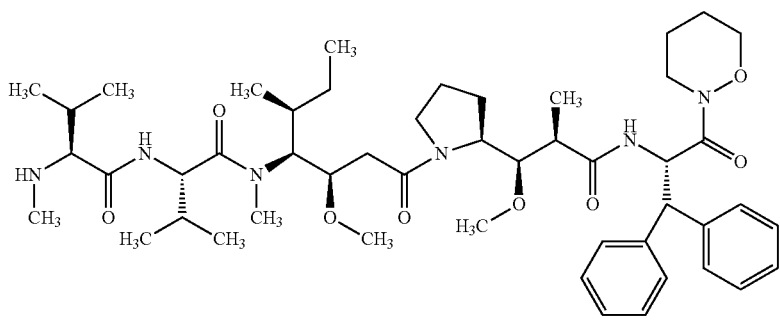

The title compound was prepared in three steps starting with Intermediate 22, first by deprotecting with trifluoroacetic acid, followed by coupling with Intermediate 4 and finally deprotecting with piperidine. Purification of the end product was carried out by preparative HPLC (mobile phase: acetonitrile+0.01% TFA/water+0.01% TFA). This gave 20 mg of the title compound.

HPLC (Method 5): R$_t$=1.78 min;
LC-MS (Method 1): R$_t$=0.95 min; MS (ESIpos): m/z=877 (M+H)$^+$.

Example 16

N-Methyl-L-valyl-N-[(3R,4S,5S)-3-methoxy-1-{(2S)-2-[(1R,2R)-1-methoxy-2-methyl-3-{[(1S,2S)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide, trifluoroacetic acid salt

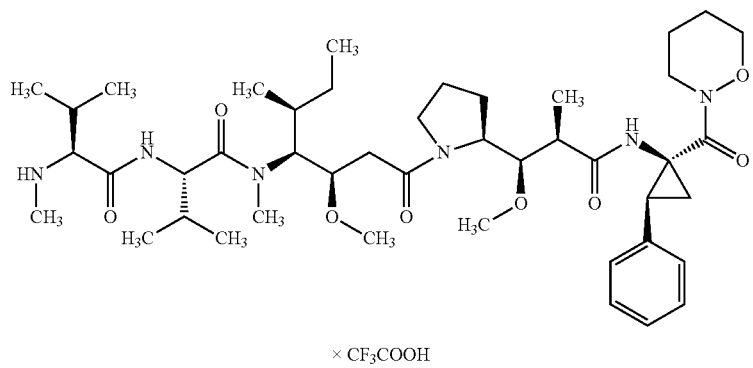 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@H]1c1ccccc1)OC)N(C)C(=O)[C@@H](NC(=O)[C@@H](NC)C(C)C)C(C)C]

× CF$_3$COOH

The title compound was prepared in three steps starting with Intermediate 23, first by deprotecting with trifluoroacetic acid, followed by coupling with Intermediate 4 and finally deprotecting with piperidine. Purification of the end product was carried out by preparative HPLC (mobile phase: acetonitrile/0.1% aq. TFA). This gave 9 mg of the title compound.

HPLC (Method 6): R$_t$=1.95 min;

LC-MS (Method 1): R$_t$=0.90 min; MS (ESIpos): m/z=813 (M+H)$^+$.

$^1$H-NMR (500 MHz, DMSO-d$_6$): δ=8.85 (m, 2H), 8.7 (m, 1H), 8.2 and 7.8 (2s, 1H), 7.3-7.1 (m, 5H), 4.75 and 4.65 (2m, 1H), 4.7 and 4.6 (2t, 1H), 4.0-3.9 (m, 2H), 3.85 (m, 1H), 3.75-3.6 (m, 4H), 3.55 (m, 1H), 3.22, 3.20, 3.18, 3.17, 3.03 and 2.98 (6s, 9H), 2.92 and 2.82 (2t, 1H), 2.5-2.45 (m, 3H), 2.4-1.3 (m, 15H), 1.0-0.7 (m, 18H), 0.65 and 0.6 (2d, 3H) [further signals hidden under H$_2$O peak].

Example 17

N-Methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide, trifluoroacetic acid salt

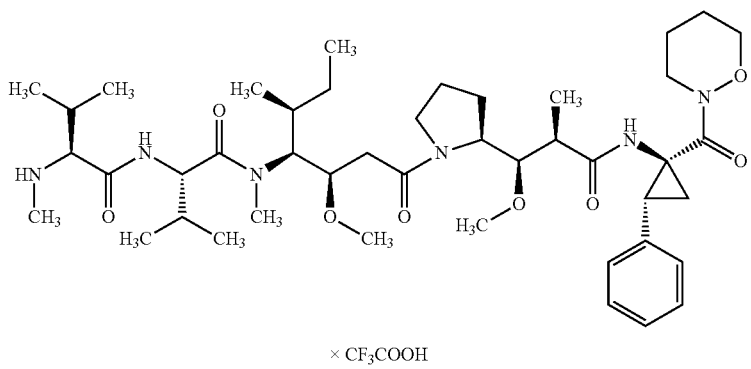 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@@H](NC)C(C)C)C(C)C]

× CF₃COOH 617 mg (1.2 mmol) of tert-butyl (2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidine-1-carboxylate (Intermediate 24) were taken up in 44 ml of dichloromethane, 4.4 ml of trifluoroacetic acid were added and the mixture was stirred at RT for 30 min. The mixture was then concentrated under reduced pressure and the residue that remained was lyophilized from dioxane/water. This gave 702 mg (quant.) of the deprotected compound (2R,3R)-3-methoxy-2-methyl-N-[1S,2R)-1-(1,2-oxazinan-2-ylcarbonyl)-2-phenylcyclopropyl]-3-[(2S)-pyrrolidin-2-yl]propanamide, trifluoroacetic acid salt as crude product which was used without further purification for the next step.

470 mg (0.74 mmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (Intermediate 4) were taken up in 57 ml of DMF, and 390 mg (about 0.74 mmol) of the (2R,3R)-3-methoxy-2-methyl-N-[(1S,2R)-1-(1,2-oxazinan-2-ylcarbonyl)-2-phenylcyclopropyl]-3-[(2S)-pyrrolidin-2-yl]propanamide, trifluoroacetic acid salt obtained above, 336 mg (0.88 mmol) of O-(7-azabenzotriazol-1-yl)-N,N,N',N'-tetramethyluronium hexafluorophosphate (HATU) and 423 µl (2.4 mmol) of N,N-diisopropylethylamine were added in succession. The mixture was stirred at RT for 2 h. The reaction was then poured into a mixture of semisaturated aqueous ammonium chloride solution and ethyl acetate. The organic phase was separated off, washed successively with saturated sodium bicarbonate solution and saturated sodium chloride solution, dried over sodium sulphate, filtered and concentrated. The residue was purified by preparative HPLC. This gave 453 mg (59% of theory) of the Fmoc-protected intermediate N-[(9H-fluoren-9-ylmethoxy)carbonyl]-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide.

HPLC (Method 5): $R_t$=2.58 min;

LC-MS (Method 1): $R_t$=3.10 min; MS (ESIpos): m/z=1035 (M+H)⁺.

453 mg (0.438 mmol) of this intermediate were dissolved in 24 ml of DMF. After addition of 2.4 ml of piperidine, the reaction was stirred at RT for 30 min. The mixture was then concentrated under reduced pressure and the residue was purified by preparative HPLC (mobile phase: acetonitrile/0.1% aq. TFA). This gave 260 mg (64% of theory) of the title compound as a colourless foam.

HPLC (Method 5): $R_t$=1.64 min;

LC-MS (Method 1): $R_t$=0.86 min; MS (ESIpos): m/z=813 (M+H)⁺

¹H-NMR (400 MHz, DMSO-$d_6$): δ=8.8 (m, 2H), 8.65 (m, 2H), 7.3-7.1 (m, 5H), 4.8-4.05 (m, 2H), 4.0 and 3.82 (2m, 2H), 3.8-3.5 (m, 8H), 3.32, 3.29, 3.20, 3.19, 3.12 and 3.00 (6s, 9H), 2.65 (t, 1H), 2.5-2.45 (m, 3H), 2.4-1.3 (m, 15H), 1.15-0.85 (m, 18H), 0.8 and 0.75 (2d, 3H) [further signals hidden under H₂O peak].

Example 18

N-Methyl-L-valyl-N-[(3R,4S,5S)-1-{(2S)-2-[(1R,2R)-3-{[(1S,2R)-1-(1,4-dihydro-3H-2,3-benzoxazin-3-ylcarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt

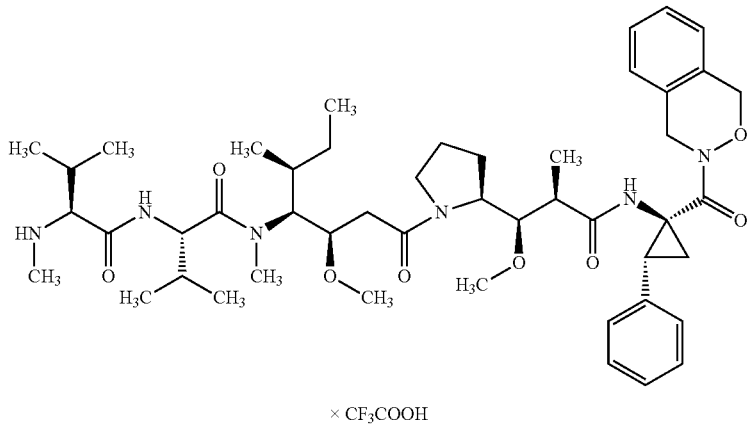 [SMILES: CC[C@H](C)[C@@H]([C@@H](CC(=O)N1CCC[C@H]1[C@H](OC)[C@@H](C)C(=O)N[C@@]1(C(=O)N2Cc3ccccc3CO2)C[C@@H]1c1ccccc1)OC)N(C)C(=O)[C@@H](NC(=O)[C@@H](NC)C(C)C)C(C)C]

× CF$_3$COOH 166 mg (0.196 mmol) of N-[(9H-fluoren-9-ylmethoxy)carbonyl]-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (Intermediate 30) were taken up in 40 ml of DMF, and 80 mg (0.196 mmol) of [(1S,2R)-1-amino-2-phenylcyclopropyl](1,4-dihydro-3H-2,3-benzoxazin-3-yl)methanone, trifluoroacetic acid salt (Intermediate 31), 112 mg (0.294 mmol) of O-(7-azabenzotriazol-1-yl)-N,N,N',N'-tetramethyluranium hexafluorophosphate (HATU) and 682 µl (3.9 mmol) of N,N-diisopropylethylamine were added in succession. The mixture was then stirred at RT overnight. The reaction was then concentrated under reduced pressure, the residue was taken up in ethyl acetate and the solution was washed with saturated aqueous sodium chloride solution. The organic phase was dried over magnesium sulphate, filtered and concentrated. The residue was finally purified by preparative HPLC. In this manner, 19 mg (9% of theory) of the Fmoc-protected intermediate N-[(9H-fluoren-9-ylmethoxy)carbonyl]-N-methyl-L-valyl-N-[(3R,4S,5S)-1-{(2S)-2-[(1R,2R)-3-{[(1S,2R)-1-(1,4-dihydro-3H-2,3-benzoxazin-3-ylcarbonyl)-2-phenylcyclopropyl]-amino}-1-methoxy-2-methyl-3-oxopropyl]pyrrolidin-1-yl}-3-methoxy-5-methyl-1-oxoheptan-4-yl]-N-methyl-L-valinamide were obtained.

HPLC (Method 5): $R_t$=1.68 min;
LC-MS (Method 1): $R_t$=1.51 min; MS (ESIpos): m/z=1083 (M+H)$^+$.

19 mg (0.015 mmol) of this intermediate were dissolved in 4 ml of DMF. After addition of 817 µl of piperidine, the reaction was stirred at RT for 5 min. The mixture was then concentrated under reduced pressure and the residue was initially digested with diethyl ether and then purified by preparative HPLC (mobile phase: acetonitrile+0.1% TFA/0.1% aq. TFA). The appropriate fractions were combined, the solvent was removed under reduced pressure and the residue was then lyophilized from dioxane/water. This gave 12 mg (92% of theory) of the title compound as a colourless foam.

HPLC (Method 6): $R_t$=2.0 min;
LC-MS (Method 1): $R_t$=0.94 min; MS (ESIpos): m/z=861 (M+H)$^+$.

Example 19

N-Methyl-L-threonyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

Example 20

N,N-Dimethyl-L-threonyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

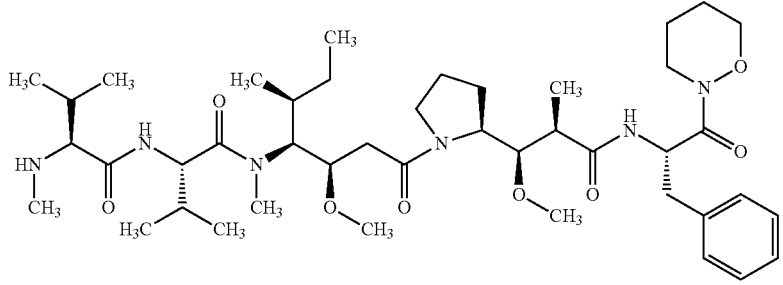 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@@H](NC)C(C)C)C(C)C]

100 mg (0.181 mmol) of N-[(benzyloxy)carbonyl]-N-methyl-L-threonyl-N-[(2R,3S,4S)-1-carboxy-2-methoxy-4-methylhexan-3-yl]-N-methyl-L-valinamide (Intermediate 32) were taken up in 5 ml of DMF, and 94 mg (0.181 mmol) of (2R,3R)-3-methoxy-2-methyl-N-[(2S)-1-(1,2-oxazinan-2-yl)-1-oxo-3-phenylpropan-2-yl]-3-[(2S)-pyrrolidin-2-yl]propanamide, trifluoroacetic acid salt (Intermediate 7), 42 mg

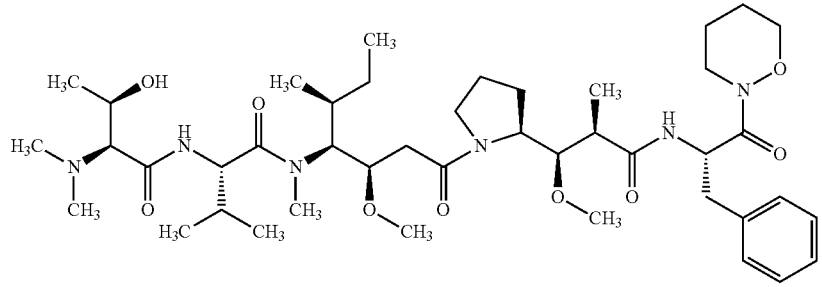 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H]([C@@H](C)O)N(C)C)C(C)C]

(0.218 mmol) of 1-(3-dimethylaminopropyl)-3-ethylcarbodiimide hydrochloride, 33 mg (0.218 mmol) of 1-hydroxy-1H-benzotriazole hydrate and 63 µl (0.36 mmol) of N,N-diisopropylethylamine were added in succession. The mixture was then stirred at RT for 2 h. The solvent was then removed under reduced pressure and the residue was purified by preparative HPLC. This gave 128 mg (75% of theory) of the Z-protected intermediate N-[(benzyloxy)carbonyl]-N-methyl-L-threonyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide.

LC-MS (Method 2): $R_t$=1.32 min; MS (ESIpos): m/z=937 (M+H)$^+$.

100 mg (0.107 mmol) of this intermediate were dissolved in 20 ml of methanol and, at RT and atmospheric pressure, hydrogenated over 10% palladium/carbon for 1 h. The catalyst was then filtered off and the solvent was evaporated. The residue that remained was lyophilized from dioxane/water (1:1). This gave 88 mg (97% of theory) of the title compound.

LC-MS (Method 1): $R_t$=0.83 min; MS (ESIpos): m/z=803 (M+H)$^+$.

84 mg (0.105 mmol) of N-methyl-L-threonyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]-pyrrolidin-1-yl}-5-methyl-1-oxoheptan-4-yl]-N-methyl-L-valinamide (Example 19) were taken up in 5 ml of dioxane/water (1:1), and 31 µl (0.418 mmol) of a 37% strength aqueous formaldehyde solution and 8 mg (0.126 mmol) of sodium cyanoborohydride were added. Using 1 ml of 0.1 N hydrochloric acid, the mixture was then adjusted to pH 6-7 and stirred at 100° C. for 1 h. The reaction was then poured into a mixture of semisaturated aqueous sodium bicarbonate solution and ethyl acetate. The organic phase was separated off, washed with saturated sodium chloride solution, dried over magnesium sulphate, filtered and concentrated. The residue was finally lyophilized from acetonitrile/water. This gave 72 mg (84% of theory) of the title compound in the form of a colourless foam.

HPLC (Method 5): $R_t$=1 6 min;
LC-MS (Method 2): $R_t$=0.96 min; MS (ESIpos): m/z=817 (M+H)$^+$.

Example 21

N-Methyl-L-valyl-N-[(3R,4S,5S)-3-methoxy-1-{(2S)-2-[(1R,2R)-1-methoxy-2-methyl-3-{[(2R)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt

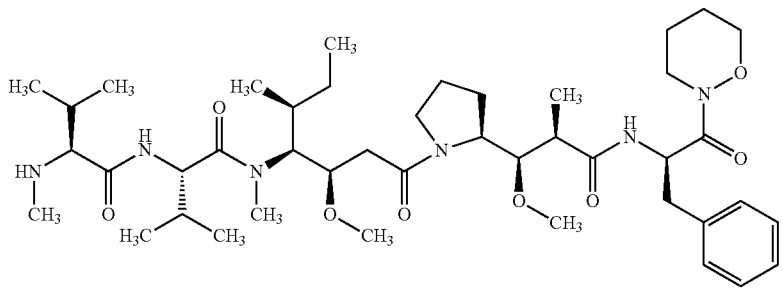

× CF₃COOH

The title compound was prepared analogously to the synthesis of Example 18 by coupling Intermediate 30 with (2R)-2-amino-1-(1,2-oxazinan-2-yl)-3-phenylpropan-1-one, trifluoroacetic acid salt (Intermediate 33) and subsequent deprotection with piperidine. The purification of the end product was carried out by preparative HPLC (mobile phase: acetonitrile+0.1% TFA/0.1% aq. TFA).

HPLC (Method 6): $R_t$=1.9 min;

LC-MS (Method 1): $R_t$=0.91 min; MS (ESIpos): m/z=801 (M+H)⁺

¹H-NMR (500 MHz, DMSO-d₆): δ=8.8 (m, 2H), 8.65 (m, 1H), 8.32 and 8.1 (2d, 1H), 7.3-7.1 (m, 5H), 5.05 and 4.95 (2m, 1H), 4.65 (m, 1H), 4.62 and 4.56 (2t, 1H), 4.1-3.75 (m, 5H), 3.7-3.45 (m, 4H), 3.28, 3.22, 3.18, 3.17, 3.04 and 2.99 (6s, 9H), 2.9 and 2.75 (2m, 2H), 2.46 (m, 3H), 2.45-2.2 (m, 3H), 2.1-1.5 (m, 12H), 1.0-0.8 (m, 18H), 0.8 and 0.75 (2d, 3H) [further signals hidden under H₂O peak].

Example 22

N-Methyl-L-valyl-N-[(3R,4S,5S)-3-methoxy-1-{(2S)-2-[(1R,2R)-1-methoxy-2-methyl-3-{[(2S)-2-methyl-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt

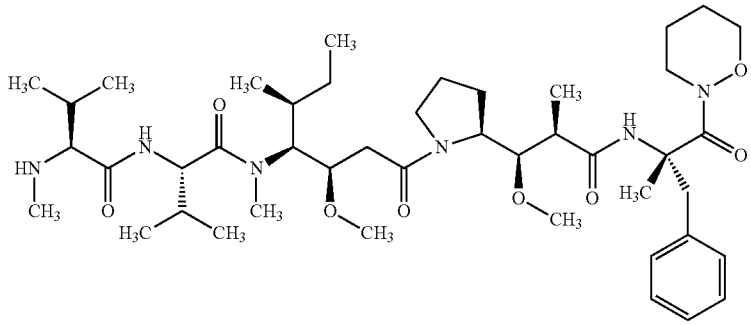

× CF₃COOH

The title compound was prepared analogously to the synthesis of Example 18 by coupling Intermediate 30 with (2S)-2-amino-2-methyl-1-(1,2-oxazinan-2-yl)-3-phenylpropan-1-one, trifluoroacetic acid salt (Intermediate 34) and subsequent deprotection with piperidine. The purification of the end product was carried out by preparative HPLC (mobile phase: acetonitrile+0.1% TFA/0.1% aq. TFA).

LC-MS (Method 1): $R_t$=0.95 min; MS (ESIpos): m/z=815 (M+H)⁺.

Example 23

N-(3-Carboxypropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]-pyrrolidin-1-yl}-5-methyl-1-oxoheptan-4-yl]-N-methyl-L-valinamide

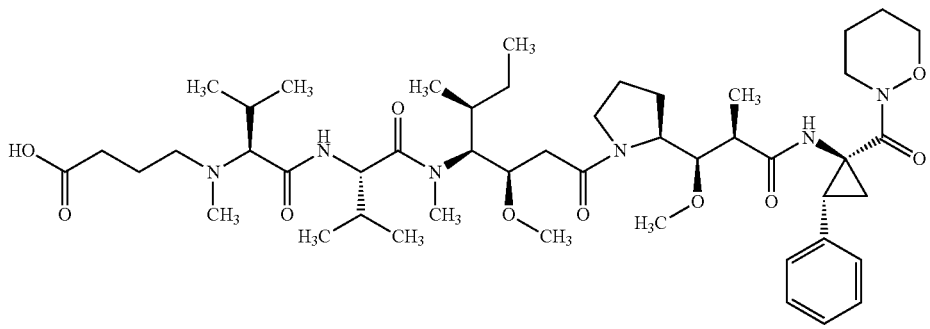 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)O)C(C)C]

50 mg (0.054 mmol) of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide, trifluoroacetic acid salt (Example 17) were dissolved in 8 ml of dioxane/water (1:1), and 70 ml (0.108 mmol) of a 15% strength solution of 4-oxobutanoic acid in water were added. The reaction was then stirred at 100° C. for 1 h. After cooling to RT, 3.7 mg (0.059 mmol) of sodium cyanoborohydride were added and the mixture was adjusted to a pH of 3 by addition of about 300 μl of 0.1 N hydrochloric acid. The reaction was then stirred at 100° C. for a further 2 h. After cooling, another 70 ml (0.108 mmol) of the 15% strength 4-oxobutanoic acid solution were added and the reaction was once more stirred at 100° C. for 1 h. A further 3.7 mg (0.059 mmol) of sodium cyanoborohydride were then added, and the pH was subsequently readjusted to 3 using about 300 μl of 0.1 N hydrochloric acid. The reaction was then stirred at 100° C. for another 2 h. If the reaction still hadn't gone to completion, this procedure was repeated a third time. Finally, the reaction was concentrated and the residue was purified by preparative HPLC. In this manner, 32 mg (65% of theory) of the title compound were obtained in the form of a colourless foam.

HPLC (Method 6): $R_t$=1.64 min;

LC-MS (Method 9): $R_t$=4.76 min; MS (ESIpos): m/z=899 (M+H)$^+$ $^1$H-NMR (500 MHz, DMSO-$d_6$): δ=8.95 and 8.8 (2m, 1H), 8.88 and 8.65 (2s, 1H), 7.4-7.1 (m, 5H), 5.0, 4.78, 4.65 and 4.55 (4m, 2H), 4.1-3.7 (m, 5H), 3.32, 3.29, 3.20, 3.12, 3.1 and 3.0 (6s, 9H), 2.75 (m, 2H), 2.63 (t, 1H), 2.4-2.2 (m, 4H), 2.1-1.2 (m, 12H), 1.2-0.8 (m, 16H), 0.75 (m, 3H) [further signals hidden under H$_2$O and DMSO peaks].

Example 24

N-(3-Carboxypropyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]-pyrrolidin-1-yl}-5-methyl-1-oxoheptan-4-yl]-N-methyl-L-valinamide

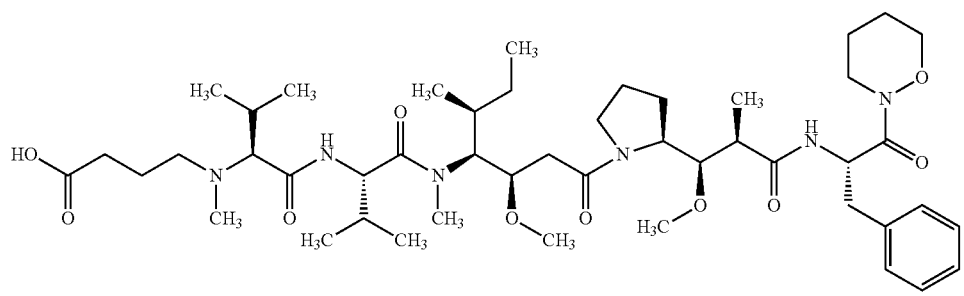 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCCC(=O)O)C(C)C]

The title compound was prepared analogously to the synthesis of Example 23 by reacting 50 mg of N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt (Example 1) with 4-oxobutanoic acid.

Yield: 34 mg (70% of theory)
HPLC (Method 5): $R_t$=1.64 min;
LC-MS (Method 9): $R_t$=4.77 min; MS (ESIpos): m/z=887 (M+H)$^+$.

Example 25

N-(4-Carboxybenzyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]-pyrrolidin-1-yl}-5-methyl-1-oxoheptan-4-yl]-N-methyl-L-valinamide

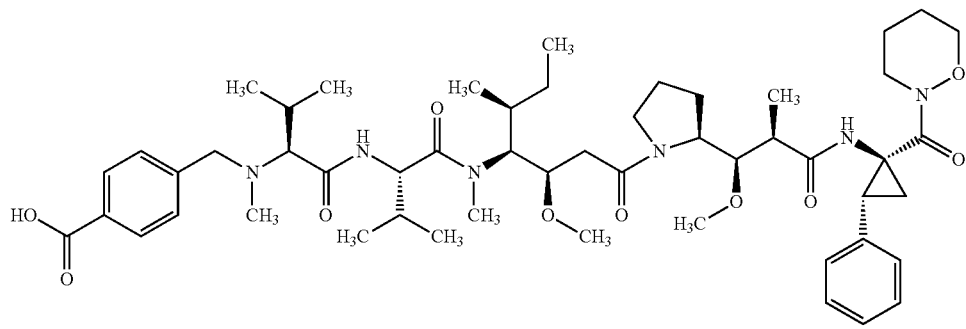 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)Cc1ccc(C(=O)O)cc1)C(C)C]

The title compound was prepared analogously to the synthesis of Example 23 by reacting 15 mg of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide, trifluoroacetic acid salt (Example 17) with 4-formylbenzoic acid.

Yield: 7.5 mg (48% of theory)
HPLC (Method 5): $R_t$=1.75 min;
LC-MS (Method 1): $R_t$=0.97 min; MS (ESIpos): m/z=947 (M+H)$^+$.

Example 26

N-(5-Carboxypentyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]-pyrrolidin-1-yl}-5-methyl-1-oxoheptan-4-yl]-N-methyl-L-valinamide

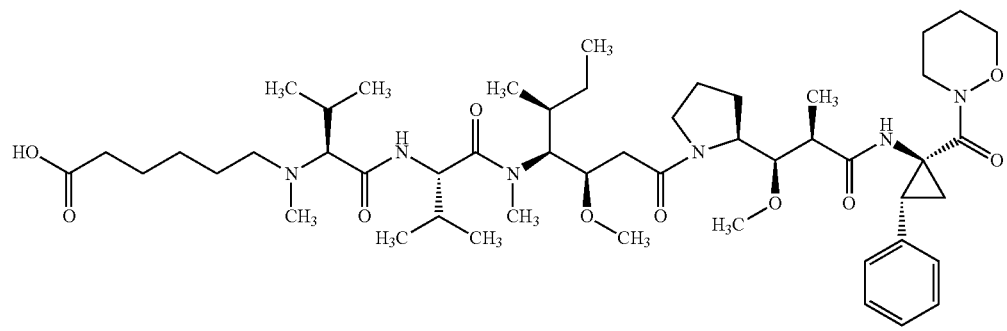 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCCCC(=O)O)C(C)C]

10 mg (0.011 mmol) of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]pyrrolidin-1-yl}-5-methyl-1-oxoheptan-4-yl]-N-methyl-L-valinamide, trifluoroacetic acid salt (Example 17) were dissolved in 2 ml of dioxane/water (1:1), and 2.8 mg (0.022 mmol) of 6-oxohexanoic acid were added. The reaction was then stirred at 100° C. for 1 h. After cooling to RT, 0.75 mg (0.012 mmol) of sodium cyanoborohydride was added and the mixture was adjusted to pH 3 by addition of 0.1 N hydrochloric acid. The reaction was then stirred at 100° C. for a further hour. After cooling, another 2.8 mg (0.022 mmol) of 6-oxohexanoic acid were added and the reaction was once more stirred at 100° C. for 1 h. A further 0.75 mg (0.012 mmol) of sodium cyanoborohydride were added, and the pH was then readjusted to 3 using 0.1 N hydrochloric acid. The reaction was then stirred at 100° C. for another 1 h. This procedure was then repeated a third time. Finally, the reaction was concentrated and the crude product was purified by preparative HPLC. This gave 6.4 mg (64% of theory) of the title compound in the form of a colourless foam.

HPLC (Method 5): $R_t$=1.68 min;

LC-MS (Method 9): $R_t$=4.86 min; MS (ESIpos): m/z=927 (M+H)$^+$.

Example 27

N-(2-Aminoethyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide, bis(trifluoroacetic acid) salt

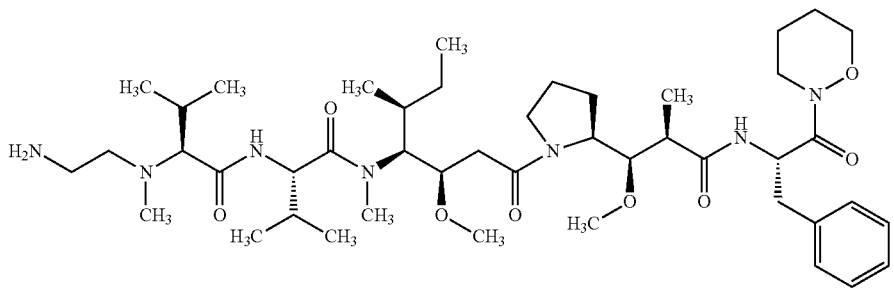

× 2 CF$_3$COOH

The title compound was prepared analogously to the synthesis of Example 2 by reacting 68 mg of N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt (Example 1) with tert-butyl (2-oxoethyl)carbamate and subsequently removing the Boc protective group with trifluoroacetic acid.

Yield: 49 mg (62% of theory over two steps)

HPLC (Method 5): $R_t$=1.58 min;

LC-MS (Method 2): $R_t$=1.05 min; MS (ESIpos): m/z=844 (M+H)$^+$

¹H-NMR (600 MHz, DMSO-d₆): δ=8.25 (m, 1H), 8.45 and 8.15 (2d, 1H), 7.65-7.55 (m, 3H), 7.23-7.1 (m, 5H), 5.12 and 4.95 (2m, 1H), 4.72 and 4.62 (2m, 1H), 4.6 and 4.52 (2t, 1H), 4.2-3.8 (m, 4H), 3.7 (d, 1H), 3.23, 3.20, 3.19, 3.18, 3.03 and 2.98 (6s, 9H), 3.0-2.7 (m, 6H), 2.4-1.2 (m, 15H), 1.05, 1.0, 0.88 and 0.82 (4d, 6H), 0.92 (m, 6H), 0.73 (m, 6H) [further signals hidden under H₂O peak].

Yield: 11 mg (41% of theory over two steps)
HPLC (Method 5): R$_t$=1.53 min;
LC-MS (Method 1): R$_t$=0.72 min; MS (ESIpos): m/z=870 (M+H)⁺.

Example 28

N-(3-Aminopropyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]-pyrrolidin-1-yl}-5-methyl-1-oxoheptan-4-yl]-N-methyl-L-valinamide

Example 29

N-(4-Methoxy-4-oxobutyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide

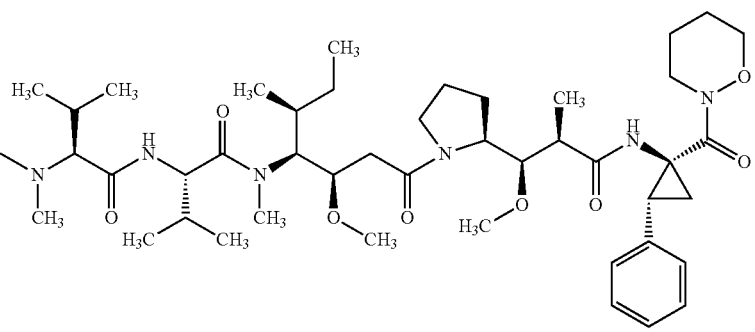

The title compound was prepared analogously to the synthesis of Example 27 by reacting 25 mg (0.027 mmol) of N-methyl-L-valyl-N-[(3R,4S,5S)-3-methoxy-1-{(2S)-2-[(1R,2R)-1-methoxy-2-methyl-3-{[(1S,2R)-1-(1,2-oxazi-

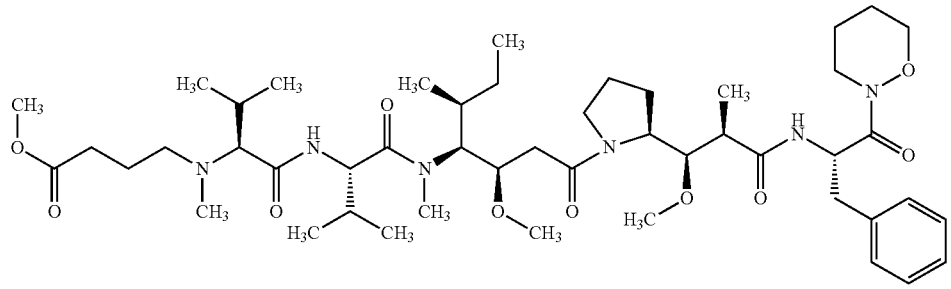 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCCC(=O)OC)C(C)C]

nan-2-ylcarbonyl)-2-phenylcyclopropyl]amino}-3-oxopropyl]-pyrrolidin-1-yl}-5-methyl-1-oxoheptan-4-yl]-N-methyl-L-valinamide, trifluoroacetic acid salt (Example 17) with benzyl (3-oxopropyl)carbamate and subsequent hydrogenolytic removal of the Z protective group (using 10% palladium on carbon as catalyst, in ethanol as solvent).

The title compound was prepared analogously to the synthesis of Example 23 by reacting 9.5 mg of N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt (Example 1) with methyl 4-oxo-butanoate.

Yield: 4 mg (43% of theory)

HPLC (Method 5): $R_t$=1.73 min;

LC-MS (Method 9): $R_t$=4.91 min; MS (ESIpos): m/z=901 (M+H)$^+$.

Example 30

N-(6-Aminohexyl)-N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-oxo-3-phenylpropan-2-yl]amino}-3-oxopropyl]pyrrolidin-1-yl}-5-methyl-1-oxoheptan-4-yl]-N-methyl-L-valinamide LC-MS (Method 1): $R_t$=0.70 min; MS (ESIpos): m/z=901 (M+H)$^+$.

Example 31

N-(6-Aminohexyl)-N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]-pyrrolidin-1-yl}-5-methyl-1-oxoheptan-4-yl]-N-methyl-L-valinamide

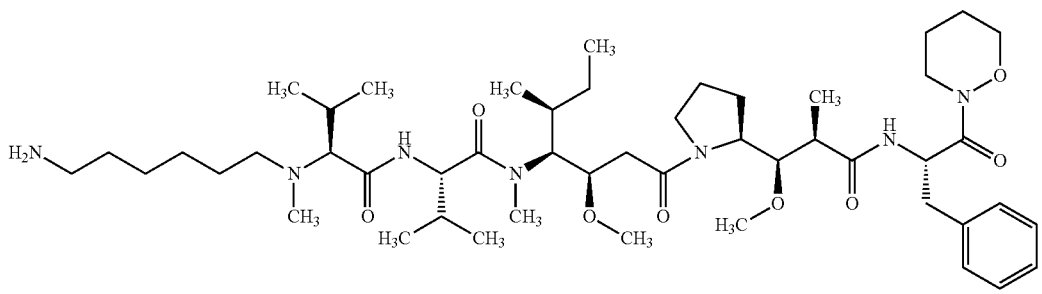 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCCCO1)OC)N(C)C(=O)[C@@H](NC(=O)[C@H](C(C)C)N(C)CCCCCCN)C(C)C]

The title compound was prepared analogously to the synthesis of Example 28 by reacting 20 mg (16 µmol) of N-methyl-L-valyl-N-[(3R,4S,5S)-3-methoxy-1-{(2S)-2-[(1R,2R)-1-methoxy-2-methyl-3-{[(2S)-1-(1,2-oxazinan-2-yl)-1-

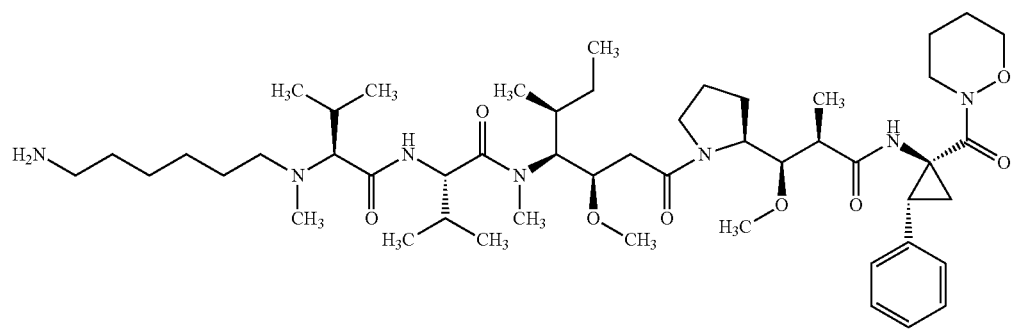 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCCCCN)C(C)C]

oxo-3-phenylpropan-2-yl]amino}-3-oxopropyl]pyrrolidin-1-yl}-5-methyl-1-oxoheptan-4-yl]-N-methyl-L-valinamide, trifluoroacetic acid salt (Example 1) with benzyl (6-oxohexyl)carbamate and subsequent hydrogenolytic removal of the Z protective group (using 10% palladium on carbon as catalyst, in methanol as solvent).

Yield: 7.6 mg (55% of theory over two steps)

HPLC (Method 6): $R_t$=1.8 min;

The title compound was prepared analogously to the synthesis of Example 28 by reacting 200 mg (0.108 mmol) of N-methyl-L-valyl-N-[(3R,4S,5S)-3-methoxy-1-{(2S)-2-[(1R,2R)-1-methoxy-2-methyl-3-{[(1S,2R)-1-(1,2-oxazinan-2-ylcarbonyl)-2-phenylcyclopropyl]amino}-3-oxopropyl]-pyrrolidin-1-yl}-5-methyl-1-oxoheptan-4-yl]-N-methyl-L-valinamide, trifluoroacetic acid salt (Example 17) with benzyl (6-oxohexyl)carbamate and subsequent hydrogenolytic removal of the Z protective group (using 5% palladium on carbon as catalyst, in methanol as solvent).

Yield: 69 mg (65% of theory over two steps)
HPLC (Method 5): $R_t$=1 7 min;
LC-MS (Method 1): $R_t$=0.76 min; MS (ESIpos): m/z=912 $(M+H)^+$.

B. Evaluation of Biological Activity

The biological activity of the compounds according to the invention can be demonstrated by in vitro and in vivo examinations known to the person skilled in the art. For example, the pharmacological and pharmacokinetic properties of the compounds according to the invention can be determined with the aid of the assays described below:

B-1. Determination of the Antiproliferative Effect on the 786-0 RCC Cell Line:

A defined cell number of the human renal cancer cell line 786-0 was sown in a 96-well microtiter plate in complete medium (2500 or 7000 cells/well) and incubated at 37° C./5% $CO_2$ overnight. After 18 h, the sowing medium was replaced by serum-free medium or medium with 2% FCS. Treatment was initiated by addition of the respective test substance in varying concentration ($10^{-5}$ M to $10^{14}$ M). The chosen incubation times were from 48 h to 96 h. Proliferation was determined with the aid of the MTT assays (ATCC, Manassas, Va., USA, catalogue No. 30-1010K). After the incubation time, the MTT reagent was incubated with the cells for 4 h, and the cells were subsequently lysed by adding the detergent overnight. The dye formed was detected at 570 nm. Proliferation of cells which had not been treated with test substance, but had otherwise been treated identically, was defined as 100%. The data obtained from this test are triple determinations, and at least two independent experiments were carried out.

Table 1 below lists the $IC_{50}$ values of representative Working Examples from this assay:

TABLE 1

| Working Example | $IC_{50}$ [nM] |
|---|---|
| 1 | 4 |
| 4 | 14 |
| 6 | 0.5 |
| 8 | 2.4 |
| 9 | 3 |
| 11 | 1.2 |
| 12 | 0.2 |
| 13 | 4 |
| 16 | 8 |
| 17 | 4 |
| 23 | 11 |
| 24 | 5 |
| 26 | 18 |

For comparison, in this test monomethylauristatin F(MMAF) has an $IC_{50}$ value of 260 nM.

B-2. Determination of the Antiproliferative Effect on the HT29 Wt Cell Line:

A defined cell number of the human colon carcinoma cell line HT29 wt (wild type) was sown in a 96-well microtiter plate in complete medium (10% FCS-RPMI) (2500 cells/well) and incubated at 37° C./5% $CO_2$ overnight. After 18 h, the sowing medium was replaced by fresh medium with 10% FCS. Treatment was initiated by addition of the respective test substance. From the substances to be investigated, dose/activity curves in a concentration range of from $10^{-5}$ M to $10^{-14}$ M (1:10-dilution series) were determined. The chosen incubation times were from 48 h to 96 h. Pro-liferation was determined with the aid of the MTT assays (ATCC, Manassas, Va., USA, catalogue No. 30-1010K). After the incubation time, the MTT reagent was incubated with the cells for 4 h, and the cells were subsequently lysed by adding the detergent overnight. The dye formed was detected at 570 nm. Proliferation of cells which had not been treated with test substance, but had otherwise been treated identically, was defined as 100%. The data obtained from this test are triple determinations, and at least two independent experiments were carried out.

Table 2 below lists the $IC_{50}$ values of representative Working Examples from this assay:

TABLE 2

| Working Example | $IC_{50}$ [nM] |
|---|---|
| 1 | 0.1 |
| 2 | 0.5 |
| 4 | 0.2 |
| 9 | 1.4 |
| 17 | 0.5 |
| 18 | 1.2 |
| 23 | 0.7 |
| 24 | 1.5 |
| 29 | 0.1 |

For comparison, in this test monomethylauristatin F (MMAF) has an $IC_{50}$ value of 10 nM.

B-3. Determination of the Effect on Tubulin Polymerization:

Cancer cells are denatured cells which frequently lead to the formation of tumours also as a result of increased cell division. Microtubuli form the spindle fibres of the spindle apparatus and are an essential constituent of the cell cycle. The regulated construction and breakdown of microtubuli allows the precise division of the chromosomes among the daughter cells, and constitutes a continuously dynamic process. Disruption to this dynamic process results in incorrect cell division and ultimately in cell death. The increased cell division of cancer cells, however, also makes them particularly sensitive towards spindle fibre poisons, which constitute a fixed constituent of chemotherapy. Spindle fibre poisons such as paclitaxel or epothilone lead to a sharply increased polymerization rate of the microtubuli, while vinca alkaloids or else monomethylauristatin E (MMAE) lead to a sharply reduced polymerization rate of the microtubuli. In both cases, the necessary dynamism of the cell cycle is critically disrupted. The compounds investigated in the context of the present invention result in a reduced polymerization rate of the microtubuli.

Tubulin polymerization was investigated using the "Fluorescence-based Microtubule Polymerisation Assay Kit" from Cytoskeleton (Denver, Colo., USA; order number: BK011). With this assay, GTP is added to unpolymerized tubulin, allowing polymerization to take place spontaneously. The assay is based on the binding of the fluorophore 4',6-diamidino-2-phenylindole (DAPI) to tubulin. Free and bound DAPI can be differentiated on the basis of different emission spectra. Since DAPI exhibits a significantly high affinity for polymerized tubulin in comparison to non-polymerized tubulin, the tubulin polymerization can be followed via the increase in the fluorescence of bound DAPI fluorophores.

For the implementation of this assay, the compounds of the invention, in solution in DMSO, were diluted from their initial concentration of 10 mM to 1 μM in water. In addition to the buffer control, paclitaxel, with a polymerization-increasing effect, and vinblastin, with a polymerization inhibiting effect, were run additionally as assay controls. Measurement was carried out using 96-well plates with a half base area. The kinetics of the tubulin polymerization were monitored in a Fluorimeter at 37° C. for 1 hour. The excitation wavelength was 355 nm, and emission was monitored at 460 nm. For the region of linear increase within the first 10 minutes, a calculation was made of the change in fluorescence per minute ($\Delta F$/min), which represents the polymerization rate of the microtubuli. The potency of the test substances was quantified on the basis of their respective reduction of the polymerization rate.

B-4. Determination of the Plasma Stability in vitro:

Method A:

1 mg of the test substance in question was dissolved in 0.5 ml of acetonitrile/DMSO (9:1). From this solution, 20 μl were removed and added to 1 ml of rat or human plasma at 37° C. (plasma of male Wistar rats with Li heparin from Harlan & Winkelmann or fresh human leukocyte-depleted plasma originating from a whole blood sample). From this plasma solution, which was shaken vigorously, 100 μl aliquots were removed immediately after addition of the sample (initial value as reference) and then after 5, 10, 30, 60, 120, 180 and 240 minutes and optionally after 24 hours and added to 300 μl of acetonitrile. The precipitated plasma proteins were removed by centrifugation at 5000 rpm for 10 minutes, and 30 μl of the supernatant were analysed by HPLC for its content of unmodified test substance. Quantification was via the area percentages of the corresponding peaks.

HPLC Method for Rat Plasma:

Instrument: Agilent 1200 with DAD, binary pump, autosampler, column oven and thermostat; column: Kromasil 100 C18, 250 mm×4 mm, 5 nm; column temperature: 45° C.; mobile phase A: 5 ml of perchloric acid/1 of water, mobile phase B: acetonitrile; gradient: 0-8 min 98% A, 2% B; 8-15 min 56% A, 44% B; 15-20 mM 10% A, 90% B; 20-21 min 10% A, 90% B; 21-23 mM 98% A, 2% B; 23-25 mM 98% A, 2% B; flow rate: 2 ml/min; UV detection: 220 nm.

HPLC Method for Human Plasma:

Instrument: Agilent 1100 with DAD, binary pump, autosampler, column oven and thermostat;

column: Kromasil 100 C18, 250 mm×4 mm, 5 μm; column temperature: 45° C.; mobile phase A: 5 ml of perchloric acid/1 of water, mobile phase B: acetonitrile; gradient: 0-3 min 98% A, 2% B; 3-10 min 65% A, 35% B; 10-15 min 40% A, 60% B; 15-21 min 10% A, 90% B; 21-22 min 10% A, 90% B; 22-24 min 98% A, 2% B; 24-26 min 98% A, 2% B; flow rate: 2 ml/min; UV detection: 220 nm.

Method B:

The test substance was incubated in rat or human plasma at 37° C. over a period of 5 h with gentle stirring. At different points in time (0, 2, 5, 10, 20, 30, 60, 120, 180 and 300 minutes), a 100 μl aliquot was removed. Following addition of internal standard (10 μl), the proteins were precipitated by addition of 200 μl of acetonitrile and the mixture was centrifuged in an Eppendorf centrifuge for 5 minutes. After addition of 150 μl of ammonium acetate buffer pH 3 to 150 μl of the supernatant, the content of unmodified test substance was analysed by LC/MSMS.

Table 3 below lists the half-lives ($t_{1/2}$) determined from these data of representative Working Examples in rat plasma:

TABLE 3

| Working Example | $t_{1/2}$ [h] | Method |
|---|---|---|
| 4 | 3 | B |
| 16 | 0.75 | A |
| 17 | >24 | A |
| 18 | >24 | A |

TABLE 3-continued

| Working Example | $t_{1/2}$ [h] | Method |
|---|---|---|
| 22 | 2 | A |
| 23 | >24 | A |

For comparison, in rat plasma the methyl ester of monomethylauristatin F (MMAF-OMe) has a $t_{1/2}$ value (according to Method A) of <1 min.

In human plasma, by way of example, no degradation was observed after 24 h for the compounds of Working Examples 1, 17 and 21 according to the invention, whereas the methyl ester of monomethylauristatin F (MMAF-OMe) was degraded by about 20% during this period.

B-5. Determination of the Cell Permeability:

The cell permeability of a substance can be investigated by means of in vitro testing in a flux assay using Caco-2 cells [M. D. Troutman and D R Thakker, Pharm. Res. 20 (8), 1210-1224 (2003)]. For this purpose, the cells were cultured for 15-16 days on 24-well filter plates. For the determination of permeation, the respective working example was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Böblingen, Germany) using reverse phase columns The HPLC system was coupled via a Turbo Ion Spray Interface to a Triple Quadropol mass spectrometer API 4000 (Applied Biosystems Applera, Darmstadt, Germany). The permeability was evaluated on the basis of a $P_{app}$ value, which was calculated using the formula published by Schwab et al. [D. Schwab et al., J. Med. Chem. 46, 1716-1725 (2003)]. A substance was classified as actively transported when the ratio $P_{app}$ (B-A) to $P_{app}$ (A-B) was >2 or <0.5.

B-6. Determination of the Substrate Properties for P-glycoprotein (P-gp):

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., J. Clin. Invest. 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as Ivermectin or Verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns The HPLC system was coupled via a Turbo Ion Spray Interface to a Triple Quadropol mass spectrometer API 3000 (Applied Biosystems Applera, Darmstadt, Germany). The permeability was evaluated on the basis of a $P_{app}$ value which was calculated using the formula published by Schwab et al. [D. Schwab et al., J. Med. Chem. 46, 1716-1725 (2003)]. A substance was classified as a P-gp sustrate when the efflux ratio $P_{app}$ (B-A) to $P_{app}$ (A-B) was >2.

As further criteria for evaluation of the P-gp substrate properties, the efflux ratios in L-MDR1 and LLC-PK1 cells or the efflux ratio in the presence or absence of an inhibitor may be compared to one another. If these values differ by a factor of more than 2, the substance in question is a P-gp substrate.

C. Working Examples for Pharmaceutical Compositions

The compounds according to the invention can be converted into pharmaceutical formulations as follows:

Tablet:
Composition:
100 mg of the compound according to the invention, 50 mg lactose (monohydrate), 50 mg maize starch (native), 10 mg polyvinylpyrrolidone (PVP 25) (BASF, Ludwigshafen, Germany) and 2 mg magnesium stearate.

Tablet weight 212 mg. Diameter 8 mm, radius of curvature 12 mm

Preparation:
The mixture of compound according to the invention, lactose and starch is granulated with a 5% strength solution (w/w) of the PVP in water. After drying, the granules are mixed with the magnesium stearate for 5 minutes. This mixture is pressed with a conventional tablet press (for tablet format see above). A pressing force of 15 kN is used as the recommended value for the pressing.

Suspension for Oral Administration:
Composition:
1000 mg of the compound according to the invention, 1000 mg ethanol (96%), 400 mg Rhodigel® (xanthan gum from FMC, Pennsylvania, USA) and 99 g water.

10 ml of oral suspension correspond to an individual dose of 100 mg of the compound according to the invention.

Preparation:
The Rhodigel is suspended in ethanol and the compound according to the invention is added to the suspension. The water is added with stirring. The mixture is stirred for approx. 6 h until swelling of the Rhodigel has ended.

Solution for Oral Administration:
Composition:
500 mg of the compound according to the invention, 2.5 g polysorbate and 97 g polyethylene glycol 400.20 g of oral solution correspond to an individual dose of 100 mg of the compound according to the invention.

Preparation:
The compound according to the invention is suspended in a mixture of polyethylene glycol and polysorbate, while stirring. The stirring operation is continued until dissolution of the compound according to the invention is complete.

i.v. Solution:
The compound according to the invention is dissolved in a concentration below the saturation solubility in a physiologically acceptable solvent (e.g. isotonic saline solution, glucose solution 5% and/or PEG 400 solution 30%). The solution is subjected to sterile filtration and is transferred into sterile and pyrogen-free injection containers.

What is claimed:

1. A compound of the formula (I)

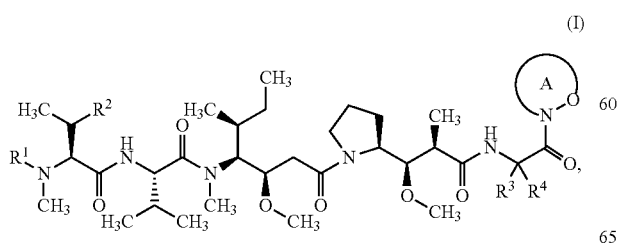

(I)

or its salt, hydrate, or hydrate of the salt, in which $R^1$ is hydrogen, $(C_1-C_6)$-alkyl or a group of the formula $Q^1-L^1-*$ or $Q^2-L^2-*$ in which

* denotes the point of attachment to the nitrogen atom, $Q^1$ is hydroxycarbonyl, $(C_1-C_4)$-alkoxycarbonyl or benzyloxycarbonyl, $L^1$ is a straight-chain $(C_1-C_{12})$-alkanediyl which is optionally substituted up to four times by methyl and in which (a) two carbon atoms are optionally bridged in 1,2-, 1,3- or 1,4-relation to one another including any carbon atoms located between them to form a $(C_3-C_6)$-cycloalkyl ring or a phenyl ring or (b) up to three $CH_2$ groups not adjacent to one another are optionally replaced by —O—, $Q^2$ is hydroxyl, amino or mono-$(C_1-C_4)$-alkylamino, and $L^2$ is a straight-chain $(C_2-C_{12})$-alkanediyl which is optionally substituted up to four times by methyl and in which (a) two carbon atoms are optionally bridged in 1,2-, 1,3- or 1,4-relation to one another including any carbon atoms located between them to form a $(C_3-C_6)$-cycloalkyl ring or a phenyl ring or (b) up to three $CH_2$ groups not adjacent to one another are optionally replaced by —O—, $R^2$ is methyl or hydroxyl, $R^3$ is hydrogen or methyl, $R^4$ is isopropyl, isobutyl, sec-butyl, tert-butyl, phenyl, benzyl, 4-hydroxybenzyl, 4-hydroxy-3-nitrobenzyl, 1-phenylethyl, diphenylmethyl, 1H-imidazol-4-ylmethyl or 1H-indol-3-ylmethyl, or $R^3$ and $R^4$ together with the carbon atom to which both are attached form a 2-phenyl-cyclopropane-1,1-diyl group of the formula

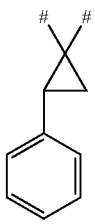

in which # denotes the points of attachment to the adjacent nitrogen atom and the carbonyl group and ring A with the N—O grouping contained therein is a mono- or bicyclic, optionally substituted heterocycle of the formula

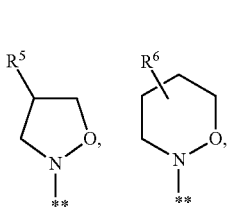 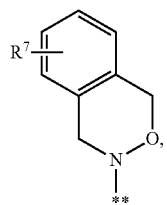

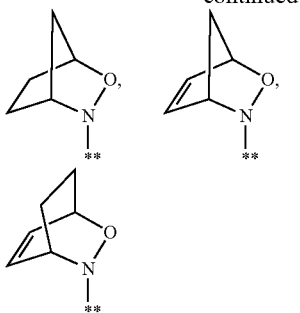

in which
** denotes the point of attachment to the carbonyl group,
R⁵ and R⁶ each is hydrogen, hydroxyl, (C₁-C₄)-alkcoxy or benzyloxy,
and
R⁷ is hydrogen, fluorine, chlorine, cyano, methyl or trifluoromethyl.

2. The compound of the formula (I) according to claim 1, or its salt, hydrate, or hydrate of the salt, in which R¹ is hydrogen, (C₁-C₄)-alkyl or a group of the formula Q¹-L¹-* or Q²-L²-* in which
* denotes the point of attachment to the nitrogen atom,
Q¹ is hydroxycarbonyl or (C₁-C₄)-alkoxycarbonyl,
L¹ is a straight-chain (C₁-C₁₂)-alkanediyl in which (a) two carbon atoms are optionally bridged in 1,3- or 1,4-relation to one another including the one or the two carbon atom(s) located between them to form a phenyl ring or (b) up to three CH₂ groups not adjacent to one another are optionally replaced by —O—,
Q² is hydroxyl, amino or methylamino
and
L² is a straight-chain (C₂-C₁₂) alkanediyl which is optionally mono- or disubstituted by methyl and in which up to three CH₂ groups not adjacent to one another are optionally replaced by —O—,
R² is methyl or hydroxyl,
R³ is hydrogen,
R⁴ is benzyl, 4-hydroxybenzyl, 1-phenylethyl or 1H-indol-3-ylmethyl,
or
R³ and R⁴ together with the carbon atom to which both are attached form a 2-phenyl-cyclopropane-1,1-diyl group of the formula

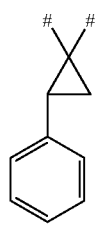

in which
# denotes the points of attachment to the adjacent nitrogen atom and the carbonyl group
and
ring A with the N—O grouping contained therein is a mono- or bicyclic, optionally substituted heterocycle of the formula

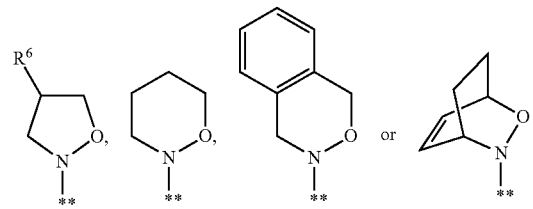

in which
** denotes the point of attachment to the carbonyl group,
and
R⁵ is hydrogen, hydroxyl or benzyloxy.

3. The compound of the formula (I) according to claim 1, or its salt, solvate, or solvate of the salt, in which R¹ is hydrogen, methyl or a group of the formula Q¹-L¹-* or Q²-L²-* in which
* denotes the point of attachment to the nitrogen atom,
Q¹ is hydroxycarbonyl, methoxycarbonyl or ethoxycarbonyl,
L¹ is a straight-chain (C₁-C₆)-alkanediyl in which two carbon atoms are optionally bridged in 1,4-relation to one another including the two carbon atoms located between than to form a phenyl ring,
Q² is hydroxyl or amino,
and
L² is a straight-chain (C₂-C₆)-alkanediyl,
R² is methyl,
R³ is hydrogen,
R⁴ is benzyl, 1-phenylethyl or 1H-indol 3-ylmethyl,
or
R³ and R⁴ together with the carbon atom to which both are attached form a (1S,2R)-2-phenylcyclopropane-1,1-diyl group of the formula

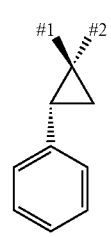

in which
1 denotes the point of attachment to the adjacent nitrogen atom
and
2 denotes the point of attachment to the carbonyl group
and
ring A with the N—O grouping contained therein is a mono- or bicyclic, optionally substituted heterocycle of the formula

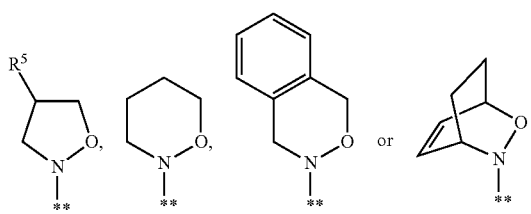

in which
** denotes the point of attachment to the carbonyl group, and
$R^5$ is hydrogen, hydroxyl or benzyloxy.

4. The compound of claim 1 having the formula (I-A)

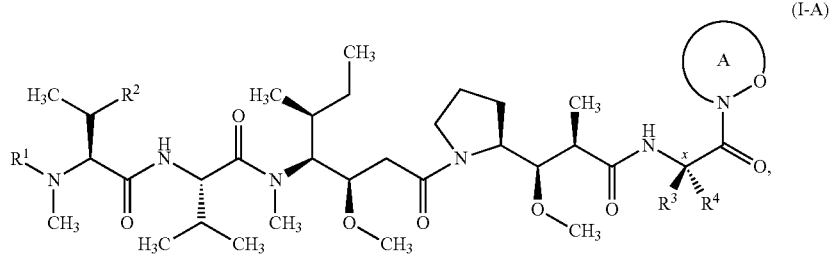

(I-A)

or its salt, solvate, or solvate of the salt, in which $R^1$, $R^2$, $R^3$, $R^4$ and ring A have the meanings defined in claim 1 and the $C^x$ carbon atom carrying the radicals $R^3$ and $R^4$ has the S configuration as shown.

5. A process for preparing a compound of the formula (I)

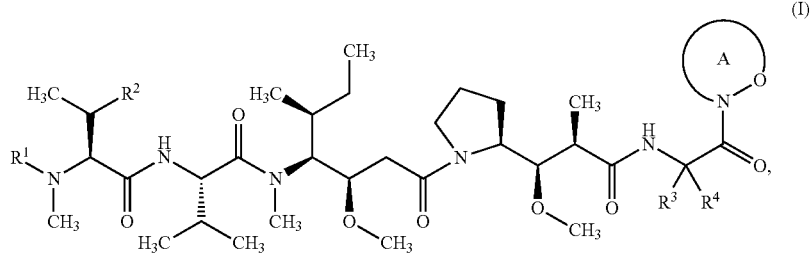

(I)

or its salt, hydrate, or hydrate of the salt,
in which
is hydrogen, $(C_1-C_6)$-alkyl or a group of the formula $Q^1-L^1-*$ or $Q^2-L^2-*$ in which
* denotes the point of attachment to the nitrogen atom,
$Q^1$ is hydroxycarbonyl, $(C_1-C_4)$-alkoxycarbonyl or benzyloxycarbonyl,
$L^1$ is a straight-chain $(C_1-C_{12})$-alkanediyl which is optionally substituted up to four times by methyl and in which (a) two carbon atoms are optionally bridged in 1,2-, 1,3- or 1,4-relation to one another including any carbon atoms located between them to form a $(C_3-C_6)$-cycloalk ring or a phenyl ring or (b) up to three $CH_2$ groups not adjacent to one another are optionally replaced by —O—, $Q^2$ is hydroxyl, amino or mono-$(C_1-C_4)$-alkylamino, and
$L^2$ is a straight-chain $(C_2-C_{12})$-alkanediyl which is optionally substituted up to four times by methyl and in which (a) two carbon atoms are optionally bridged in 1,2-, 1,3- or 1,4-relation to one another including any carbon atoms located between them to form a $(C_3-C_6)$-cycloalkyl ring or a phenyl ring or (b)to three $CH_2$ groups not adjacent to one another are optionally replaced by —O—, $R^2$ is methyl or hydroxyl,
$R^3$ is hydrogen or methyl,
$R^4$ is isopropyl, isobutyl, sec-butyl, tert-butyl, phenyl, benzyl, 4-hydroxybenzyl, 4-hydroxy-3-nitrobenzyl, 1-phenylethyl, diphenylmethyl, 1H-imidazol-4-ylmethyl or 1H-indol-3-ylmethyl, or $R^3$ and $R^4$ together with the carbon atom to which both are attached form a 2-phenyl-cyclopropane-1,1-diyl group of the formula

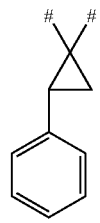

in which
# denotes the points of attachment to the adjacent nitrogen atom and the carbonyl group and ring A with the N—O grouping contained therein is a mono- or bicyclic, optionally substituted heterocycle of the formula

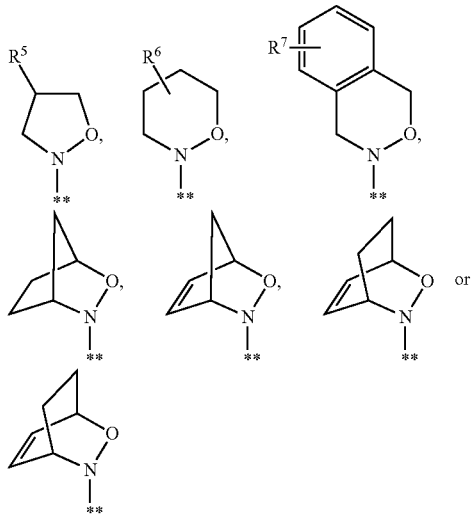

in which

** denotes the point of attachment to the carbonyl group, $R^5$ and $R^6$ each is hydrogen, hydroxyl, $(C_1\text{-}C_4)$-alkoxy or benzyloxy, and $R^7$ is hydrogen, fluorine, chlorine, cyano, methyl or trifluoromethyl in which a compound of the formula (II)

(II)

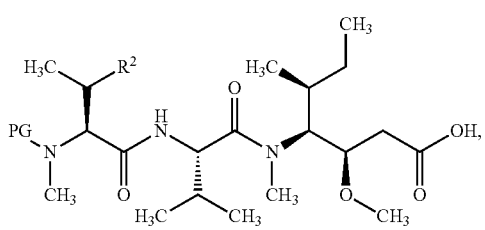

in which $R^2$ has the meaning given in the formula (I)

and

PG is an amino protective group, is coupled in an inert solvent with activation of the carboxyl group in (II) either

[A] first with the compound of the formula (III)

(III)

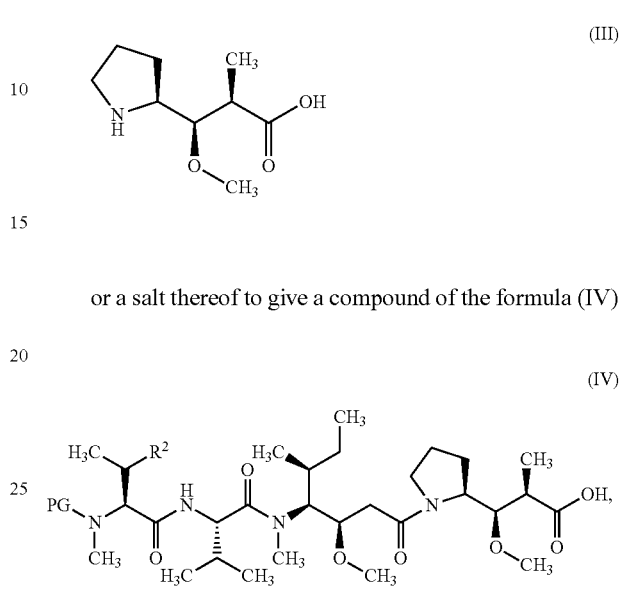

or a salt thereof to give a compound of the formula (IV)

(IV)

in which $R^2$ has the meaning given in the formula (I) and PG has the meaning given in the formula (II), and this compound is then coupled in an inert solvent with activation of the carboxyl function with a compound of the formula (V)

(V)

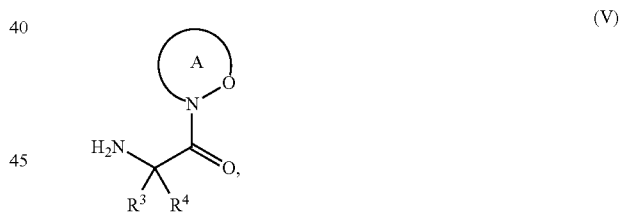

in which $R^3$, $R^4$ and ring A each has the meaning given in the formula (I), or a salt of this compound, to give a compound of the formula (VI)

(VI)

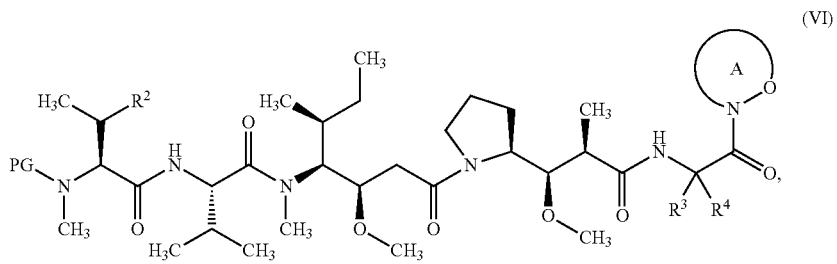

in which $R^2$, $R^3$, $R^4$, ring A each has the meaning given in the formula (I) and PG has the meaning given in the formula (II), or

[B] with a compound of the formula (VII)

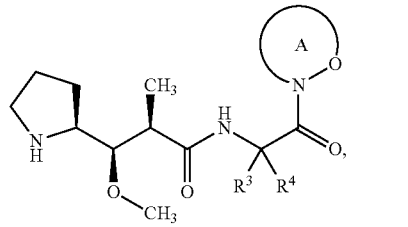
(VII)

in which $R^3$, $R^4$ and ring A each has the meaning given in the formula (I), or a salt of this compound, to give the compound of the formula (VI)

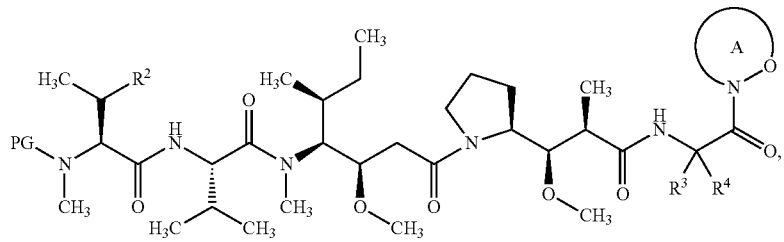
(VI)

in which $R^2$, $R^3$, $R^4$, and ring A each has the meaning given in the formula (I) and PG has the meaning given in the formula (II), and the respective resulting compound of the formula (VI) is deprotected to give a compound of the formula (I-B)

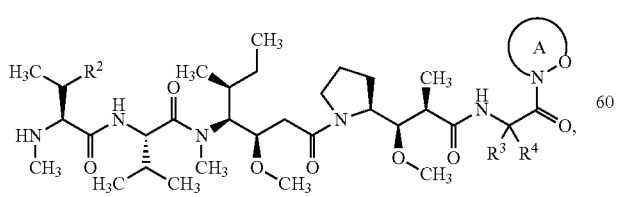
(I-B)

in which $R^2$, $R^3$, $R^4$ and ring A each has the meaning given in the formula (I), and this is optionally converted either (i) by base-induced alkylation with a compound of the formula (VIII)

 (VIII)

in which
$R^{1A}$ has the meaning of $R^1$-given in the formula (I), but is not hydrogen,
and
X is a leaving group
into a compound of the formula (I-C)

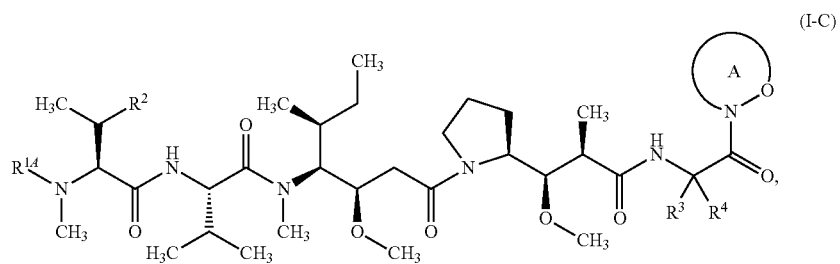 (I-C)

in which $R^{1A}$ has the meaning given in the formula (VIII), and $R^2$, $R^3$, $R^4$ and ring A each has the meaning given in the formula (I) or (ii) by reaction with a compound of the formula (IX)

 (IX)

in which
$R^{1B}$ has the meaning of $R^{1A}$ given in the formula (VIII), but with the alkyl chain length reduced by one $CH_2$ unit,
in the presence of a reducing agent into a compound of the formula (I-D)

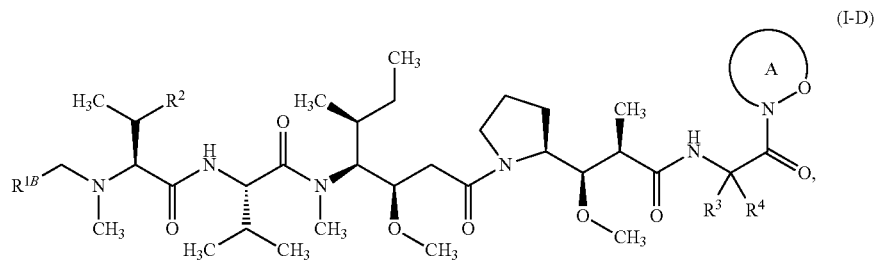 (I-D)

in which $R^{1B}$ has the meaning of $R^{1A}$ given in the formula (VIII), but with the alkyl chain length reduced by one $CH_2$ unit, and $R^2, R^3, R^4$ and ring A each has the meaning given in the formula (I), and the compounds of the formulae (I-B), (I-C) and (I-D) are optionally separated into their enantiomers and/or diastereomers and/or converted with the appropriate (i) solvents and/or (ii) bases or acids hydrates, salts and/or hydrates of the salts.

6. A medicament comprising a compound of the formula (I)

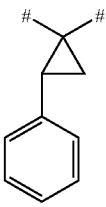

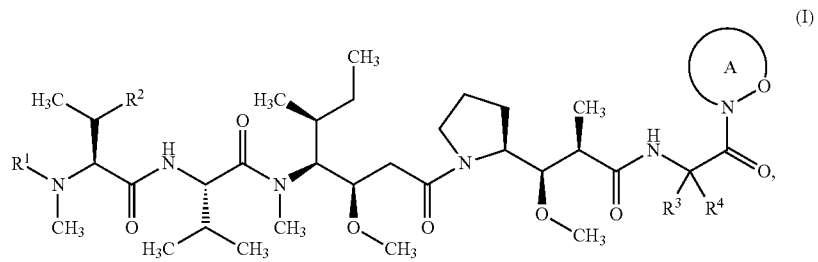

or its salt, hydrate, or hydrate of the salt, in which $R^1$ is hydrogen, $(C_1-C_6)$-alkyl or a group of the formula $Q^1-L^1-*$ or $Q^2-L^2-*$ in which

* denotes the point of attachment to the nitrogen atom, $Q^1$ is hydroxycarbonyl, $(C_1-C_4)$-alkoxycarbonyl or benzyloxycarbonyl, $L^1$ is a straight-chain $(C_1-C_{12})$alkanediyl which is optionally substituted up to four times by methyl and in which (a) two carbon atoms are optionally bridged in 1,2-, 1,3- or 1,4-relation to one another including any carbon atoms located between them to form a $(C_3-C_6)$-cycloalkyl ring or a phenyl ring or (b) up to three $CH_2$ groups not adjacent to one another are optionally replaced by —O—, $Q^2$ is hydroxyl, amino or mono-$(C_1-C_4)$-alkylamino, and $L^2$ is a straight-chain $(C_2-C_{12})$-alkanediyl which is optionally substituted up to four times by methyl and in which (a) two carbon atoms are optionally bridged in 1,2-, 1,3- or 1,4-relation to one another including any carbon atoms located between them to form a $(C_3-C_6)$-cloalkalkyl ring or a phenyl ring or (b) up to three $CH^2$ groups not adjacent to one another are optionally replaced by —O—, $R^2$ is methyl or hydroxyl, $R^3$ is hydrogen or methyl, $R^4$ is isopropyl, isobutyl, sec-butyl, tert-butyl, phenyl, benzyl, 4-hydroxybenzyl, 4-hydroxy-3-nitrobenzyl, 1-phenylethyl, diphenylmethyl, 1H-imidazol-4-ylmethyl or 1H-indol-3-ylmethyl, or $R^3$ and $R^4$ together with the carbon atom to which both are attached form a 2-phenyl-cyclopropane-1,1-diyl group of the formula in which # denotes the points of attachment to the adjacent nitrogen atom and the carbonyl group, and ring A with the N—O grouping contained therein is a mono- or bicyclic, optionally substituted heterocycle of the formula

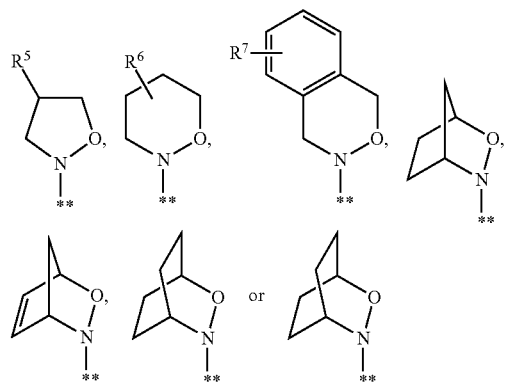

in which

** denotes the point of attachment to the carbonyl group, $R^5$ and $R^6$ each is hydrogen, hydroxyl, $(C_1-C_4)$-alkoxy or benzyloxy and $R^7$ is hydrogen, fluorine, chlorine, cyano, methyl or trifluoromethyl. and pharmaceutically suitable auxiliaries.

7. The medicament of Claim 6 in combination with one or more further active compounds.

8. A method for the treatment of cancerous and tumour disorders in humans and animals comprising the administration of an effective amount of a compound of the formula (I):

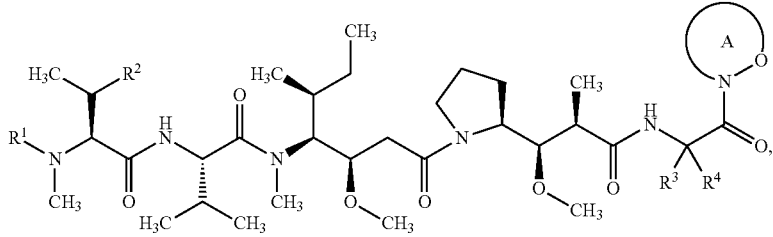

or its salt, hydrate, or hydrate of the salt,
in which
$R^1$ is hydrogen, $(C_1-C_6)$-alkyl or a group of the formula $Q^1-L^1-*$ or $Q^2-L^2-*$ in which
* denotes the point of attachment to the nitrogen atom,
$Q^1$ is hydroxycarbonyl, $(C_1-C_4)$-alkoxycarbonyl or benzyloxycarbonyl,
$L^1$ is a straight-chain $(C_1C_{12})$-alkanediyl which is optionally substituted up to four times by methyl and in which (a) two carbon atoms are optionally bridged in 1,2-, 1,3- or 1,4-relation to one another including any carbon atoms located between them to form a $(C_3-C_6)$-cycloalkyl ring or a phenyl ring or (b) up to three CH$_2$ groups not adjacent to one another are optionally replaced by —O—,
$Q^2$ is hydroxyl, amino or mono-$(C_1-C_4)$-alkylamino,
and
$L^2$ is a straight-chain $(C_2-C_{12})$ -alkanediyl which is optionally substituted up to four times by methyl and in which (a) two carbon atoms are optionally bridged in 1,2-, 1,3- or 1,4-relation to one another including any carbon atoms located between them to form a $(C_3-C_6)$-cycloalkyl ring or a phenyl ring or (b) up to three CH$_2$ groups not adjacent to one another are optionally replaced by —O—,
$R^2$ is methyl or hydroxyl,
$R^3$ is hydrogen or methyl,
$R^4$ is isopropyl, isobutyl, sec-butyl, tert-butyl, phenyl, benzyl, 4-hydroxybenzyl, 4-hydroxy- 3-nitrobenzy, 1-phenylethyl, diphenylmethyl, 1H-imidazol-4-ylmethyl or 1H-indol-3-ylmethyl,
or
$R^3$ and $R^4$ together with the carbon atom to which both are attached form a 2-phenyl-cyclopropane-1,1-diyl group of the formula

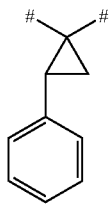

in which
# denotes the points of attachment to the adjacent nitrogen atom and the carbonyl group
and
ring A with the N—O grouping contained therein is a mono- or bicyclic, optionally substituted heterocycle of the formula

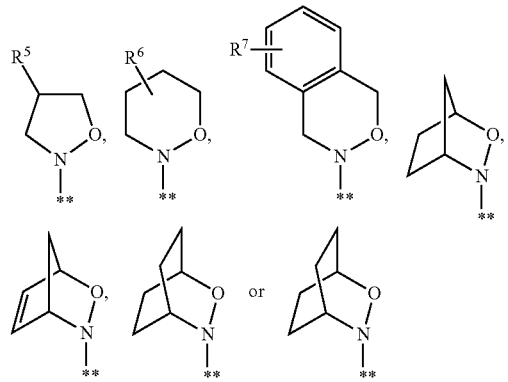

in which
** denotes the point of attachment to the carbonyl group,
$R^5$ and $R^6$ each is hydrogen, hydroxyl, $(C_1-C_4)$-alkoxy or benzyloxy,
and
$R^7$ is hydrogen, fluorine, chlorine, cyano, methyl or trifluoromethyl.

9. The compound of claim 1, wherein said compound is selected from the group consisting of:

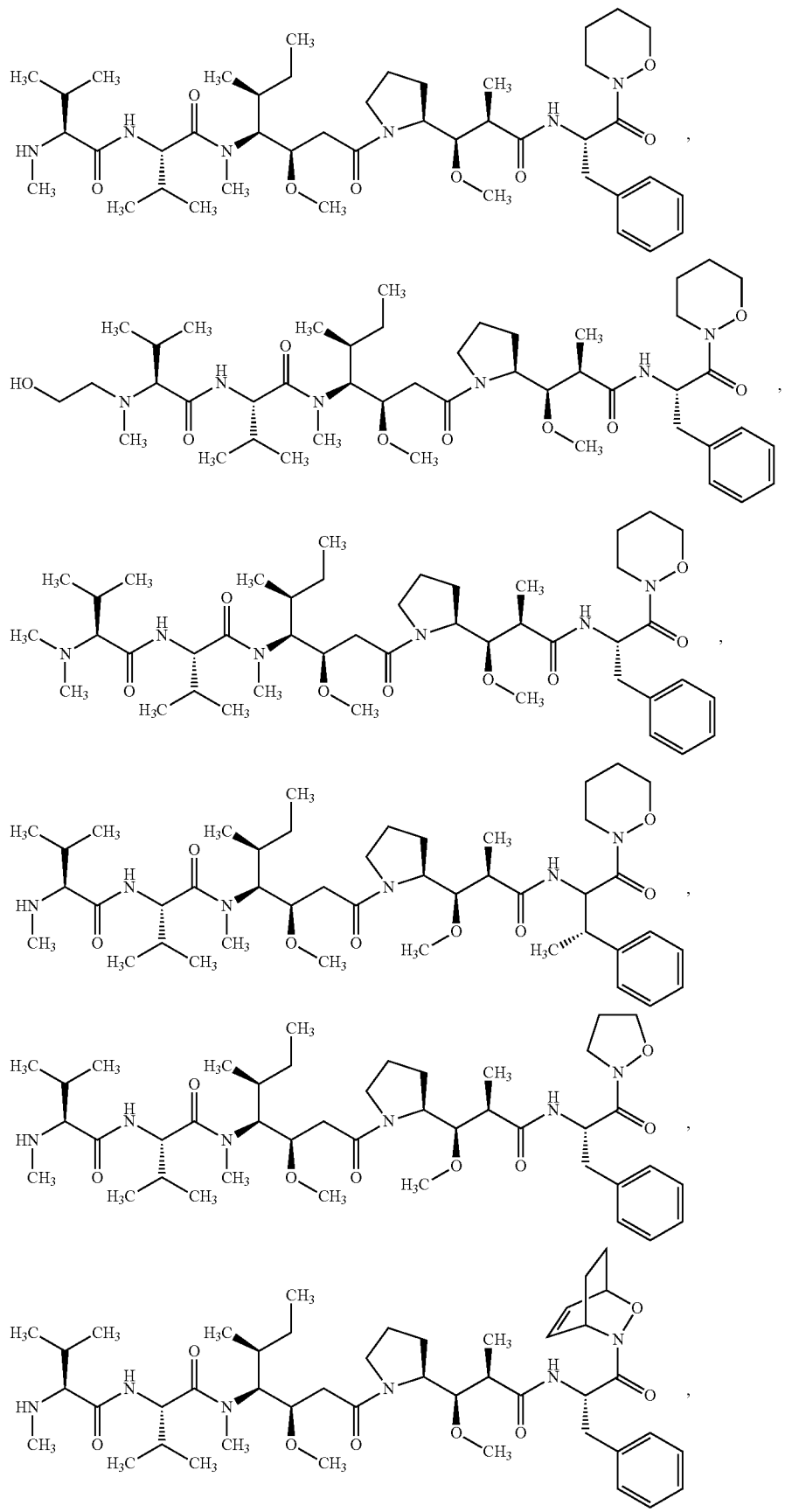

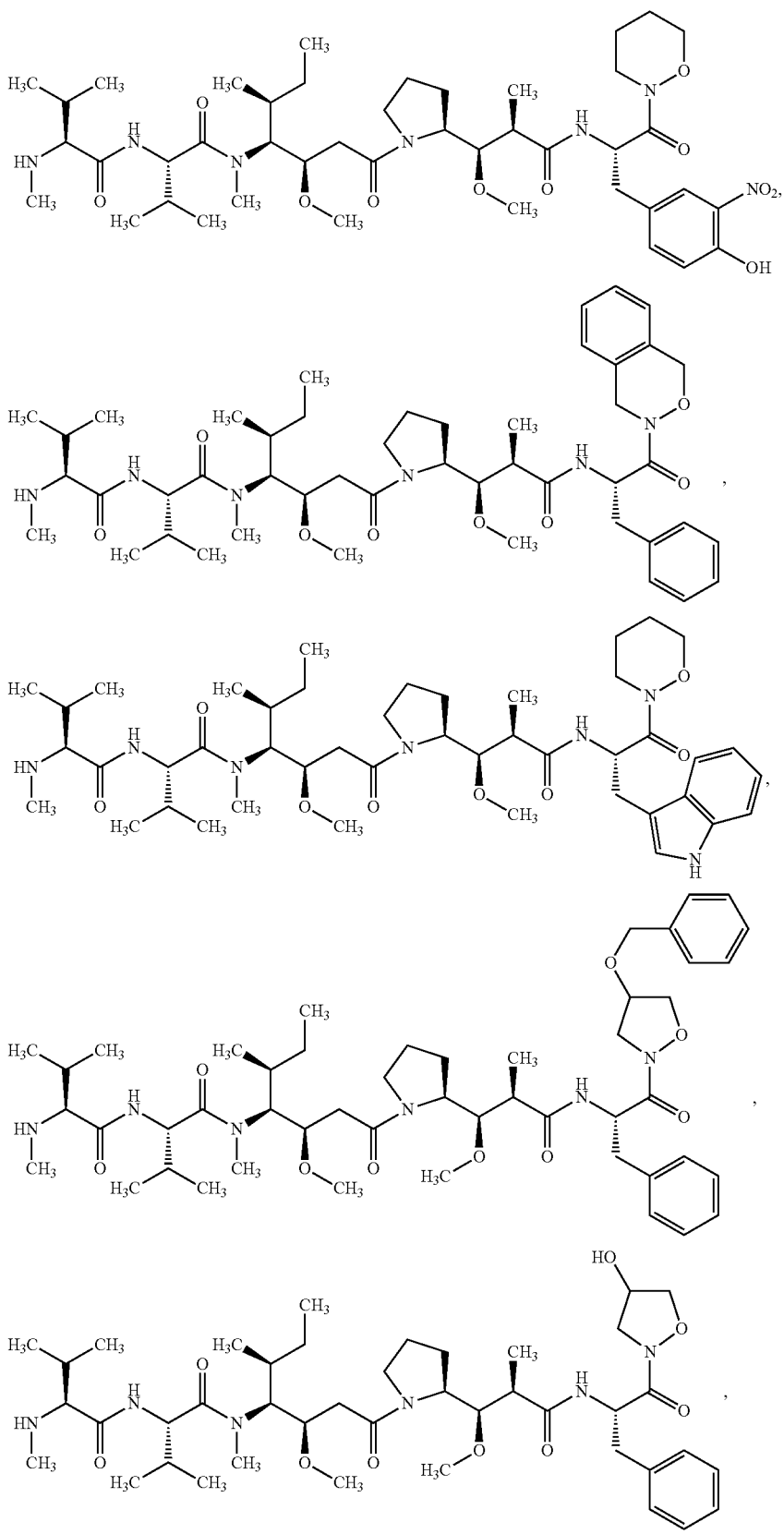

-continued
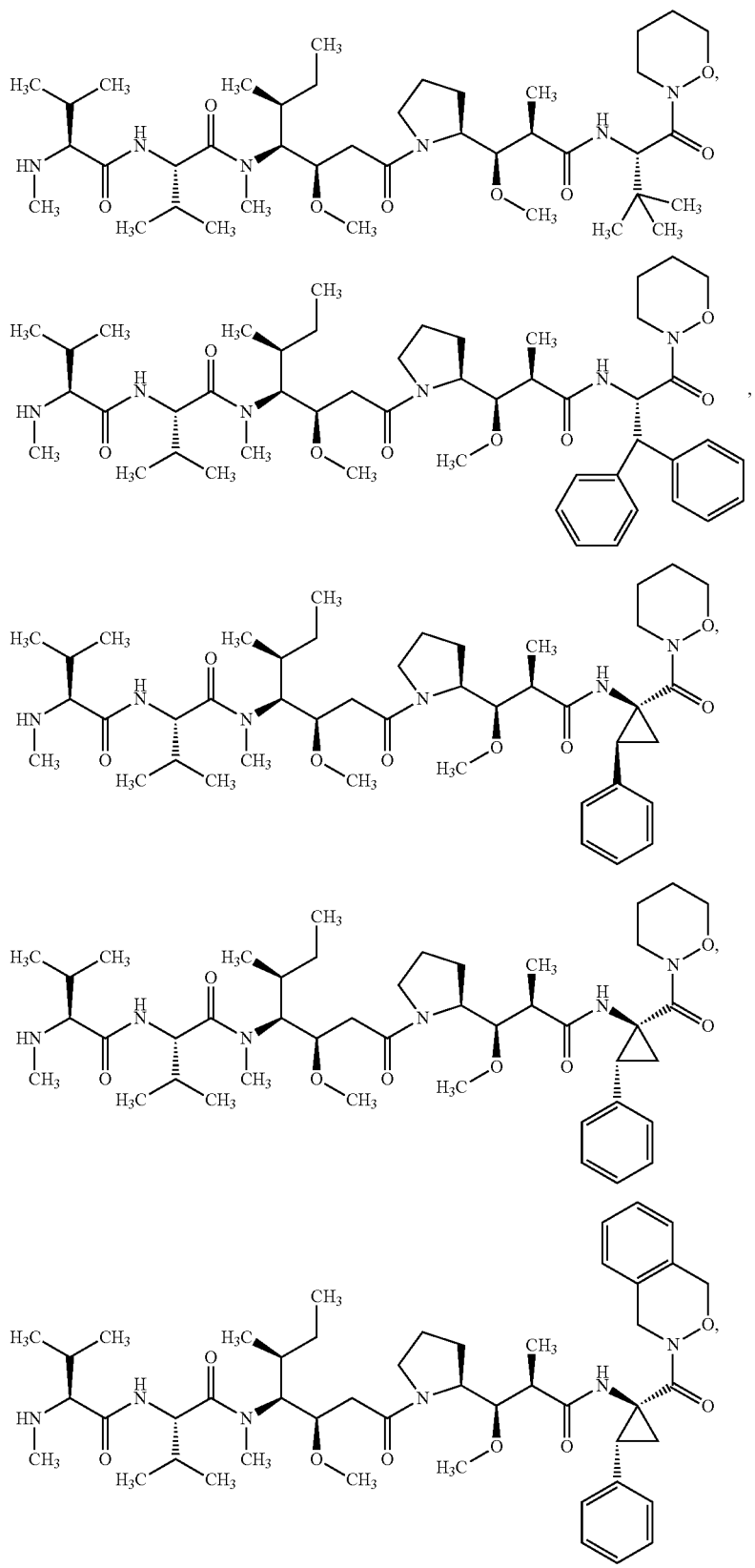

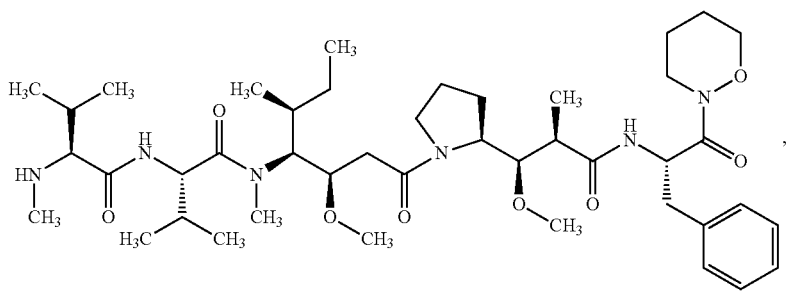,
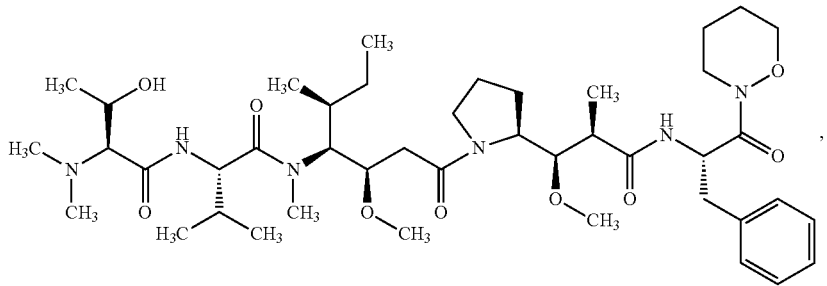,
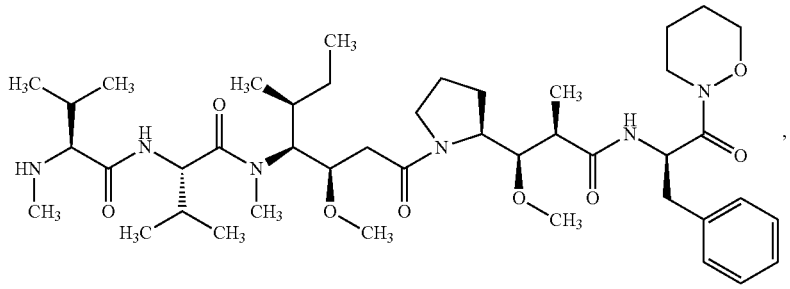,
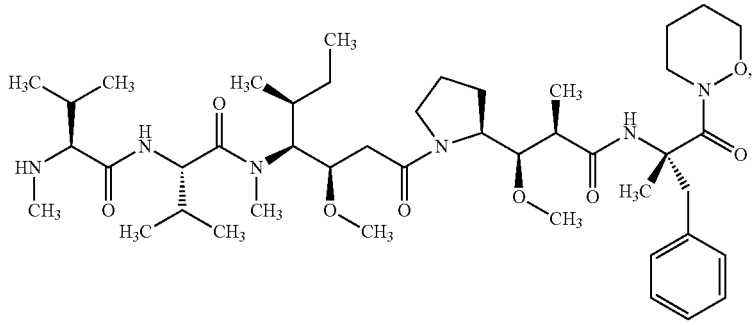,
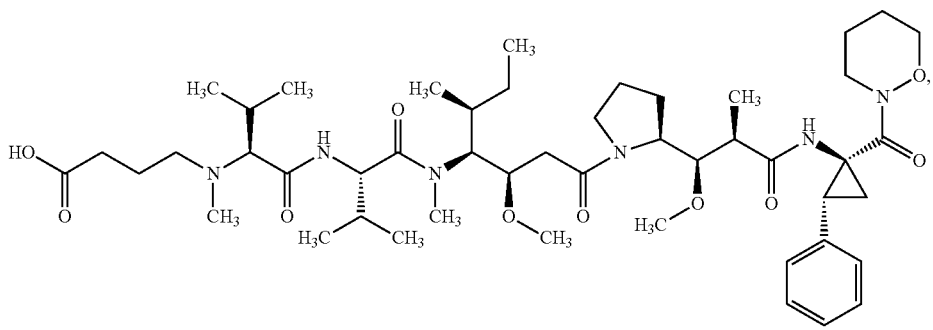,

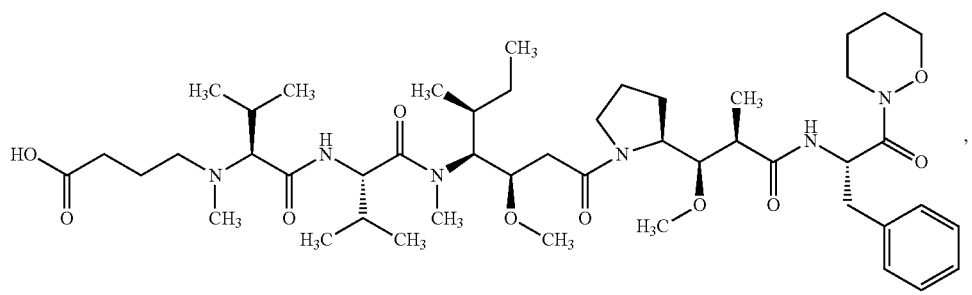
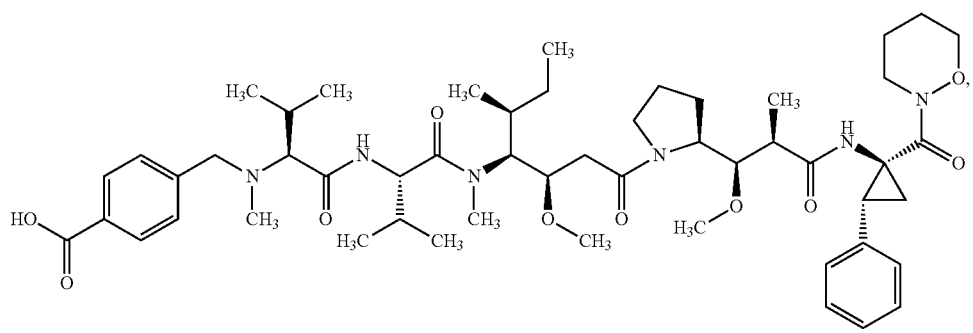
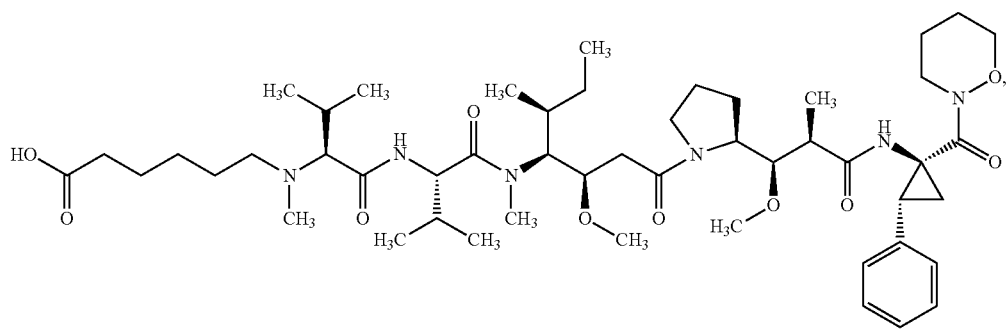
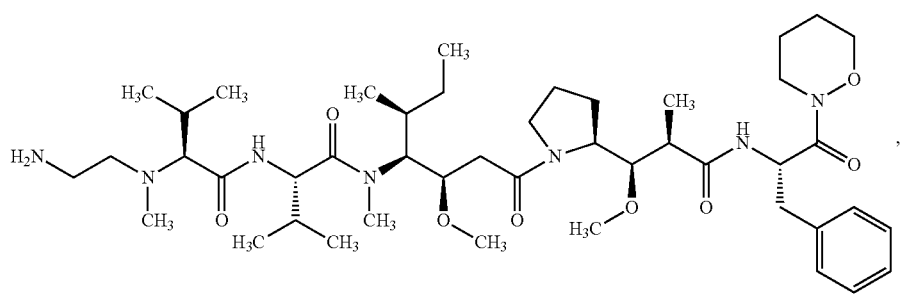
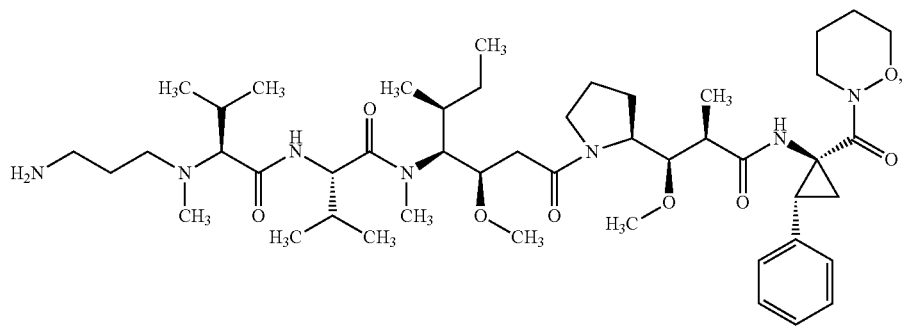

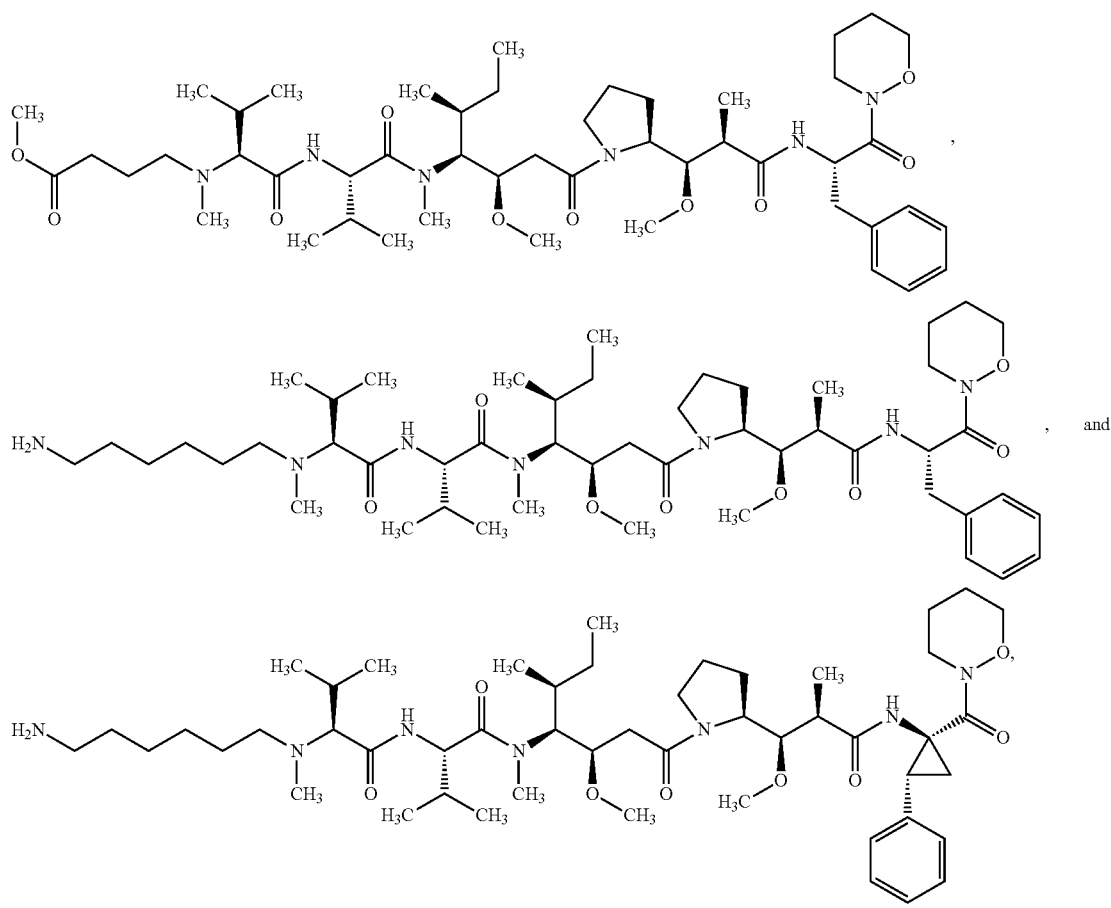
or its salt, solvate, or solvate of the salt.
10. The compound of claim 9, wherein said compound is selected from the group consisting of:
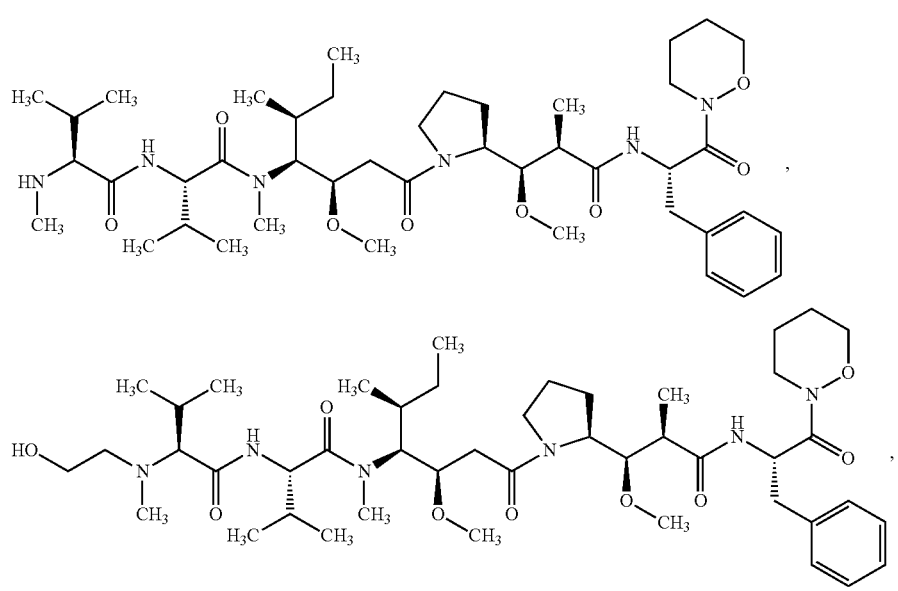

-continued
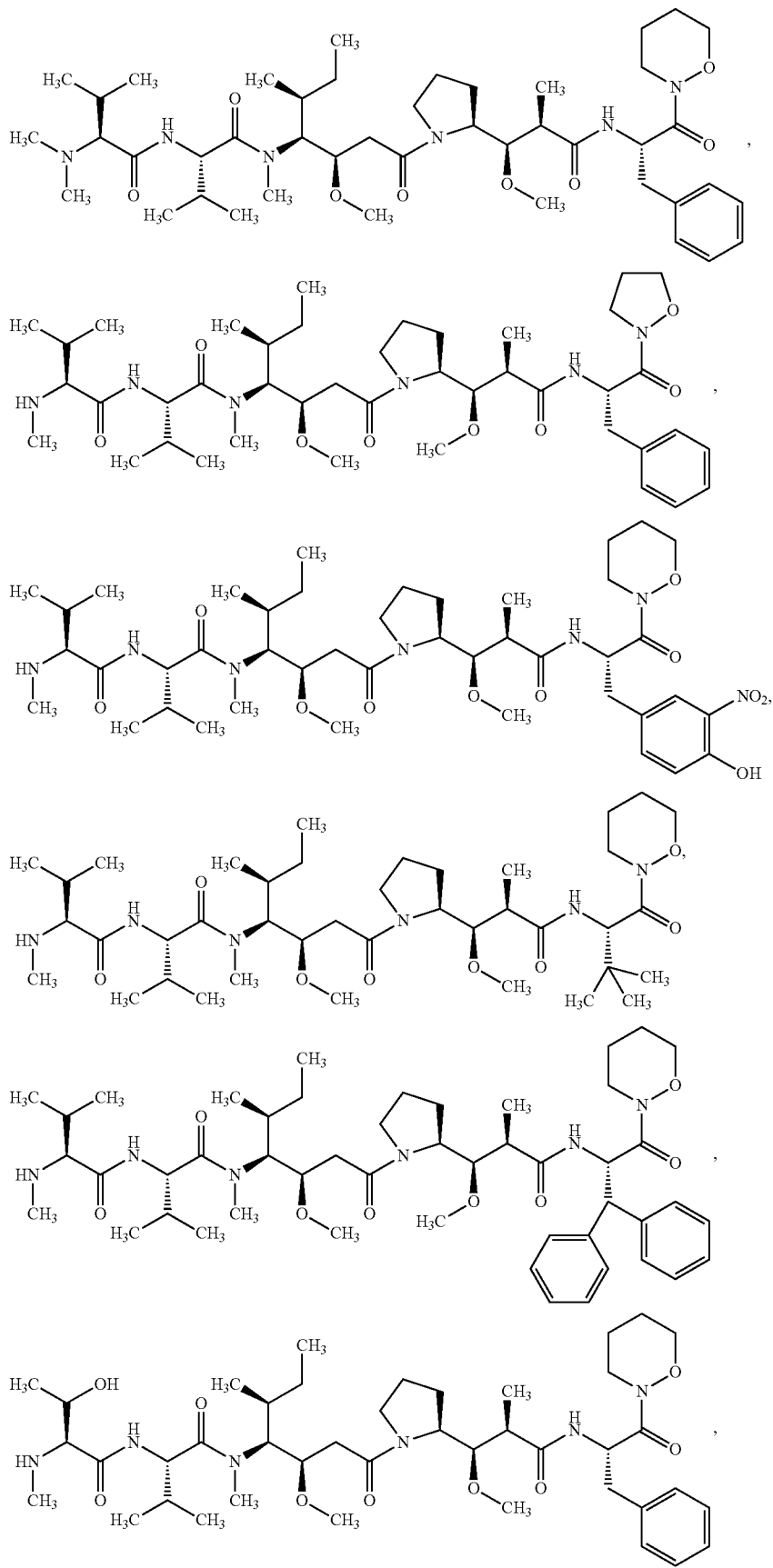

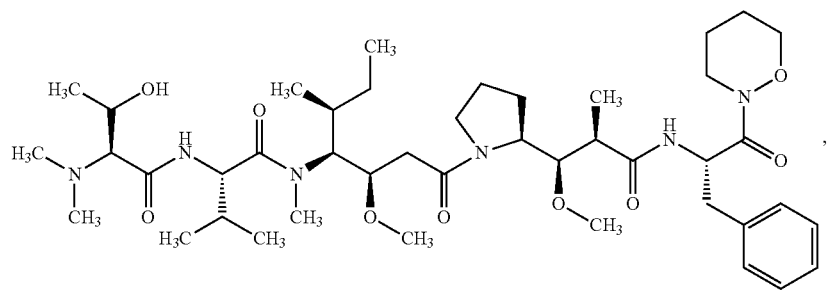
,
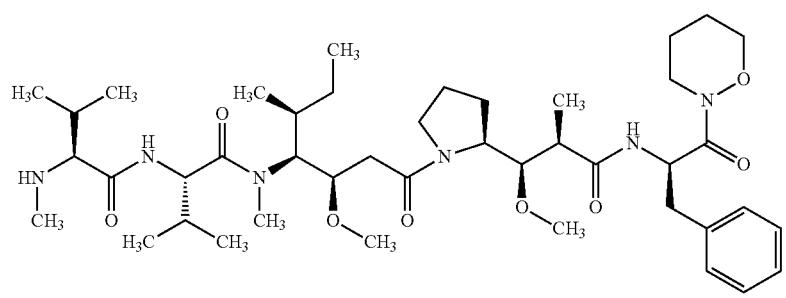
,
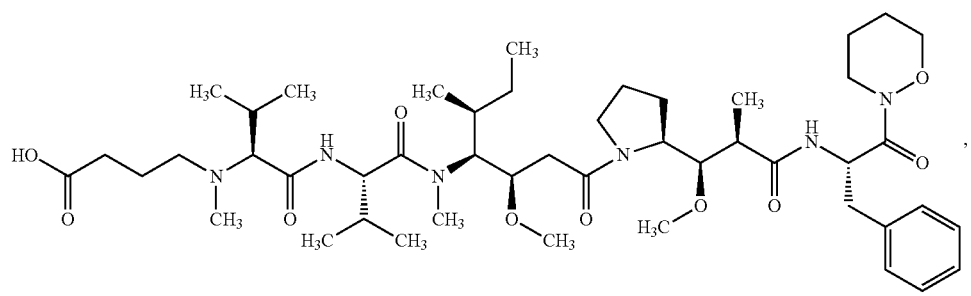
,
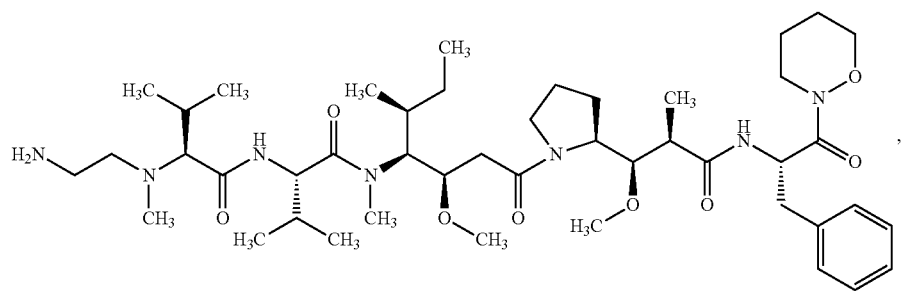
,
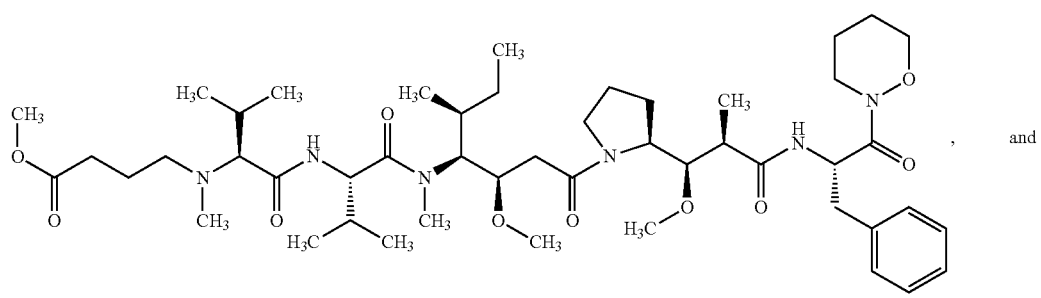
and

-continued
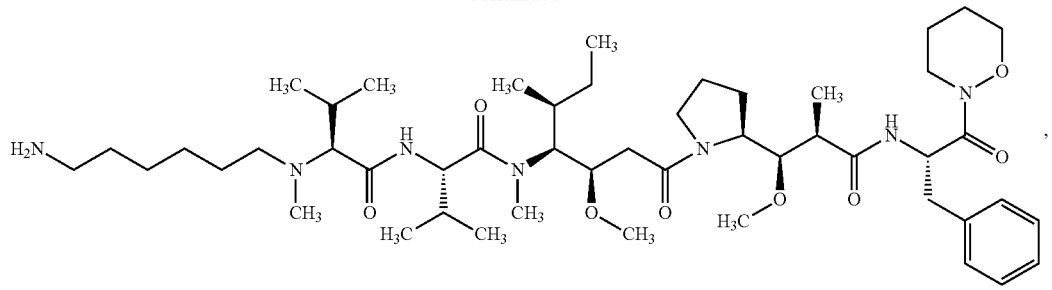
or its salt, solvate, or solvate of the salt.
11. The compound of claim 9, wherein said compound is:
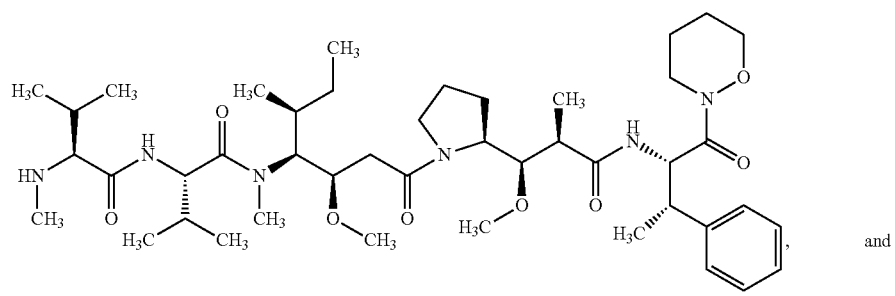
, and
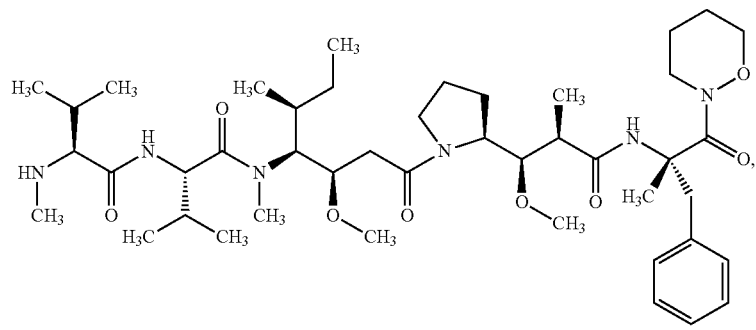
or its salt, solvate, or solvate of the salt.
12. The compound of claim 9, wherein said compound is selected from the group consisting of:
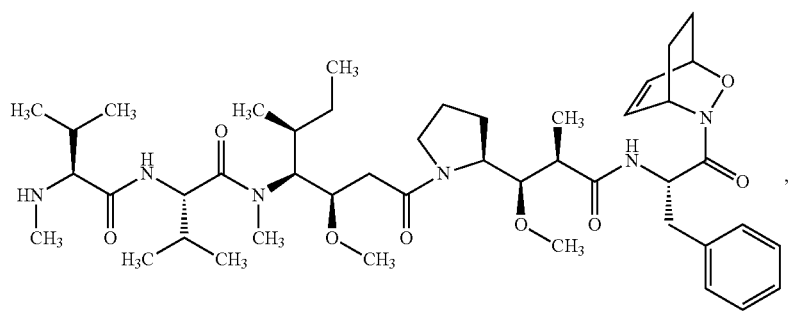
,

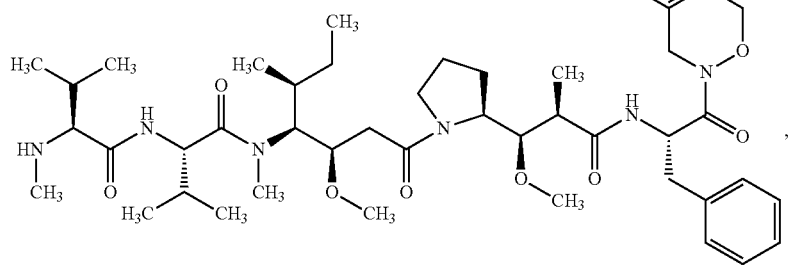
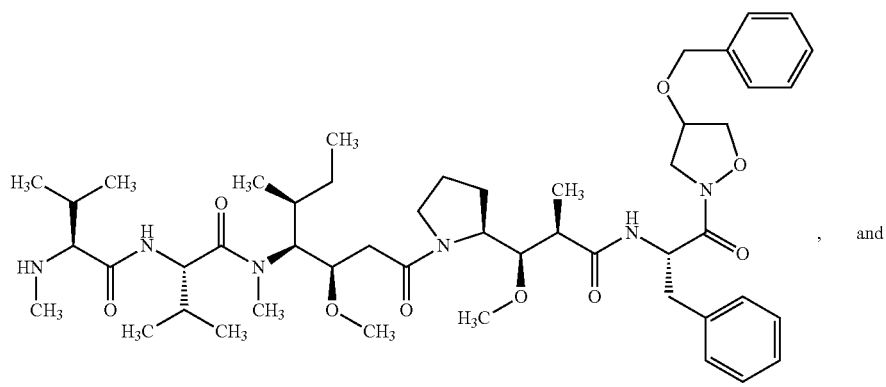
, and
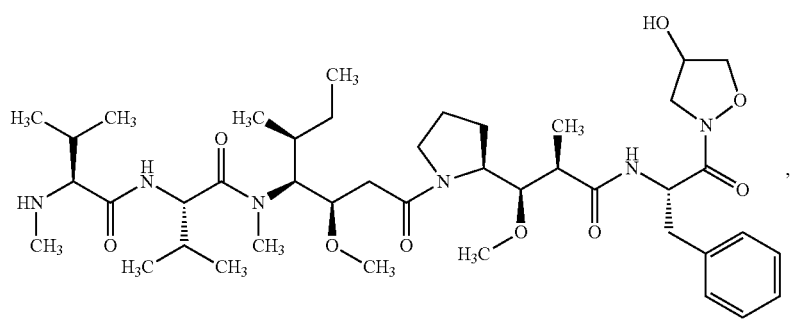
or its salt, solvate, or solvate of the salt.
13. The compound of claim 9, wherein said compound is selected from the group consisting of:
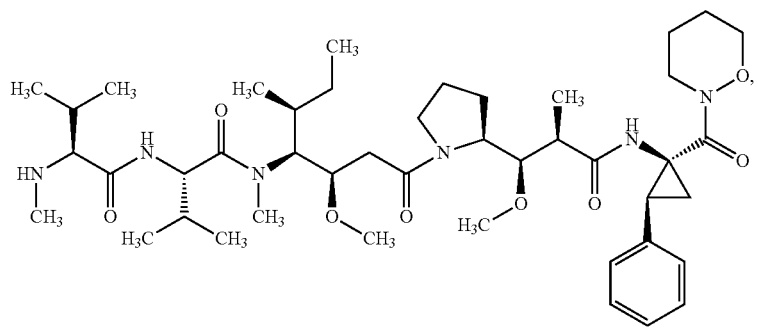

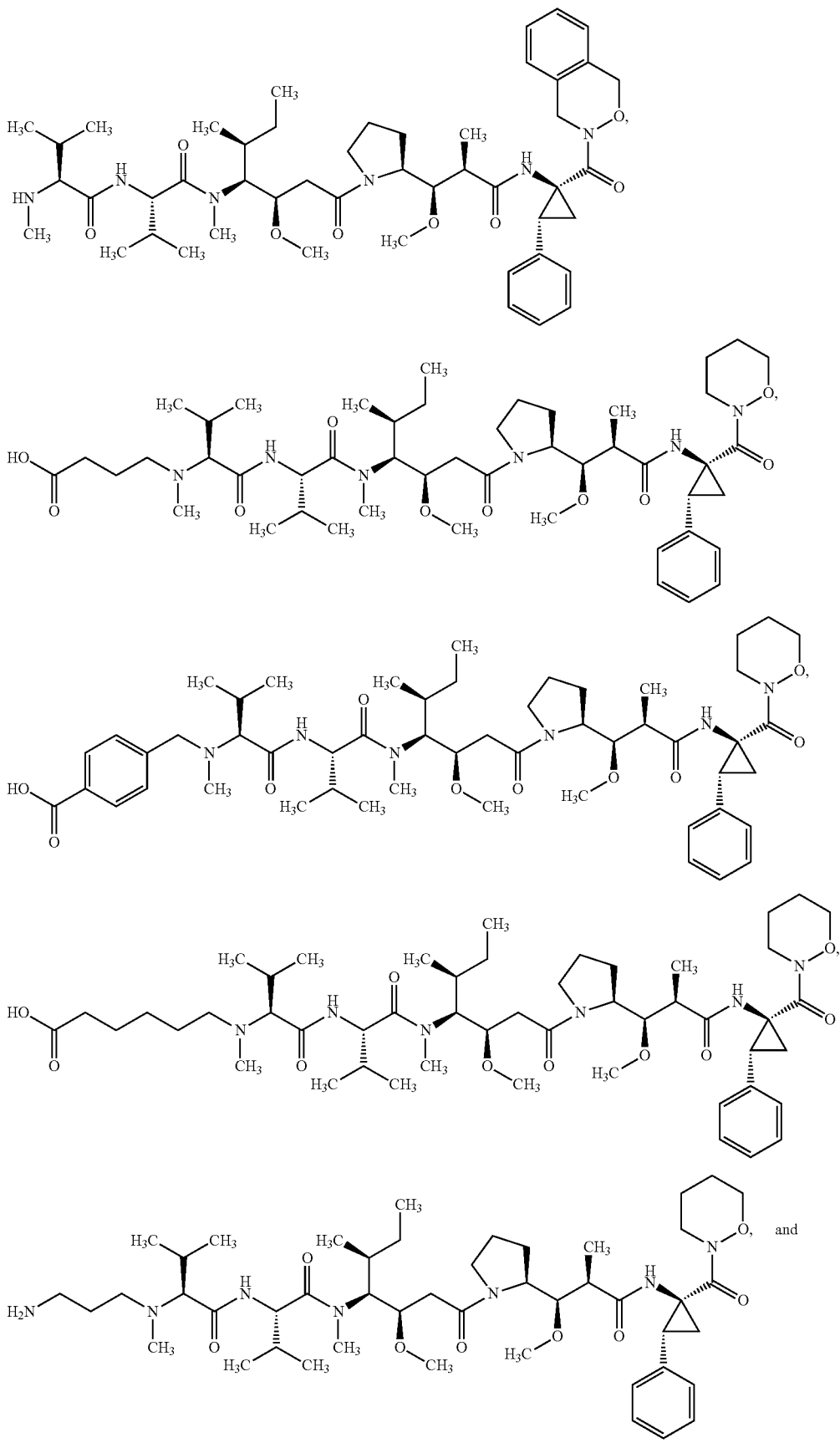

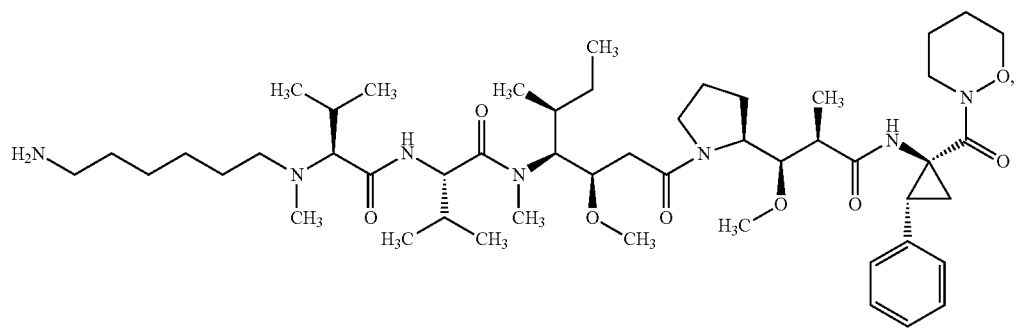
or its salt, solvate, or solvate of the salt.
14. The compound of claim 9, wherein said compound is:
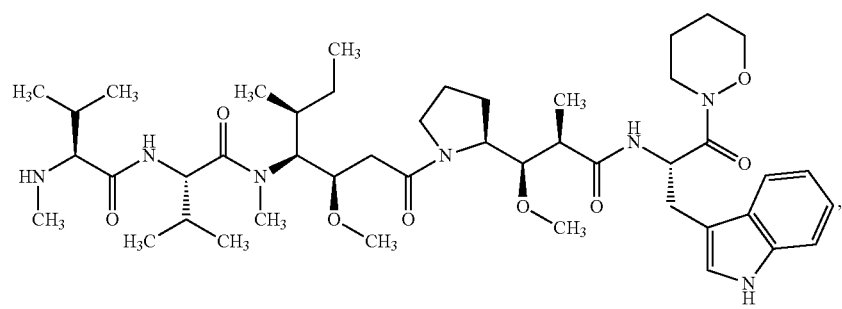 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)N1CCCCO1)OC)N(C)C(=O)[C@@H](NC(=O)[C@@H](NC)C(C)C)C(C)C]
or its salt, solvate, or solvate of the salt.
15. The compound of claim 9, wherein said compound is:
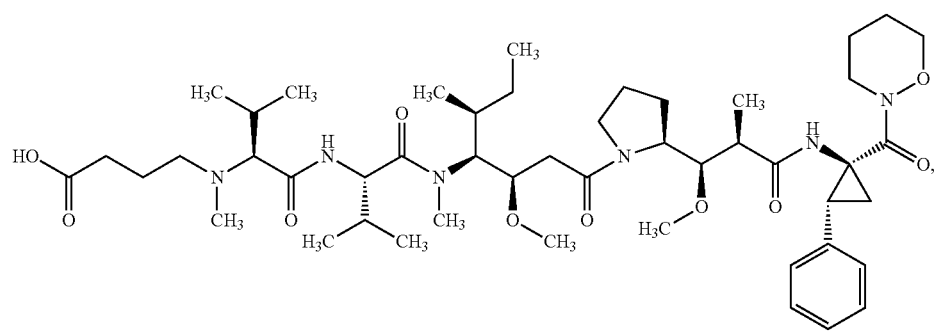 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCC(=O)O)C(C)C]
or its salt, solvate, or solvate of the salt.

16. The compound of claim 9, wherein said compound is:

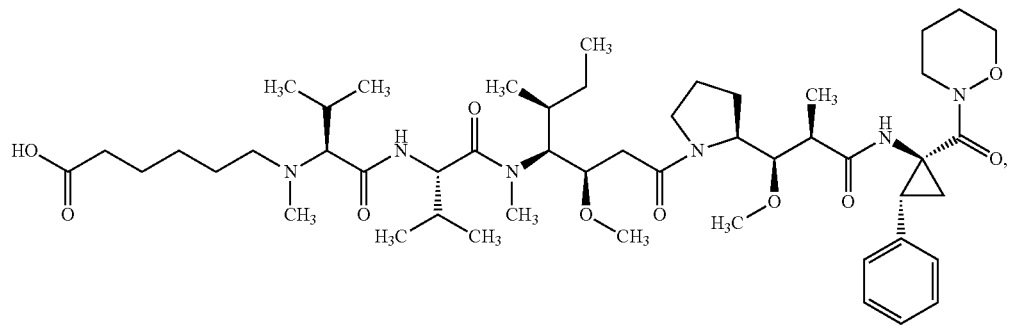 [SMILES: CC[C@H](C)[C@@H]([C@@H](CC(=O)N1CCC[C@H]1[C@H](OC)[C@@H](C)C(=O)N[C@@]1(C(=O)N2CCCCO2)C[C@@H]1c1ccccc1)OC)N(C)C(=O)[C@@H](NC(=O)[C@H](C(C)C)N(C)CCCCCC(=O)O)C(C)C]

or its salt, solvate, or solvate of the salt.

17. The compound of claim 9, wherein said compound is:

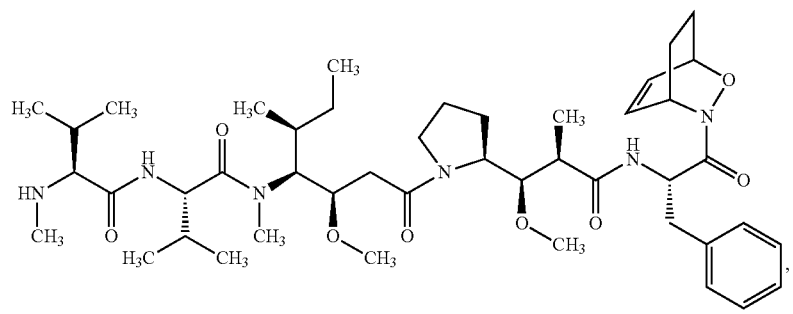 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1OC2C=CC1CC2)OC)N(C)C(=O)[C@@H](NC(=O)[C@@H](NC)C(C)C)C(C)C]

or its salt, solvate, or solvate of the salt.

18. An antiproliferative conjugate, comprising the compound of claim 1 attached to a protein.

19. The antiproliferative conjugate of claim 18, wherein said protein is an antibody.

20. An antiproliferative conjugate, comprising the compound of claim 9 attached to a protein.

21. The antiproliferative conjugate of claim 20, wherein said protein is an antibody.

* * * * *

UNITED STATES PATENT AND TRADEMARK OFFICE
CERTIFICATE OF CORRECTION

PATENT NO. : 8,722,629 B2
APPLICATION NO. : 13/702881
DATED : May 13, 2014
INVENTOR(S) : Hans-Georg Lerchen et al.

It is certified that error appears in the above-identified patent and that said Letters Patent is hereby corrected as shown below:

IN THE CLAIMS:

Column 108, line 4, the portion of the left-hand formula reading "$R^6$" should be changed to --$R^5$--; line 20, for the claim portion reading "solvate, or solvate", should read --hydrate, or hydrate--.

Column 109, line 34, for the claim portion reading "solvate, or solvate", should read --hydrate, or hydrate--; line 55, insert --R1-- at the beginning of the line.

Column 127, the top structure should appear as follows:

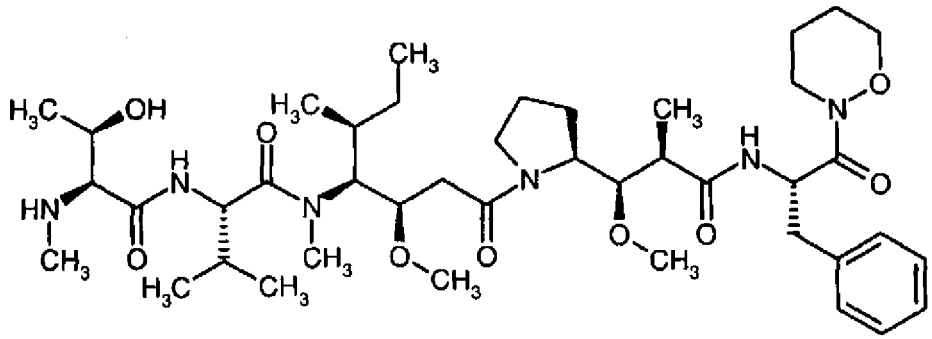

Column 131, line 40, for the claim portion reading "solvate, or solvate", should read --hydrate, or hydrate--.

Column 137, lines 15 and 50, for the claim portions reading "solvate, or solvate", should read --hydrate, or hydrate--; line 16, insert --selected from the group consisting of-- after the word "is".

Column 139, line 49, for the claim portion reading "solvate, or solvate", should read --hydrate, or hydrate--.

Signed and Sealed this
Sixth Day of January, 2015

Michelle K. Lee
*Deputy Director of the United States Patent and Trademark Office*

CERTIFICATE OF CORRECTION (continued)
U.S. Pat. No. 8,722,629 B2

Column 143, each line following the top formula, the middle formula, and the bottom formula, for the claims portion reading "solvate, or solvate", should read --hydrate, or hydrate--.

Column 145, each line following the top formula and the bottom formula, for the claims portion reading "solvate, or solvate", should read --hydrate, or hydrate--.